(12) United States Patent
Pawlowski et al.

(10) Patent No.: US 6,358,665 B1
(45) Date of Patent: Mar. 19, 2002

(54) RADIATION-SENSITIVE COMPOSITION OF CHEMICAL AMPLIFICATION TYPE

(75) Inventors: Georg Pawlowski; Hiroshi Okazaki; Yoshiaki Kinoshita; Naoko Tsugama; Aritaka Hishida; Xiao-Ming Ma, all of Shizuoka; Yuko Yamaguchi, Isehara, all of (JP)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 09/529,371

(22) PCT Filed: Aug. 9, 1999

(86) PCT No.: PCT/JP99/04304
  § 371 Date: Jul. 3, 2000
  § 102(e) Date: Jul. 3, 2000

(87) PCT Pub. No.: WO00/08525
  PCT Pub. Date: Feb. 17, 2000

(30) Foreign Application Priority Data

Aug. 7, 1998 (JP) .......................... 10-225029
  Mar. 29, 1999 (JP) .......................... 11-080736

(51) Int. Cl.7 .............................. G03F 7/004
(52) U.S. Cl. .................. 430/270.1; 430/914; 430/921; 568/28; 568/34; 568/35
(58) Field of Search .................. 430/270.1; 730/270.1, 730/914, 921; 568/28, 34, 35

(56) References Cited

U.S. PATENT DOCUMENTS 5,442,023 A * 8/1995 Argyropoulos et al. ..... 526/320
5,773,191 A * 6/1998 Padmanaban et al. ... 430/270.1

FOREIGN PATENT DOCUMENTS

EP  898201  * 2/1999

OTHER PUBLICATIONS

Houlihan, F.M. et al. SPIE, vol. 3678, Mar. 1999, 264–274.*
Research Disclosure 33701, 5–1992.*

* cited by examiner

*Primary Examiner*—Rosemary Ashton
(74) *Attorney, Agent, or Firm*—Kirshna Banerjee

(57) ABSTRACT

Disclosed is a chemically amplified radiation sensitive composition containing a hydroxystyrene resin and an onium salt precursor which generates a fluorinated alkanesulfonic acid as a photoacid generator, wherein the photoacid generator is a sulfonium or iodonium salt of a fluorinated alkane sulfonic acid, represented by formula (I):

$$Y^+ASO_3^- \qquad (I)$$

wherein A represents $CF_3CHFCF_2$ or $CF_3CF_2CF_2CF_2$; and Y represents

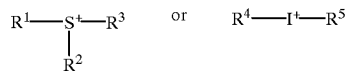

wherein $R^1$, $R^2$, $R^3$, $R^4$, and $R^5$ each independently represent an alkyl group, a monocyclic or bicyclic alkyl group, a cyclic alkylcarbonyl group, a phenyl group, a naphthyl group, an anthryl group, a peryl group, a pyryl group, a thienyl group, an aralkyl group, or an arylcarbonylmethylene group, or any two of $R^1$, $R^2$, and $R^3$ or $R^4$ and $R^5$ together represent an alkylene or an oxyalkylene which forms a five- or six-membered ring together with the interposing sulfur or iodine, said ring being optionally condensed with aryl groups.

42 Claims, No Drawings

RADIATION-SENSITIVE COMPOSITION OF CHEMICAL AMPLIFICATION TYPE

BACKGROUND OF THE INVENTION

1. Field of the Invention

The present invention relates to a chemically amplified radiation sensitive composition, and more particularly to the so-called "photoresist" for the manufacture of electronic components, printing plates, and three-dimensional micro objects.

2. Background Art

An increase in the processor speed attained by the development of microelectronic devices with higher integration density in the electronic industry has lead to a demand for further improved radiation sensitive compositions. That is, an improvement in properties, such as resolution of photoresists and dimensional accuracy of images, has been required for satisfying demands in the microelectronic device production industry.

According to the Rayleigh's equation $$R = k_1 * \lambda / NA$$

wherein R denotes the ultimate resolution, $k_1$ is a constant, $\lambda$ is the wavelength of the light source used in exposure, and NA is the numerical aperture of the illuminating optical system, use of a light source having shorter wavelength in exposure can most effectively enhance the ultimate resolution. This has been effectively applied to the transition of irradiation technology from g-line (436 nm) to i-line (365 nm), and has pushed the resolution limits of conventional near UV irradiation technology to below 0.30 $\mu$m. With the need to produce even smaller features, shorter wavelength radiation, such as deep UV (DUV) radiation (150–320 nm), has become employed. Photons generated from DUV radiation exhibit higher energy than those generated from near UV radiation sources. Therefore, the number of photons per unit energy is smaller, leading to a demand for radiation sensitive compositions with higher sensitivity.

Radiation sensitive compositions called "chemically amplified photoresists" are known in the art, and are advantageous in that the catalytic imaging process can provide high photosensitivity. By virtue of high photosensitivity and high resolution, the chemically amplified radiation sensitive compositions are being substituted for conventional radiation sensitive compositions and being spread. The chemically amplified radiation sensitive compositions comprise a radiation sensitive acid generating agent (photoacid generator; hereinafter often referred to as "PAG") which generates an acid. Upon exposure, this PAG releases an acid which catalyzes a layer dissolution reaction in the case of positive-working photoresists and catalyzes a crosslinking reaction in the case of negative-working photoresists.

Positive-working chemically amplified photoresists are the so-called "two component systems" which basically comprise: (1) a resin which has been rendered insoluble in alkaline solutions by masking at least a part of the water soluble groups on the resin with an acid cleavable protective group; and (2) a PAG. Optionally, low molecular weight or phenol derivatives masked with acid cleavable protective groups described below are added to further improve the lithographic performance. This system is known as a "three component chemically amplified radiation sensitive composition. Upon exposure, the PAG produces a strong acid capable of cleaving the bond between protective group and the resin, resulting in the formation of an alkali-soluble resin. Acid molecules produced from the PAG upon exposure are not consumed by a single reaction for cleaving the protective group from the resin, and one acid molecule produced during the exposure can cleave a large number of protective groups from the resin. This contributes to the high sensitivity of chemically amplified radiation sensitive compositions.

Many two or three component positive-working photoresist compositions comprising polyhydroxystyrene resins or phenol derivatives having polyfunctional groups have been described in patents and literature. In the case of positive-working two component photoresist compositions, the phenolic groups of the polymer are partly or fully protected by acid-cleavable protective groups, for example, t-butoxycarbonyl groups (U.S. Pat No. 4,491,628), t-butoxycarbonylmethyl groups (U.S. Pat. No. 5,403,695), t-butyl groups, trimethylsilyl groups, tetrahydropyranyl groups (U.S. Pat. No. 5,350,660), 2-(alkoxyethyl) groups (U.S. Pat. No. 5,468,589 and U.S. Pat. No. 5,558,971, and U.S. Pat. No. 5,558,976), or combinations thereof. A co- or terpolymer of hydroxystyrene with (meth)acrylic acid, wherein the carboxylic acid is partly or fully protected by acid-cleavable groups, such as t-butyl groups (U.S. Pat. No. 4,491,628, U.S. Pat. No. 5,482,816, and U.S. Pat. No. 5,492,793), amyl groups, or tetrahydropyranyl groups, has also been regarded as useful for positive-working two component photoresist compositions. The addition of dissolution inhibitors, which have been protected in the same manner as described above, to the positive-working photoresist composition is described in U.S. Pat. No. 5,512,417 and U.S. Pat. No. 5,599,949.

In the case of negative-working photoresists, a crosslinking agent, such as hexamethoxy methylmelamine, is added to an alkali soluble phenolic resin (U.S. Pat. No. 5,376,504 and U.S. Pat. No. 5,389,491). The acid produced from the PAG upon exposure induces a crosslinking reaction in the exposed areas.

As is apparent from the foregoing description, PAG plays an important role in the imaging process for both positive-working and negative-working chemically amplified resists, because PAG governs light response properties, such as absorption of light or quantum yield of acid formation, and, in addition, governs the properties of the produced acid, such as acid strength, mobility, or volatility. Useful PAGs for both positive-working and negative-working chemically amplified resists include ionic onium salts, particularly iodonium salts or sulfonium salts with strong non-nucleophilic anions (U.S. Pat. No. 4,058,400 and U.S. Pat. No. 4,933,377), for example, hexafluoroantimonate and trifluoromethane sulfonate (U.S. Pat. No. 5,569,784) or aliphatic/aromatic sulfonates (U.S. Pat. No. 5,624,787). In addition, many non-ionic PAGs producing the above mentioned sulfonic acids have been described for both positive-working and negative-working chemically amplified photoresist materials (U.S. Pat. No. 5,286,867 and U.S. Pat. No. 5,338,641). Further, certain hydrogen halide producing PAGs have been suggested for advantageous use in negative-working chemically amplified resists (U.S. Pat. No. 5,599,949).

U.S. Pat. No. 5,731,364 discloses that binulear sulfonium compounds having perfluoroaryl sulfonate and perfluoroalkyl sulfonate are useful for the image formation of positive-working and negative-working photoresists.

This patent, however, does not suggest specific superiority in use of sulfonium compounds of nonafluorobutane sulfonate as PAGs in combination with hydroxystyrene based resin having a protective group which can be eliminated with an acid.

Among these PAGs, those onium salts producing trifluoromethane sulfonic acids upon exposure are particularly preferred, because superior sensitivity and good ultimate resolution of the photoresist system can be obtained. In addition, these PAGs are known to reduce the formation of insolubles on the substrate or at the substrate/resist interface known as scum.

It was found, however, that minor quantities of the rather volatile trifluoromethane sulfonic acid (TFSA) produced during the irradiation process may evaporate (outgas) from the photoresist film and cause corrosion of the exposure and process equipment. The same trouble is observed when hydrogen halide producing PAGs are used. It may be anticipated that a long time exposure especially to the evaporating fumes of the volatile, aggressive TFSA may cause hazards to the health of the labor force. In addition, it is known that resist materials containing PAGs which produce TFSA tend to produce the so-called T-shaped pattern profiles, and show linewidth changes upon process delays (i.e. inadequate delay time stability) due to the high volatility and the diffusion properties of this acid. Attempts to identify an adequate replacement for TFSA, or its onium salt precursors, respectively, were so far not very successful, because deterioration of the resist performance, i.e. of resolution capability, or sensitivity occurred.

An evaluation of a chemically amplified resist system using a large number of sulfonic acids producing onium salt precursors has revealed that most acids yielding good resolution are poor in sensitivity, while those compounds, which yield high sensitive resists do not perform very well in terms of resolution. More specifically, it was found that low-molecular weight aliphatic and some aromatic sulfonic acids have high vapor pressures, thus causing the above mentioned corrosion of the equipment, forming T-topped photoresist profiles, and yielding significant linewidth changes upon process time delays, while larger molecular weight aliphatic and aromatic sulfonic acids do not provide the required sensitivity, or have inadequate resolution power.

SUMMARY OF THE INVENTION

The present inventors have made extensive and intensive studies on improved chemically amplified resist materials for production of semiconductors, particularly chemically amplified resist materials which are less likely to cause corrosion of equipment by outgassing and, at the same time, has good sensitivity and resolution. As a result, the present inventors have now found that a combination of a film forming hydroxystyrene based resin with an onium salt precursor capable of generating a fluorinated alkanesulfonic acid as a photoacid generator can provide an excellent chemically amplified radiation sensitive composition. The present invention has been made based on such finding.

Accordingly, it is an object of the present invention to provide a chemically amplified radiation sensitive composition which is less likely to cause the corrosion of the equipment, T-topped photoresist profiles, and significant linewidth changes upon process time delays.

It is another object of the present invention to provide a chemically amplified radiation sensitive composition which can realize high sensitivity and resolution, good pattern shapes and stability thereof.

It is still another object of the present invention to provide a chemicaqlly amplified radiation sensitive composition containing a photoacid generator which, by virtue of the generation of a nonvolatile acid, can eliminate problems associated with outgassing.

It is a further object of the present invention to provide a recording medium containing the chemically amplified radiation sensitive composition according to the present invention and to provide a process for producing the recording medium.

The chemically amplified radiation sensitive composition according to the present invention comprises at least an onium salt precursor which generates a fluorinated alkanesulfonic acid as a photoacid generator and a film forming hydroxystyrene based resin.

According to a preferred embodiment of the present invention, there is provided a positive-working chemically amplified radiation sensitive composition, as a first aspect of the present invention, comprising:

(1) an onium salt precursor which generates a fluorinated alkanesulfonic acid as a photoacid generator;

(2) a film forming hydroxystyrene based resin which is is made alkali insoluble by protecting alkali soluble groups on the resin with an acid cleavable protective group; and (3) optionally a dissolution inhibitor having at least one acid cleavable C—O—C or C—O—Si bonds.

According to a second aspect of the present invention, there is provided a negative-working chemically amplified radiation sensitive composition comprising:

(1) an onium salt precursor which generates a fluorinated alkanesulfonic acid as a photoacid generator;

(2) an alkali soluble film forming hydroxystyrene based resin; and (3) optionally an acid-sensitive crosslinking agent.

According to a third aspect of the present invention, there is provided a radiation sensitive recording medium comprising: a substrate; and a radiation sensitive layer provided on the substrate, the radiation sensitive comprising the composition of the present invention.

According to a fourth aspect of the present invention, here is provided a process for producing a radiation sensitive recording medium, comprising the steps of: dissolving the composition of the present invention in a solvent; coating the solution onto a substrate to form a radiation sensitive layer; and removing the solvent by evaporation.

PREFERRED EMBODIMENTS OF THE INVENTION

Chemically Amplified Radiation Sensitive Composition

The chemically amplified radiation sensitive composition according to the present invention basically comprises a film forming hydroxystyrene based resin and an onium salt precursor which generates a fluorinated alkanesulfonate as a photoacid generator.

According to the chemically amplified radiation sensitive composition of the present invention, the fluorinated alkanesulfonic acid generated from the onium salt precursor upon exposure can significantly improve the performance of the chemically amplified radiation sensitive composition containing a hydroxystyrene based resin in terms of image formation, that is, resolution, dense/isolated line bias, dimensional accuracy of images, delay time stability, a reduction in volatile components (outgas) and the like.

Surprisingly, the onium salt of a fluorinated alkanesulfonic acid as the photoacid generator, when used in a (a) positive-working or (b) negative-working hydroxystyrene based chemically amplified radiation sensitive composition, can provide radiation sensitivity equal to that in the case of the corresponding trifluoromethane sulfonate derivatives. Further, use of the photoacid generator according to the present invention provides substantially the same resolution and, in addition, does not form any scum. Further, surprisingly, better (rectangular) pattern profile accuracy, and less line surface and edge roughness are observed. Due to the low vapor pressure of the fluorinated alkanesulfonic acid, the evaporation tendency of this compound is almost negligible at typical photoresist process temperatures (up to about 150° C.), thus eliminating both the formation of T-tops and the risk of equipment corrosion. In addition, linewidth changes are minimized, as the mobility and thus the diffusion range of the comparatively large molecular weight fluorinated alkanesulfonic acid in chemically amplified radiation sensitive films are smaller than that of trifluoromethanesulfonic acid. The reduced mobility has a positive effect on the dense lines to isolated line bias; i.e. the linewidth dimensions of isolated lines and dense lines are almost equal at a given exposure dose. Therefore, the use of the onium salts of the present invention very advantageously contributes in several important ways to the overall performance of (a) positive-working and (b) negative-working hydroxystyrene based chemically amplified radiation sensitive compositions, as well as to the life-time and maintenance of the equipment employed, and to the health of the work forces.

(a) Photoacid Generator

The photoacid generator used in the compositon of the present invention is an onium salt precursor which generates a fluorinated alkanesulfonic acid. The onium salt precursor is not particularly limited so far as it can generate a fluorinated alkanesulfonic acid. According to a preferred embodiment the present invention, the onium salt precursor is a sulfonium salt or an iodonium salt.

The fluorinated alkanesulfonic acid also is not particularly limited. Preferably, the fluorinated alkanesulfonic acid is such that the alkanesulfonic acid has 3 to 4 carbon atoms.

Preferred onium salt precursors, which generate fluorinated alkanesulfonic acids, include sulfonium salts or iodonium salts of 3,3,3,3,1,1-hexafluoropropanesulonate and nonafluorobutanesulonic acid.

According to a more preferred embodiment of the present invention, the onium salt precursor, which generates a fluorinated alkanesulfonic acid, is a sulfonium or iodonium salt of a fluorinated alkane sulfonate of formula (I):

$$Y^+ASO_3^-  \qquad (I)$$

wherein A represents $CF_3CHFCF_2$ or $CF_3CF_2CF_2CF_2$; and Y represents

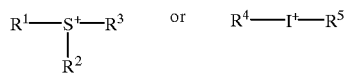

wherein $R^1$, $R^2$, $R^3$, $R^4$, and $R^5$ each independently represent an alkyl group,
a monocyclic or bicyclic alkyl group,
a cyclic alkylcarbonyl group,
a phenyl group,
a naphthyl group,
an anthryl group,
a peryl group,
a pyryl group,
a thienyl group,
an aralkyl group, or
an arylcarbonylmethylene group, or
any two of $R^1$, $R^2$, and $R^3$ or $R^4$ and $R^5$ together represent an alkylene or an oxyalkylene which forms a five- or six-membered ring together with the interposing sulfur or iodine, said ring being optionally condensed with aryl groups,
one or more hydrogen atoms of $R^1$, $R^2$, $R^3$, $R^4$, and $R^5$ being optionally substituted by one or more groups selected from the group consisting of a halogen atom, an alkyl group, a cyclic alkyl group, an alkoxy group, a cyclic alkoxy group, a dialkylamino group, a dicyclic dialkylamino group, a hydroxyl group, a cyano group, a nitro group, an aryl group, an aryloxy group, an arylthio group, and groups of formulae (II) to (VI):

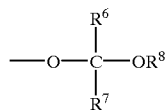
(II)

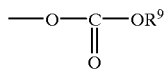
(III)

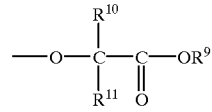
(IV)

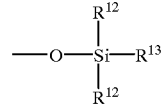
(V)

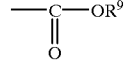
(VI)

wherein $R^6$ and $R^7$ each independently represent a hydrogen atom, an alkyl group, which may be substituted by one or more halogen atoms, or a cyclic alkyl group, which may be substituted by one or more halogen atoms, or $R^6$ and $R^7$ together can represent an alkylene group to form a ring, $R^8$ represents an alkyl group, a cyclic alkyl group, or an aralkyl group, or $R^6$ and $R^8$ together represent an alkylene group which forms a ring together with the interposing —C—O— group, the carbon atom in the ring being optionally substituted by an oxygen atom, $R^9$ represents an alkyl group or a cyclic alkyl group, one or two carbon atoms in the alkyl group or the cyclic alkyl group being optionally substituted by an oxygen atom, an aryl group, or an aralkyl group, $R^{10}$ and $R^{11}$ each independently represent a hydrogen atom, an alkyl group, or a cyclic alkyl group, $R^{12}$ represents an alkyl group, a cyclic alkyl group, an aryl group, or an aralkyl group, and $R^{13}$ represents an alkyl group, a cyclic alkyl group, an aryl group, an aralkyl group, the group —$Si(R^{12})_2R^{13}$, or the group —O—$Si(R^{12})_2R^{13}$.

The compound represented by formula (I) is advantageous in that it has good solubility in general solvents used in radiation sensitive compositions and, in addition, has good affinity for the components contained in the radiation sensitive composition.

In formula (I), the alkyl group as a group or a part of a group may be of straight chain type or branched chain type. The halogen refers to a fluorine, chlorine, bromine, or iodine atom. The aralkyl refers to benzyl, phenylethyl (phenetyl), methylbenzyl, naphthylmethyl or the like. The aryl preferably refers to phenyl, naphthyl, tolyl or the like.

According to a preferred embodiment of the present invention, a group of preferred compounds represented by formula (I) are those wherein $R^1$, $R^2$, $R^3$, $R^4$, and $R^5$ each independently represent
a $C_{1-12}$ alkyl group (preferably a $C_{1-6}$ alkyl group, more preferably a $C_{1-3}$ alkyl group),
a $C_{6-12}$ monocyclic or bicyclic alkyl group (preferably $C_{3-6}$ monocyclic alkyl group or a $C_{10-12}$ bicyclic alkyl group),
a $C_{4-12}$ cyclic alkylcarbonyl group (preferably a $C_{3-6}$ monocyclic alkylcarbonyl group),
a phenyl group,
a naphtyl group,
an anthryl group,
a peryl group,
a pyryl group,
a thienyl group,
an aralkyl group, or
an arylcarbonylmethylene group with up to 15 carbon atoms, or
any two of $R^1$, $R^2$, and $R^3$, or $R^4$ and $R^5$ together represent an alkylene or an oxyalkylene which forms a five- or six-membered ring together with the interposing sulfur or iodine atom, said ring being optionally condensed with aryl groups.

According to a more preferred embodiment of the present invention, the compounds represented by formula (I) are those wherein one or more hydrogen atoms of $R^1$, $R^2$, $R^3$, $R^4$, and $R^5$ are substituted by at least one group selected from the group consisting of a halogen atom, a $C_{1-6}$ alkyl group, a $C_{3-6}$ cyclic alkyl group, a $C_{1-6}$ alkoxy group, a $C_{3-6}$ cyclic alkoxy group, a di-$C_{1-3}$ alkylamino group, a cyclic di-$C_{6-12}$ alkylamino group, a hydroxyl group, a cyano group, a nitro group, an aryl group, an aryloxy group, an arylthio group, and groups represented by formulae (II) to (VI). Further, compounds are preferably utilized wherein, in the groups represented by formulae (II) to (VI), $R^6$ and $R^7$ each independently represent a hydrogen atom, a $C_{1-6}$ alkyl group, which may be substituted by one or more halogen atoms, or a $C_{3-6}$ cyclic alkyl group, which may be substituted by one or more halogen atoms, or $R^6$ and $R^7$ together represent an alkylene group to form a five-membered or six-membered ring, $R^8$ represents a $C_{1-6}$ alkyl group, a $C_{3-6}$ cyclic alkyl group, or a $C_{7-12}$ aralkyl group, or $R^6$ and $R^8$ together represent an alkylene group which forms a five- or six-membered ring together with the interposing —C—O— group, the carbon atom in the ring being optionally substituted by an oxygen atom, $R^9$ represents a $C_{1-6}$ alkyl group or a $C_{3-6}$ cyclic alkyl group, one or two carbon atoms in the alkyl group or the cyclic alkyl group being optionally substituted by an oxygen atom, a $C_{6-12}$ aryl group, or a $C_{7-12}$ aralkyl group, $R^{10}$ and $R^{11}$ each independently represent a hydrogen atom, a $C_{1-6}$ alkyl group, or a $C_{3-6}$ cyclic alkyl group, $R^{12}$ represents a $C_{1-6}$ alkyl group, a $C_{3-6}$ cyclic alkyl group, a $C_{6-12}$ aryl group, or a $C_{7-12}$ aralkyl group, and $R^{13}$ represents a $C_{1-6}$ alkyl group, a $C_{3-6}$ cyclic alkyl group, a $C_{6-12}$ aryl group, a $C_{7-12}$ aralkyl group, group —Si($R^{12}$)$_2$$R^{13}$, or group —O—Si($R^{12}$)$_2$$R^{13}$.

According to another preferred embodiment of the present invention, a group of compounds represented by formula (I) are utilized wherein $R^1$, $R^2$, $R^3$, $R^4$, and $R^5$ each independently represent a $C_{1-3}$ alkyl group, a $C_{3-6}$ monocyclic alkyl group, $C_{10-12}$ bicyclic alkyl group, a $C_{3-6}$ cyclic alkylcarbonyl group, a phenyl group, or a naphthyl group, or any two of $R^1$, $R^2$ and $R^3$, or $R^4$ and $R^5$ together represent an alkylene group to form a five- or six-membered alkylene ring, one or more hydrogen atoms of $R^1$, $R^2$, $R^3$, $R^4$, and $R^5$ optionally substituted by at least one group selected from the group consisting of a hydrogen atom, a halogen atom, a $C_{1-6}$ alkyl group, a $C_{3-6}$ cyclic alkyl group, a $C_{1-6}$ alkoxyl group, a $C_{3-6}$ cyclic alkoxyl group, a hydroxyl group, an aryl group, an aryloxy group, an arylthio group, and groups of formulae (II) to (VI) wherein $R^6$ and $R^7$ each independently represent either a hydrogen atom or a methyl group, provided that $R^6$ and $R^7$ do not simultaneously represent hydrogen, Ra represents either a $C_{1-4}$ alkyl group or $R^6$ and $R^8$ together represent an alkylene group which forms a ring together with the interposing —C—O— group, $R^9$ represents a $C_{1-4}$ alkyl group, $R^{10}$ and $R^{11}$ represent a hydrogen atom, $R^{12}$ represents a methyl group, and $R^{13}$ represents a methyl group.

According to the present invention, the most preferred compounds represented by formula (1) are tris-(4-t-butylphenyl)sulfonium 3,3,3,2,1,1-hexafluorobutane sulfonate and tris-(4-t-butylphenyl) sulfonium nonafluorobutane sulfonate. These compounds can advantageously offer excellent lithographic performance and, in addition, can be easily synthesized.

Specific examples of preferred onium salts represented by formula (I) include, but are not limited to, the following compounds (in this list, sulfonium 3,3,3,2,1,1-hexafluorobutane sulfonate is abbreviated as S-HFPS and iodonium 3,3,2,1,1-hexafluorobutane sulfonate is abbreviated as I-HFPS): triphenyl S-HFPS, 4-methylphenyl diphenyl S-HFPS, bis-(4-methylphenyl) phenyl S-HFPS, tris-(4-methylphenyl) S-HFPS, 4-t-butylphenyl diphenyl S-HFPS, bis-(4-t-butylphenyl) phenyl S-HFPS, tris-(4-t-butylphenyl) S-HFPS, 4-cyclohexylphenyl diphenyl S-HFPS, bis-(4-cyclohexylphenyl) phenyl S-HFPS, tris-(4-cyclohexylphenyl) S-HFPS, 4-chlorophenyl diphenyl S-HFPS, bis-(4-chlorophenyl) phenyl S-HFPS, tris-(4-chlorophenyl) S-HFPS, 4-N,N-dimethylaminophenyl diphenyl S-HFPS, bis-(4-N,N-dimethylaminophenyl) phenyl S-HFPS, tris-(4-N,N-dimethylaminophenyl) S-HFPS, 4-hydroxyphenyl diphenyl S-HFPS, bis-(4-hydroxyphenyl) phenyl S-HFPS, tris-(4-hydroxyphenyl) S-HFPS, 4-methoxyphenyl diphenyl S-HFPS, bis-(4-methoxyphenyl) phenyl S-HFPS, tris-(4-methoxyphenyl) S-HFPS, 4-t-butyloxyphenyl diphenyl S-HFPS, bis-(4-t-butyloxyphenyl) phenyl S-HFPS, tris-(4-t-butyloxyphenyl) S-HFPS, 3,5-dimethyl-4-hydroxyphenyl diphenyl S-HFPS, bis-(3,5-dimethyl-4-hydroxyphenyl) phenyl S-HFPS, tris-(3,5-dimethyl-4-hydroxyphenyl) S-HFPS, 4-t-butyloxycarbonyloxyphenyl diphenyl S-HFPS, bis-(4-t-butyloxycarbonyloxyphenyl) phenyl S-HFPS, tris-(4-t-butyloxycarbonyloxyphenyl) S-HFPS, 4-t- butyloxycarbonylphenyl diphenyl S-HFPS, bis-(4-t-butyloxycarbonylphenyl) phenyl S-HFPS, tris-(4-t-butyloxycarbonylphenyl) S-HFPS, 4-t-butyloxycarbonylmethylenoxyphenyl diphenyl S-HFPS, bis-(4-t-butyloxycarbonylphenyl) phenyl S-HFPS, tris-(4-t-butyloxycarbonylphenyl) S-HFPS, 4-phenythiophenyl diphenyl S-HFPS, bis-(4-phenylthiophenyl diphenyl) phenyl S-HFPS, tris-(4-phenylthiophenyl diphenyl) S-HFPS, 2-naphthyl diphenyl S-HFPS, phenyl anthrylium HFPS, phenyl thioanthrylium HFPS, 9-anthryl diphenyl S-HFPS, 4 methylphenyl bis-(4-t-butylphenyl) S-HFPS, bis-(4-methylphenyl) 4-t-butylphenyl S-HFPS, 4-t-butyloxyphenyl bis-(4-t-butylphenyl) S-HFPS, bis-(4-t-butyloxyphenyl) 4-t-butylphenyl S-HFPS, 4-cyclohexylphenyl bis-(4-t-butylphenyl) S-HFPS, bis-(4-cyclohexylphenyl) 4-t-butylphenyl S-HFPS, 4-chlorophenyl bis-(4-t-butylphenyl) S-HFPS, bis-(4-chlorophenyl) 4-t-butylphenyl S-HFPS, 4-N,N-dimethylaminophenyl bis-(4-t-butylphenyl) S-HFPS, bis-(4-N,N-dimethylaminophenyl) 4-t -butylphenyl S-HFPS, 4-hydroxyphenyl bis-(4-t-butylphenyl) S-HFPS, bis-(4-hydroxyphenyl) 4-t-butylphenyl S-HFPS, 4-methoxyphenyl bis-(4-t-butylphenyl) S-HFPS, bis-(4-methoxyphenyl) 4-t-butylphenyl S-HFPS, 3,5-dimethyl-4-hydroxyphenyl bis-( 4-t-butylphenyl) S-HFPS, bis-(3,5-dimethyl-4-hydroxyphenyl) 4-t-butylphenyl S-HFPS, 4-t-butyloxycarbonyloxyphenyl bis-(4-t-butylphenyl) S-HFPS, bis-(4-t-butyloxycarbonyl oxyphenyl) 4-t-butylphenyl S-HFPS, 4-t-butyloxycarbonyl phenyl bis-(4-t-butylphenyl) S-HFPS, bis-(4-t-butyloxycarbonylphenyl) 4-t-butylphenyl S-HFPS, 4-t-butyloxycarbonyl methylenoxyphenyl bis-(4-t-butylphenyl) S-HFPS, bis-(4-t-butyloxycarbonylmethylen oxyphenyl) 4-t-butylphenyl S-HFPS, 4-phenylthiophenyl bis-(4-t-butylphenyl) S-HFPS, bis-(4-phenylthiophenyl) 4-t-butylphenyl S-HFPS, 2-naphthyl bis-(4-t-butylphenyl) S-HFPS, 9-anthryl bis-(4-t-butylphenyl) S-HFPS, bis-(4-methylphenyl) 4-methoxyphenyl S-HFPS, 4-t-butylphenyl bis-(4-methoxyphenyl) S-HFPS, bis-(4-t-butylphenyl) 4-methoxyphenyl S-HFPS, 4-cyclohexylphenyl bis-(4-methoxyphenyl) S-HFPS, bis-(4-cyclohexylphenyl) 4-methoxyphenyl S-HFPS, 4-chlorophenyl bis-(4-methoxyphenyl) S-HFPS, bis-(4-chlorophenyl) 4-methoxyphenyl S-HFPS, 4-N,N-dimethylaminophenyl bis-(4-methoxyphenyl) S-HFPS, bis-(4-N,N-dimethylaminophenyl ) 4-methoxyphenyl S-HFPS , 4-hydroxyphenyl bis-(4-methoxyphenyl) S-HFPS, bis-(4-hydroxyphenyl) 4-methoxyphenyl S-HFPS, 4-t-butyloxyphenyl bis-(4-methoxyphenyl) S-HFPS, bis-(4-t-butyloxyphenyl) 4-methoxyphenyl S-HFPS, 3,5-dimethyl-4-hydroxyphenyl bis-(4-methoxyphenyl) S-HFPS, bis-(3,5-dimethyl-4-hydroxyphenyl) 4-methoxyphenyl S-HFPS, 4-t-butyloxycarbonyl oxyphenyl bis-(4-methoxyphenyl) S-HFPS, bis-(4-t-butyloxy carbonyloxyphenyl) 4-methoxyphenyl S-HFPS, 4-t-butyloxycarbonylphenyl bis-(4-methoxyphenyl) S-HFPS, bis-(4-t-butyloxycarbonylphenyl) 4-methoxyphenyl S-HFPS, 4-t-butyloxycarbonyl methylenoxyphenyl bis-(4-methoxyphenyl ) S-HFPS, bis-(4-t-butyloxycarbonylmethylen oxyphenyl) 4-methoxyphenyl S-HFPS, 4-phenylthiophenyl bis-(4-methoxyphenyl) S-HFPS, bis-(4-phenylthiophenyl) 4-methoxyphenyl S-HFPS, 2-naphthyl bis-(4-methoxyphenyl) S-HFPS, 9-anthryl bis-(4-methoxyphenyl) S-HFPS, 4-cyclohexylphenyl bis-(4-t-butyloxyphenyl) S-HFPS, bis-(4-cyclohexylphenyl) 4-t-butyloxyphenyl S-HFPS, 4-chlorophenyl bis-(4-t-butyloxyphenyl) S-HFPS, bis-(4-chlorophenyl) 4-t-butyloxyphenyl S-HFPS, 4-N,N-dimethylaminophenyl bis-(4-t-butyloxyphenyl) S-HFPS, bis-(4-N,N-dimethyl aminophenyl) 4-t-butyloxyphenyl S-HFPS, 4-hydroxyphenyl bis-(4-t-butyloxyphenyl) S-HFPS, bis-(4-hydroxyphenyl) 4-t-butyloxyphenyl S-HFPS, 4-methoxyphenyl bis-(4-t-butyloxyphenyl) S-HFPS, bis-(4-methoxyphenyl) 4-t-butyloxyphenyl S-HFPS, 3,5-dimethyl-4-hydroxyphenyl bis-(4-t-butyloxyphenyl) S-HFPS, bis-(3,5-dimethyl-4-hydroxyphenyl) 4-t-butyloxyphenyl S-HFPS, 4-t-butyloxycarbonyloxyphenyl bis-(4-t-butyloxyphenyl) S-HFPS, bis-(4-t-butyloxycarbonyloxyphenyl) 4-t-butyloxyphenyl S-HFPS, 4-t-butyloxycarbonyl phenyl bis-(4-t-butyloxyphenyl) S-HFPS, bis-(4-t-butyloxycarbonylphenyl) 4-t-butyloxy phenyl S-HFPS, 4-t-butyloxycarbonylmethylenoxyphenyl bis-(4-t-butyloxyphenyl) S-HFPS, bis-(4-t-butyloxycarbonylmethylenoxyphenyl) 4-t-butyloxyphenyl S-HFPS, 4-phenyl thiophenyl bis-(4-t-butyloxyphenyl) S-HFPS, bis-(4-phenylthiophenyl) 4-t-butyloxy phenyl S-HFPS, 2-naphthyl bis-(4--butyloxyphenyl) S-HFPS, 9-anthryl bis-(4-t-butyloxyphenyl) S-HFPS, trimethyl S-HFPS, butyl dimethyl S-HFPS, dibutyl methyl S-HFPS, cyclohexyl methyl S-HFPS, dicyclohexyl methyl S-HFPS, β-oxocyclohexyl dimethyl S-HFPS, β-oxocyclohexyl cyclohexyl methyl S-HFPS, β-oxocyclohexyl 2-norbornyl methyl S-HFPS, phenyl dimethyl S-HFPS, diphenyl methyl S-HFPS, 4-methylphenyl dimethyl S-HFPS, bis-(4-methylphenyl) methyl S-HFPS, 4-t-butylphenyl dimethyl S-HFPS, bis-(4-t-butylphenyl) methyl S-HFPS, 4-t-butyloxyphenyl dimethyl S-HFPS, bis-(4-t-butyloxyphenyl) methyl S-HFPS, 4-cyclohexylphenyl dimethyl S-HFPS, bis-(4-cyclohexylphenyl) methyl S-HFPS, 4-chlorophenyl dimethyl S-HFPS, bis-(4-chlorophenyl) methyl S-HFPS, 4-N,N-dimethylaminophenyl dimethyl S-HFPS, bis-(4-N,N-dimethylaminophenyl) methyl S-HFPS, 4-hydroxyphenyl dimethyl S-HFPS, bis-(4-hydroxyphenyl) methyl S-HFPS, 3,5-dimethyl-4-hydroxyphenyl dimethyl S-HFPS, bis-(3,5-dimethyl-4-hydroxyphenyl) methyl S-HFPS, 3,5-dimethoxy-4-hydroxyphenyl dimethyl S-HFPS, bis-(3,5-dimethoxy-4-hydroxyphenyl) methyl S-HFPS, 4-methoxyphenyl dimethyl S-HFPS, bis-(4-methoxyphenyl) methyl S-HFPS, 4-t-butyloxycarbonyloxyphenyl dimethyl S-HFPS, bis-(4-t-butyloxycarbonyloxyphenyl) methyl S-HFPS, 4-t-butyloxycarbonylphenyl dimethyl S-HFPS, bis-(4-t-butyloxycarbonylphenyl) methyl S-HFPS, 4-t-butyloxycarbonylmethylenoxyphenyl dimethyl S-HFPS, bis-(4-t-butyloxycarbonylmethylenoxyphenyl) methyl S-HFPS, 4-phenylthiophenyl dimethyl S-HFPS, bis-(4-phenylthiophenyl) methyl S-HFPS, 2-naphthyl dimethyl S-HFPS, bis-(2-naphthyl) methyl S-HFPS, 4-hydroxynaphthyl dimethyl S-HFPS, bis-(4-hydroxynaphthyl) methyl S-HFPS, 9-anthryl dimethyl S-HFPS, bis-(9-anthryl) methyl S-HFPS, 2-naphthyl dibutyl S-HFPS, phenyl tetramethylene S-HFPS, 4-methylphenyl tetramethylene S-HFPS, 4-t-butylphenyl tetramethylene S-HFPS, 4-t-butyloxyphenyl tetramethylene S-HFPS, 4-cyclohexylphenyl tetramethylene S-HFPS, 4-chlorophenyl tetramethylene S-HFPS, 4-N,N-dimethylaminophenyl tetramethylene S-HFPS, 4-hydroxyphenyl tetramethylene S-HFPS, 3,5-dimethyl-4-hydroxyphenyl tetramethylene S-HFPS, 3,5-dimethoxy-4-hydroxyphenyl tetramethylene S-HFPS, 4-methoxyphenyl tetramethylene S-HFPS, 4-t-butyloxycarbonyloxyphenyl tetramethylene S-HFPS, 4-t-butyloxycarbonylphenyl tetramethylene S-HFPS, 4-t-butyloxycarbonylmethylenoxyphenyl tetramethylene S-HFPS, 4-phenylthiophenyl tetramethylene S-HFPS, 2-naphthyl tetramethylene S-HFPS, 4-hydroxynaphthyl tetramethylene S-HFPS, 9-anthryl tetramethylene S-HFPS, phenyl pentamethylene S-HFPS, 4-methylphenyl pentamethylene S-HFPS, 4-t-butylphenyl pentamethylene S-HFPS, 4-t-butyloxyphenyl pentamethylene S-HFPS, 4-cyclohexylphenyl pentamethylene S-HFPS, 4-chlorophenyl pentamethylene S-HFPS, 4-N,N-dimethylaminophenyl pentamethylene S-HFPS, 4-hydroxyphenyl pentamethylene S-HFPS, 3,5-dimethyl-4-hydroxyphenyl pentamethylene S-HFPS, 3,5-dimethoxy-4-hydroxyphenyl pentamethylene S-HFPS, 4-methoxyphenyl pentamethylene S-HFPS, 4-t-butyloxycarbonyloxyphenyl pentamethylene S-HFPS, 4-t-butyloxycarbonylphenyl pentamethylene S-HFPS, 4-t-butyloxycarbonyl methylenoxyphenyl pentamethylene S-HFPS, 4-phenylthiophenyl pentamethylene S-HFPS, 2-naphthyl pentamethylene S-HFPS, 4-hydroxynaphthyl pentamethylene S-HFPS, 9-anthryl pentamethylene S-HFPS, phenylcarbonylmethylene dimethyl S-HFPS, phenylcarbonylmethylene tetramethylene S-HFPS, phenylcarbonylmethylene pentamethylene S-HFPS, 2-naphthylcarbonylmethylene dimethyl S-HFPS, 2-naphthylcarbonylmethylene tetramethylene S-HFPS, 2-napthylcarbonylmethylene pentamethylene S-HFPS, diphenyl I-HFPS, bis-(4-methylphenyl) I-HFPS, bis-(3,4-dimethylphenyl) I-HFPS, bis-(4-t-butylphenyl) I-HFPS, bis-(4-t-butyloxyphenyl) I-HFPS, bis-(4-cyclohexylphenyl) I-HFPS, bis-(4-trifluoromethylphenyl) I-HFPS, bis-(4-chlorophenyl) I-HFPS, bis-(2,4-dichlorophenyl) I-HFPS, bis-(4-dimethylaminophenyl) I-HFPS, bis-(4-hydroxyphenyl) I-HFPS, bis-(3,5-dimethyl-4-hydroxyphenyl) I-HFPS, bis-(4-methoxyphenyl) I-HFPS, bis-(4-t-butyloxycarbonyloxyphenyl) I-HFPS, bis-(4-t-butyloxycarbonylphenyl) I-HFPS, bis-(4-t-butyloxycarbonyl methylene oxyphenyl) I-HFPS, bis-(4-phenylthiophenyl) I-HFPS, bis-(3-methoxycarbonylphenyl) I-HFPS, bis-(2-naphthyl) I-HFPS, dithienyl thienyl 1-HFPS, 4-methylphenyl phenyl I-HFPS, 3,4-dimethylphenyl phenyl I-HFPS, 4-t-butylphenyl phenyl I-HFPS, 4-t-butyloxyphenyl phenyl I-HFPS, 4-cyclohexylphenyl phenyl I-HFPS, 4-trifluoromethylphenyl phenyl I-HFPS, 4-chlorophenyl phenyl I-HFPS, 2,4-dichlorophenyl phenyl I-HFPS, 4-dimethylaminophenyl phenyl I-HFPS, 4-hydroxyphenyl phenyl I-HFPS, 3,5-dimethyl-4-hydroxyphenyl phenyl I-HFPS, 4-methoxyphenyl phenyl I-HFPS, 4-t-butyloxycarbonyloxyphenyl phenyl I-HFPS, 4-t-butyloxycarbonylphenyl phenyl I-HFPS, 4-t-butyloxocarbonyl methyleneoxyphenyl phenyl I-HFPS, 4-phenylthiophenyl phenyl I-HFPS, 3-methoxycarbonylphenyl phenyl I-HFPS, 2-naphthyl phenyl I-HFPS, 9-anthryl phenyl I-HFPS, thienyl phenyl I-HFPS, and onium salts wherein S-HFPS of the above compounds have been replaced with sulfonium nonafluorobutane sulfonate, and onium salts wherein I-HFPS of the above compounds have been replaced with iodonium fluorobutane sulfonate.

The onium salt precursor, which generates a fluorinated alkanesulfonic acid, may be synthesized by various processes. For example, the sulfonium salt may be synthesized by a process described in Y. Endo, K. Shudo, and T. Okamato, Chem. Pharm Bull., 29, 3753–3755 (1981), and by the same process described in a synthesis example described in J. V. Crivello and J. H. W. Lam, Macromolecules, 10, 1307–1315 (1977).

The onium salt precursors, which generate fluorinated alkanesulfonic acids, may be contained alone or as a mixture of two or more in the composition according to the present invention.

According to the composition of the present invention, the amount of the onium salt precursor added, which generates a fluorinated alkanesulfonic acid, may be properly determined in such an amount range as will provide the effect of the onium salt pecursor. In the case of the positive-working chemically amplified radiation sensitive composition, the amount of the onium salt precursor added is preferably about 0.1 to 30 parts by weight, more preferably about 0.5 to 15 parts by weight, based on 100 parts by weight of the film forming hydroxystyrene based resin present in the composition. On the other hand, in the case of the negative-working chemically amplified radiation sensitive composition, the amount of the onium salt precursor added is preferably about 0.1 to 30 parts by weight, more preferably about 0.5 to 15 parts by weight, based on 100 parts by weight of the film forming hydroxystyrene based resin present in the composition.

If required, the onium salts precursor of the present invention, which generate fluorinated alkanesulfonic acids, may be used in combination with other PAGs. Preferable PAGs are those which can maintain high transparency of the (a) positive-working or (b) negative-working chemically amplified radiation sensitive composition at the irradiation wavelength, particularly near 365 nm, 248 nm, or 193 nm. As a general feature, suitable additional PAGs should produce acids, preferably sulfonic acids, which have a boiling point above 150° C. Examples of preferred PAGs include various anionic sulfonium salts or iodonium salts. Examples thereof include sulfonium or iodonium camphor sulfonates, sulfonium or iodonium 2,4-dimethylbenzenesulfonates, sulfonium or iodonium toluenesulfonates, sulfonium or iodonium pentafluorobenzenesulfonates, 1-anthrylsulfonates, or 9,10-dimethoxyanthrylsulfonates. Especially preferred are the sulfonium or iodonium 2-acrylamido-2-methyl-1-propanesulfonates. Other examples of preferred ionic PAGs include the respective diazonium salts, ammonium salts, phosphonium salts, selenonium salts, or arsonium salts. Examples of preferred nonionic PAGs include o-nitrobenzyl sulfonates, aryl sulfonates, bis-[(2,2,2-trifluoro-1-alkylsulfonyloxy)-1-trifluoromethylethyl]-benzenes, bis-[(2,2,2-trifluoro-1-arylsulfonyloxy)-1-trifluoromethylethyl]-benzenes, α, α-bis-(arylsulfonyl)diazomethanes, α, α-bis-(alkylsulfonyl)diazomethanes, α, α-bis-(arylsulfonyl)methanes, diarylsulfones, α-arylcarbonyl-α-arylsulfonyldiazomethanes, α-arylcarbonyl-α-arylsulfonylmethanes, α-hydroxymethyl benzoin sulfonates, oximesulfonates, iminosulfonates, and N-sulfonyloxy pyridones. Especially preferred is the combination of the onium salts of the present invention with α, α-bis-(arylsulfonyl)diazomethanes or α, α-bis-(alkylsulfonyl)diazomethanes as non-ionic PAGs.

(b) Film Forming Hydroxystyrene Based Resin

The composition according to the present invention comprises a film forming hydroxystyrene based resin. The film forming hydroxystyrene based resin refers to a polymer of 4-hydroxystyrene, 3-hydroxystyrene, or 2-hydroxystryene, or a co-, ter-, quater- or pentapolymer of the styrenes and other monomers. As described below, different modifications or properties are required of the film forming hydroxystyrene based resin depending upon whether the chemically amplified radiation sensitive composition is of positive-working type or negative-working type.

(i) Where Chemically Amplified Radiation Sensitive Composition is of Positive-working Type When the chemically amplified radiation sensitive composition of the present invention is of positive-working type, the film forming hydroxystyrene based resin is made alkali insoluble by protecting alkali soluble groups on the resin with an acid cleavable protective group. According to a preferred embodiment of the present invention, the hydroxystyrene based resin has multiple acid cleavable (preferably pendant) C—O—C or C—O—Si groups and is made alkali insoluble by protecting alkali soluble groups on the resin by the acid cleavable protective groups.

According to a preferred embodiment of the present invention, the hydroxystyrene based resin has a molecular weight in the range of 2,000 to about 100,000 with the polydispersity being in the range of 1.01 to 2.99, more preferably a molecular weight in the range of 2,000 to 20,000 with the polydispersity being not more than 2.20.

According to a preferred embodiment of the present invention, the transmission per micrometer film thickness of the hydroxystyrene based resin is generally better than 50% at irradiation wave length. The solubility of the base resin, not protected by acid cleavable groups, in a standard aqueous alkaline developer solution (2.38% tetramethylammonium hydroxide) at 21° C. is preferably above 5,000 angstrom/min, more preferably above 10,000 angstrom/min. On the other hand, the hydroxystyrene based resin protected by acid cleavable groups has virtually no solubility. That is, the solubility thereof in the same standard aqueous alkaline developer solution is preferably less than 800 angstrom/min, more preferably less than 400 angstrom/min.

According to the composition of the present invention, the base skeleton of the hydroxystyrene based resin is not particularly limited and may be properly determined by taking into consideration applications of the composition, radiation wavelength for exposure, production conditions, chemical composition and the like. According to a preferred embodiment of the present invention, examples of hydroxystyrene based resins usable herein include: poly-(4-hydroxystyrene); poly-(3-hydroxystyrene); poly-(2-hydroxystyrene); and copolymers of 4-, 3-, or 2-hydroxystyrene with other monomers, particularly bipolymers and terpolymers. Examples of other monomers usable herein include 4-, 3-, or 2-acetoxystyrene, 4-, 3-, or 2-alkoxystyrene, styrene, α-methylstyrene, 4-, 3-, or 2-alkylstyrene, 3-alkyl-4-hydroxystyrene, 3,5-dialkyl-4-hydroxystyrene, 4-, 3-, or 2-chlorostyrene, 3-chloro-4-hydroxystyrene, 3,5-dichloro-4-hydroxystyrene, 3-bromo-4-hydroxystyrene, 3,5-dibromo-4-hydroxystyrene, vinylbenzyl chloride, 2-vinylnaphthalene, vinylanthracene, vinylanilline, vinylbenzoic acid, vinylbenzoic acid esters, N-vinylpyrrolidone, 1-vinylimidazole, 4-, or 2-vinylpyridine, 1-vinyl-2-pyrrolidinone, N-vinyl lactam, 9-vinylcarbazole, vinyl benzoate, acrylic acid and its derivatives, i.e. methyl acrylate and its derivatives, acrylamide and its derivatives, methacrylic acid and its derivatives, i.e. methyl methacrylate and its derivatives, methacrylamide and its derivatives, acrylonitrile, methacrylonitrile, 4-vinyl benzoic acid and its derivatives, i.e. 4-vinyl benzoic acid esters, 4-vinylphenoxy acetic acid and its derivatives, i.e. 4-vinylphenoxy acetic acid esters, maleimide and its derivatives, N-hydroxymaleimide and its derivatives, maleic anhydride, maleic/fumaric acid and their derivatives, i.e. maleic/fumaric acid ester, vinyltrimethylsilane, vinyltrimethoxysilane, or vinylnorbornene and its derivatives. Another examples of preferred other monomers usable herein include isopropenylphenol, propenylphenol, poly-(4-hydroxyphenyl) (meth)acrylate, poly-(3-hydroxyphenyl) (meth)acrylate, poly-(2-hydroxyphenyl) (meth)acrylate, N-(4-hydroxyphenyl) (meth)acrylamide, N-(3-hydroxyphenyl) (meth)acrylamide, N-(2-hydroxyphenyl) (meth)acrylamide, N-(4-hydroxybenzyl) (meth)acrylamide, N-(3-hydroxybenzyl) (meth)acrylamide, N-(2-hydroxybenzyl) (meth)acrylamide, 3-(2-hydroxyhexafluoropropyl-2)-styrene, and 4-(2-hydroxyhexafluoropropyl-2)-styrene.

As described above, when the chemically amplified radiation sensitive composition is of positive-working type, the hydroxystyrene based resin is made alkali insoluble by protecting alkali soluble groups on the resin with an acid cleavable protective group. The introduction of the protective group may be carried out by an proper method depending upon alkali soluble groups on the resin, and could be easily carried out by a person having ordinary skill in the art.

For example, when the alkali soluble group on the resin is a phenolic hydroxyl group, the phenolic hydroxyl groups present in the resin are partly or fully protected by an acid labile protective group, preferably by one or more protective groups which form acid cleavable C—O—C or C—O—Si bonds. Examples of protective groups usable herein include acetal or ketal groups formed from alkyl or cycloalkyl vinyl ethers, silyl ethers formed from suitable trimethylsilyl or t-butyl(dimethyl)silyl precursors, alkyl ethers formed from methoxymethyl, methoxyethoxymethyl, cyclopropylmethyl, cyclohexyl, t-butyl, amyl, 4-methoxybenzyl, o-nitrobenzyl, or 9-anthrylmethyl precursors, t-butyl carbonates formed from t-butoxycarbonyl precursors, and carboxylates formed from t-butyl acetate precursors.

When the alkali soluble group on the resin is a carboxyl group, the carboxyl groups present on the resin are partly or fully protected by an acid labile protective group, preferably by one or more protective groups which form acid cleavable C—O—C or C—O—Si bonds. Examples of protective groups usable herein include alkyl or cycloalkyl vinyl ethers and esters formed from precursors containing methyl, methyloxymethyl, methoxyethoxymethyl, benzyloxymethyl, phenacyl, N-phthalimidomethyl, methylthiomethyl, t-butyl, amyl, cyclopentyl, 1-methylcyclopentyl, cyclohexyl, 1-methylcyclohexyl, 2-oxocyclohexyl, mevalonyl, diphenylmethyl, α-methylbenzyl, o-nitrobenzyl, p-methoxybenzyl, 2,6-dimethoxybenzyl, piperonyl, anthrylmethyl, triphenylmethyl, 2-methyladamantyl, tetrahydropyranyl, tetrahydrofuranyl, 2-alkyl-1,3-oxazolinyl, dibenzosuberyl, trimethylsilyl, or t-butyldimethylsilyl group.

According to the present invention, the above resins may be used alone or as a mixture of two or more.

The hydroxystyrene based resin is especially useful for exposure with i-line (365 nm) or DUV (248 nm) radiation, e-beam, ion beam or x-rays.

According to a preferred embodiment of the present invention, some of the PAGs (photoacid generators) described above are especially suitable for exposure with VDUV (193 nm) radiation, as they exhibit excellent absorption characteristics at this specific wavelength.

Examples of hydroxystyrene based resins suitable for VDUV (193 nm) applications include co- or terpolymers of (meth)acrylates with acid-cleavable protective groups and methyl (meth)acrylate, isobornyl (meth)acrylate, adamantyl (meth)acrylate, norbornyl (meth)acrylate, tricyclo [5.2.1.0.$^{2.6}$]decanyl (meth)acrylate, or menthyl (meth)acrylate, co- or terpolymers of maleic acid anhydride with norbornene, 5,6-dihydrodicyclopentadiene, or 1,5-cyclooctadiene derivatives as disclosed in EP 794,458A1, or copolymers with polyalkylcyclic compounds, such as 8-methyl-8-carboxy tetracyclo[4.4.0.1.$^{2.5}$.1.$^{7.10}$]dodecene, 8-methyl-8-methoxycarbonyl tetracyclo[4.4.0.1.$^{2.5}$.1.$^{7.10}$] dodecene, 5-methyl-5-methoxycarbonyl bicyclo[2.2.1] hept-2-ene, or 8,9-dicarboxylic anhydride tetracyclo [4.4.0.1.$^{2.5}$.1.$^{7.10}$] dodec-3-ene as disclosed in EP 789, 278A2 and WO 97/33,198.

According to a preferred embodiment of the present invention, when the positive-working radiation sensitive composition according to the present invention may contain a dissolution inhibitor. According to the present invention, the dissolution inhibitor per se is not an essential component of the composition which creates good lithographic performance. However, the dissolution inhibitor is often useful for improving specific properties of the positive-working radiation sensitive composition.

Examples of preferred dissolution inhibitors usable herein include polymer, oligomer, or monomer compounds having at least one acid cleavable C—O—C or C—O—Si groups. According to the present invention, oligomers or low-molecular weight compounds having a molecular weight of not more than 3,500, particularly not more than 1,000, are preferred. More specific examples of dissolution inhibitors usable herein include monomer or oligomer compounds having 1 to 10 phenolic hydroxyl groups which are partly or fully protected by a protective group having acid cleavable C—O—C or C—O—Si bonds. Protective groups, which provide such bonds, include acetal or ketal formed from aliphatic or alicyclic vinyl ether, silyl ethers formed from suitable trimethylsilyl or t-butyl(dimethyl)silyl precursors, alkyl ethers formed from methoxymethyl, methoxyethoxymethyl, cyclopropylmethyl, cyclohexyl, t-butyl, amyl, 4-methoxybenzyl, o-nitrobenzyl, or 9-anthrylmethyl precursors, t-butyl carbonates formed from t-butoxycarbonyl precursors, and t-butyl or related phenoxy-acetates formed from t-butyl or related acetate precursors. Further specific examples of dissolution inhibitors usable herein include monomer or oligomer compounds having 1 to 6 carboxyl groups which are partly or fully protected by a protective group having an acid cleavable C—O—C or C—O—Si bonds. Protective groups, which provide such bonds, include aliphatic or cycloaliphatic vinyl ethers and esters formed from precursors containing methyl, methyloxymethyl, methoxyethoxymethyl, benzyloxymethyl, phenacyl, N-phthalimidomethyl, methylthiomethyl, t-butyl, amyl, cyclopentyl, 1-methylcyclopentyl, cyclohexyl, 1-methylcyclohexyl, 2-oxocyclohexyl, mevalonyl, diphenylmethyl, α-methylbenzyl, o-nitrobenzyl, p-methoxybenzyl, 2,6-dimethylbenzyl, piperonyl, anthrylmethyl, triphenylmethyl, 2-methyladamantyl, tetrahydropyranyl, tetrahydrofuranyl, 2-alkyl-1,3-oxazolinyl, dibenzosuberyl, trimethylsilyl, or t-butyldimethylsilyl group.

Further examples of preferred dissolution inhibitors include the following compounds:

1. those having at least one orthocarboxylate or orthocarboxyamide-acetal groups, with the option to be polymeric in nature and for the said groups to appear as linking elements in the main chain or as side-chain substituents (DE 2,3610,842 and DE 2,928,636);

2. oligomeric or polymeric compounds having recurring acetal or ketal groups in the main chain (DE 2,306,248 and DE 2,718,254);

3. compounds having at least one enol ether or N-acyliminocarbonate group (EP 0,006,626 and 0,006,627);

4. cyclic acetals or ketals of b-ketoesters or -amides (EP 0,202,196);

5. compounds having silyl ether groups (DE 3,544,165 and DE 3,601,264);

6. compounds having silyl enol ether groups (DE 3,730, 785 and DE 3,730,783);

7. monoacetals or monoketals whose aldehyde or keto component has a solubility in the developer between 0.1 and 100 g/l (DE 3,730,787);

8. oligomer or polymer N,O-acetals (U.S. Pat No. 5,286, 602);

9. monomer or polymer acetals with t-butyloxycarbonyl groups (U.S. Pat. No. 5,356,752 and U.S. Pat. No. 5,354, 643); and 10. monomer or polymer acetals with sulfonyloxy groups (U.S. Pat. No. 5,346,804 and U.S. Pat. No. 5,346,806).

These dissolution inhibitors may be added alone or as a mixture of two or more to the composition.

(ii) Where Chemically Amplified Radiation Sensitive Composition is of Negative-working Type When the radiation sensitive composition of the present invention is of positive-working type, the composition comprises an photoacid generator, a film forming alkali soluble hydroxystyrene based resin, and, in addition, optionally an acid-sensitive crosslinking agent. Specifically, when the resin is an acid-sensitive self-crosslinkable resin, the crosslinking agent is unnecessary. On the other hand, when the resin is not self-crosslinkable, the composition according to the present invention further comprises an acid-sensitive crosslinking agent.

According to a preferred embodiment of the present invention, in the negative-working radiation sensitive composition, the hydroxystyrene based resin has a molecular weight in the range of 2,000 to about 100,000 with the polydispersity being in the range of 1.01 to 2.80, more preferably a molecular weight in the range of 2,000 to 20,000 with the polydispersity being not more than 2.20.

According to a preferred embodiment of the present invention, the transmission per micrometer film thickness of the hydroxystyrene based resin is better than 50% for light at irradiation wavelength. The solubility of the resin in a water-soluble standard alkaline developer solution (2.38% tetramethylammonium hydroxide) at 21° C. is preferably above 1,000 angstrom/min, more preferably above 3,000 angstrom/min. According to the composition of the present invention, the base skeleton of the hydroxystyrene based resin is not particularly limited and may be properly determined by taking into consideration applications of the composition, radiation wavelength for exposure, production conditions, chemical composition and the like. According to a preferred embodiment of the present invention, examples of hydroxystyrene based resins usable herein include: poly-(4-hydroxystyrene); poly-(3-hydroxystyrene); poly-(2-hydroxystyrene); and copolymers of 4-, 3-, or 2-hydroxystyrene with other monomers, particularly bipolymers and terpolymers. Examples of other monomers usable herein include 4-, 3-, or 2-acetoxystyrene, 4-, 3-, or 2-alkoxystyrene, styrene, α-methylstyrene, 4-, 3-, or 2-alkylstyrene, 3-alkyl-4-hydroxystyrene, 3,5-dialkyl-4-hydroxystyrene, 4-, 3-, or 2-chlorostyrene, 3-chloro-4-hydroxystyrene, 3,5-dichloro-4-hydroxystyrene, 3-bromo-4-hydroxystyrene, 3,5-dibromo-4-hydroxystyrene, vinylbenzyl chloride, 2-vinylnaphthalene, vinylanthracene, vinylanilline, vinylbenzoic acid, vinylbenzoic acid esters, N-vinylpyrrolidone, 1-vinylimidazole, 4-, or 2-vinylpyridine, 1-vinyl-2-pyrrolidinone, N-vinyl lactam, 9-vinylcarbazole, vinylbenzoate, acrylic acid and its derivatives, i.e. methyl acrylate and its derivatives, glycidyl acrylate, acrylamide and its derivatives, methacrylic acid and its derivatives, i.e. methyl methacrylate and its derivatives, glycidyl methacrylate, capped 2-isocyanate ethyl methacrylate, methacrylamide and its derivatives, acrylonitrile, methacrylonitrile, 4-vinyl benzoic acid and its derivatives, i.e. 4-vinyl benzoic acid esters, 4-vinylphenoxy acetic acid and its derivatives, i.e. 4-vinylphenoxy acetic acid esters, maleimide and its derivatives, N-hydroxymaleimide and its derivatives, maleic anhydride, maleic acid and fumaric acid and their derivatives, i.e. maleic acid esters and fumaric acid esters, vinyltrimethylsilane, vinyltrimethoxysilane, or vinylnorbornene and its derivatives. Another examples of preferred other monomers usable herein include isopropenylphenol, propenylphenol, poly-(4-hydroxyphenyl) (meth)acrylate, poly-(3-hydroxyphenyl) (meth)acrylate, poly-(2-hydroxyphenyl) (meth)acrylate, N-(4-hydroxyphenyl) (meth)acrylamide, N-(3-hydroxyphenyl) (meth)acrylamide, N-(2-hydroxyphenyl) (meth)acrylamide, N-(4-hydroxybenzyl) (meth)acrylamide, N-(3-hydroxybenzyl) (meth)acrylamide, N-(2-hydroxybenzyl) (meth)acrylamide, 3-(2-hydroxyhexafluoropropyl-2)-styrene, and 4-(2-hydroxyhexafluoropropyl-2)-styrene.

According to the chemically amplified radiation sensitive composition of the present invention, the resin is either acid-sensitive self-crosslinkable or non-self-crosslinkable. In the former, at least one acid-sensitive functional group is present in the resin. This acid sensitive group crosslinks the film forming alkali soluble hydroxystyrene based resin molecule through an acid generated from the photoacid generator to render the resin alkali insoluble. On the other hand, the latter requires the presence of a crosslinking agent. This crosslinking agent crosslinks the film forming alkali soluble hydroxystyrene based resin through an acid generated from the photoacid generator to render the resin alkali insoluble. According to the present invention, the film forming hydroxystyrene based resin per se is not self-crosslinkable. However, at least one crosslinking portion of the crosslinking agent may be introduced into the resin to render the resin self-crosslinkable.

According to a preferred embodiment of the present invention, examples of crosslinking agents usable herein include oligomers or monomers having at least two crosslinking portions. Various crosslinking agents of this type are known in the art, and the crosslinking agent may be properly selected by taking various conditions into consideration. Preferably, however, the crosslinking agent is selected based on radiation wavelength for exposure. For example, resols are not very useful crosslinkers for DUV irradiation due to their high inherent absorption at this wavelength, but they may be employed when conventional NUV illumination systems are used.

Examples of preferred crosslinking agents usable herein include monomeric and oligomeric melamines/formaldehyde and urea/formaldehyde condensates as described in EP-A 133,216, DE-A 36 34 371 and DE 37 11 264. More preferred crosslinking agents are urea/formaldehyde derivatives which contain two to four N-hydroxymethyl, N-alkoxymethyl, or N-acyloxymethyl groups. In particular, the N-alkoxymethyl derivatives are suitable for use in the negative-working chemically amplified radiation sensitive composition of the present invention. Urea derivatives with four N-alkoxymethyl groups are especially preferred because they provide better shelf life stability of the chemically amplified negative-working radiation sensitive composition than derivatives with a smaller number of alkoxymethyl groups. The nature of the alkyl group in these derivatives is not particularly critical in this connection, however, methoxymethyl groups are preferred. The urea/formaldehyde compound may contain in addition to the methoxymethyl groups ethoxymethyl, propoxymethyl, or butoxymethyl groups or mixtures thereof. Also preferred are urea/formaldehyde derivatives which contain two to six N-hydroxymethyl, N-alkoxymethyl, or N-acyloxymethyl groups. Melamine derivatives which contain on average at least three, in particular at least 3.5 alkoxymethyl groups are preferred because they provide better shelf life stability of the negative-working chemically amplified radiation sensitive composition than derivatives with a smaller number of hydroxymethyl groups. The nature of the alkyl group in these derivatives is not particularly critical in this connection, however, methoxymethyl groups are preferred. The melamine/formaldehyde compound may contain, in addition to the methoxymethyl groups, ethoxymethyl, propoxymethyl, or butoxymethyl groups or mixtures thereof. Mixtures of urea/formaldehyde compound and melamine/formaldehyde compound are particularly preferred. Before their use as crosslinking agents in negative-working chemically amplified radiation sensitive compositions, the above condensation products should be purified by recrystallization or distillation and any water present should be removed because traces of water have a negative impact on the shelf life stability of the negative-working chemically amplified radiation sensitive composition. Various melamine and urea resins are commercially available. Here reference is made to the products Cymel® (Mitsui Cytec), Nicalacs® (Sanwa Chemical Co.), Plastopal® (BASF AG), or Maprenal® (Clariant GmbH).

Other suitable crosslinking agents are the resols disclosed in GB 2,082,339. Commercially available products include Bakelite® R, or Kelrez®. Also useful are the crosslinking agents disclosed in EP 212 482, such as aromatic hydrocarbons containing two or three alkoxymethyl, hydroxymethyl or acyloxymethyl groups. Other crosslinking materials include di- or trifunctional carbonyl aldehydes and ketones, acetals, enolethers, vinylethers, vinylesters, acrylates, methacrylates, epoxides, or divinylstyrene.

When the crosslinking agents is introduced into the resin to render the resin self-crosslinkable, examples of crosslinking agents usable for this purpose include copolymers with (meth)acrylmethoxymethylamide, (meth)acrylvinyl-, -alkenyl-, -allyl-, or alkynyl esters, glycidyl (meth)acrylate or reaction products of 2-isocyanatoethyl methacrylate with unsaturated alcohols or amines.

(c) Other Additives

Both the positive-working chemically amplified radiation sensitive composition and the negative-working chemical amplified radiation sensitive composition according to the present invention may further contain other performance improving additives such as dyes to adjust the material absorption, plasticizers to reduce the brittleness of the material film and to optimize the adhesion on the substrate, surfactants to improve the material film uniformity, sensitizers to amplify the quantum yield of the PAG, photospeed enhancers to increase the photosensitivity, solubility modulators to improve the contrast, thermal radical generators to improve the film hardness upon a hardbake, and basic or acidic latent image stabilizers to improve the material stability during its processing. Suitable dyes include e.g. aromatic diazoketone derivatives, such as 9-diazo-10-phenanthrone, 1-diazo-2-tetralone, o-napthoquinone diazido-4-sulfonic acid esters, or o-naphthoquinone diazido-5-sulfonic esters, benzophenone dervatives, such as 2,3,4-trihydroxy benzophenone, or 2,2',4,4'-tetrahydroxy benzophenone, naphthalene, anthracene or phenanthrene derivatives, such as 9-(2-methoxyethoxy)methylanthracene.

Suitable plasticizers include e.g. terephthalic acid esters, such as dioctyl terephthalate, or poly glycols, such as polyethylene glycol.

Suitable surfactants include nonionic surfactants, such as polyglycols and their derivatives, i.e. polypropylene glycol, or polyoxyethylene laurylether, fluorine containing surfactants, such as Fluorad™ (available from Sumitomo 3M, Ltd.), Megafac ™ (available from Dainippon Ink & Chemicals, Inc.), Surflon™ (available from Asaki Glass Co., Ltd.), or organosiloxane surfactants, such as KP341 (available from ShinEtsu Chemical Co., Ltd.).

Suitable sensitizers include e.g. thioxanthone, coumarin, or phenanthrene derivatives.

Photospeed enhancers include e.g. polyphenol or benzotriazole derivatives, such as resorcinol, catechol, or bisphenol A.

Solubility modulators include difunctional vinyl ethers, such as 2,2'-bis(vinyloxyethoxyphenyl)propane or tris (vinyloxyethoxyphenyl)ethane, difunctional (meth) acrylates, such as ethylene glycol di(meth)acrylate.

Thermal radical generators include peroxides, such as t-butyl perbenzoate, or dicumyl peroxide, or azo-compounds having a scorch temperature above 100° C.

Basic latent image stabilizers include amines, such as tribenzylamine, dicyclohexylamine, or triethanolamine, nitrogen containing heterocycles, such as lutidine, dimethylaminopyridine, pyrimidine, ammonium compounds, such as tetramethyl ammonium hydroxide, tetrabutyl ammonium hydroxide or tetramethyl ammonium lactate, or nitrogen containing polymers, such as polyvinylpyridine, or polyvinylpyridine-co-methylmethacrylate.

Of special interest as latent image stabilizers are sulfonium derivatives, such as triphenyl sulfonium hydroxide, triphenyl sulfonium acetate, or triphenyl sulfonium lactate. Acidic latent image stabilizers include e.g. salicylic acid, Sax ™ (polysalicylic acid derivatives available from Mitsui Chemical K.K.), 4-dimethylamino benzoic acid or ascorbic acid. Although the amount of these additives added may be appropriately determined, it is preferably about 0.0001 to 10 parts by weight based on unit weight of the chemically amplified radiation sensitive composition. According to the most preferred embodiment of the present invention, the positive-working chemically amplified radiation sensitive composition comprises (1) 0.1 to 30 parts by weight of the sulfonium or iodonium salt of a fluorinated alkanesulfonic acid represented by formula (I), (2) 100 parts by weight of the film forming hydroxystyrene based resin having multiple acid cleavable C—O—C or C—O—Si bonds, (3) 0 to 50 parts by weight of the dissolution inhibitor having at least one acid cleavable C—O—C or C—O—Si bond; and (4) 0.01 to 5.0 parts by weight of the performance improving additive.

Further, the negative-working chemically amplified radiation sensitive composition comprises (1) 0.1 to 30 parts by weight of the sulfonium or iodonium salt of a fluorinated alkanesulfonic acid represented by formula (I).

(2) 100 parts by weight of the hydroxystyrene based resin, (3) 3 to 70 parts by weight of the acid-sensitive crosslinking agent, and (4) 0.01 to 5.0 parts by weight of the performance improving additive.

Use of the Composition of the Present Invention/radiation Sensitive Recording Medium and Production Process Thereof The chemically amplified radiation sensitive composition according to the present invention is used as the so-called "photoresist" in applications where the composition is coated on various substrates, and the coated substrates are exposed to render latent images alkali soluble or alkali insoluble, followed by rinsing with an alkali to form predetermined patterns on the substrates.

Thus, according to one aspect of the present invention, there is provided a radiation sensitive recording medium comprising: a substrate; and a radiation sensitive layer provided on the substrate, the radiation sensitive layer comprising the composition according to the present invention.

The composition according to the present invention may be coated, either as such or after dissolution in various solvents, onto the substrate. Examples of preferred solvents include ethylene glycol and propylene glycol and the monoalkyl and dialkyl ethers derived therefrom, especially the monomethyl and dimethyl ethers and the monoethyl and diethyl ethers, esters derived from aliphatic $(C_1-C_6)$ carboxylic acids and either $(C_1-C_8)$-alkanols or $(C_1-C_8)$-alkandiols or $(C_1-C_6)$-alkoxy-$(C_1-C_8)$-alkanols, such as ethyl acetate, hydroxyethyl acetate, alkoxyethyl acetate, n-butyl acetate, amyl acetate, propylene glycol monoalkyl ether acetate, especially propylene glycol monomethyl ether acetate, propylene glycol monomethyl ether, ethyl lactate, ethyl pyruvate, ethers such as tetrahydrofuran and dioxane, ketones such as methyl ethyl ketone, methyl isobutyl ketone, methyl amyl ketone, cyclopentanone, and cyclohexanone, N,N-dialkylcarboxyamides such as N,N-dimethylformamide and N,N-dimethylacetamide, and also 1-methyl-pyrrolidin-2-one and butyrolactone as well as any desired mixture thereof. Among them, the glycol ethers, aliphatic esters and ketones are preferred.

Ultimately, the selection of the solvent or solvent mixture depends on the coating process used, on the desired layer thickness and on the drying conditions. The solid content of the solution is preferably about 5–60% solids, particularly about 10–50% solids.

The composition according to the present invention may be coated onto the substrate by any method without particular limitation, and the coating method may be properly selected by taking into consideration purposes and the like.

According to a preferred embodiment of the present invention, the chemically amplified radiation sensitive composition of the present invention is used as a photoresist material on a semiconductor substrate. Examples of substrates referred to herein include all those materials for production of capacitors, semiconductors, multi-layer printed circuits or integrated circuits. Specific mention should be made of silicon substrates, silicon oxide, silicon oxynitride, titanium nitride, tungsten nitride, tungsten silicide, aluminum, phosphor-spin-on glass, boron-phosphor-spin-on-glass, gallium arsenide, indium phosphide, and the like. In addition, these substrates may be coated with thin films of organic antireflective coatings consisting of organic polymers and a dye absorbing at the exposure wavelength. Furthermore, suitable substrates are those known from the production of liquid-crystal displays, such as glass or indium tin oxide, and also metal plates and sheets, as well as bimetallic or trimetallic sheets or electrically non-conducting which are coated with metals or paper. These substrates may be thermally pretreated, superficially roughened, incipiently etched or pretreated with chemicals to improve desired properties, such as increase of the hydrophilic nature, or to improve adhesion between the photoresist and the substrate. Preferably used adhesion promoters for silicon or silicon oxide substrates are adhesion promoters of the aminosilane type, such as hexamethyldisilazane, or 3-aminopropyltriethoxysilane.

The chemically amplified radiation sensitive composition according to the present invention may also be used as radiation sensitive coatings for the production of photochemical recording layers, such as printing plates for letterpress printing, including lithographic printing, screen printing and flexographic printing. Especially useful is their application as radiation sensitive coatings on aluminum plates, which have been surface grained, anodically oxidized and/or silicatized, and zinc or steel plates, which have optionally been chromium plated, and paper or plastic sheets.

Further, the chemically amplified radiation sensitive composition according to the present invention may be used in the manufacture of three dimensional microdevices, such as micro actuators, micro gears, and the like using fabrication techniques known to those skilled in the art, such as the LIGA process. The (a) positive-working or (b) negative-working chemically amplified radiation sensitive compositions according to the present invention is coated onto a substrate followed by drying to form a layer having a thickness of about 0.1 to 100 μm, preferably about 0.3 to 10 μm, depending upon applications. Thereafter, the coated substrate is exposed to actinic radiation. Suitable radiation sources are conventional broadband radiation sources, such as metal halide lamps, carbon arc lamps, xenon lamps and mercury vapor lamps, which may be filtered to yield narrow band emission, or excimer lasers, such as KrF excimer lasers, or ArF lasers, but also electron beams, ion beams, or x-rays. Particularly preferred are KrF excimer lasers, or ArF lasers emitting at 248 nm and 193 nm, respectively, and electron beams as well as x-rays.

Further, according to another aspect of the present invention, there is provided a process for producing a recording medium, comprising the steps of: dissolving the composition of the present invention in a solvent; coating the solution onto a substrate to form a radiation sensitive layer; and removing the solvent by evaporation.

According to this aspect of the present invention, the chemically amplified radiation sensitive composition may be coated onto the substrate by spray coating, flow coating, roller coating, spin coating, dip coating or the like. Thereafter, the solvent is removed by evaporation to leave the radiation sensitive layer as a film on the substrate. The removal of the solvent can be achieved by heating the film to about 150° C. Alternatively, a method may be used which comprises coating the radiation sensitive composition onto an intermediate substrate material by the above method and then transferring the coating onto a contemplated substrate by pressure, heat or a combination of pressure with heat. All materials suitable as substrate materials may be used as materials for the intermediate substrate. Thereafter, the layer thus formed is exposed image by image. After the exposure, the layer is heated at 60 to 150° C. for 30 to 300 sec in order to sensitize the latent image.

The layer is then treated with a developer. In the development, in the case of the positive-working radiation sensitive composition, the exposed regions are dissolved and removed, while, in the case of the negative-working radiation sensitive composition, the unexposed regions are dissolved and removed. As a result, images of the master, which has been exposed image by image, are left on the substrate. The heating of the layer before the development step increases the sensitivity of the recording material according to the present invention and is essential to produce extremely fine patterns. If the heating step is carried out at temperatures which are too low, adequate sensitivity of the material is not achieved, or, depending on the activation energy of the chemically amplified reaction, complete failure of the image formation may be observed. If the selected temperature is too high, impairment of the resolving power may result.

Suitable developers are aqueous solutions which contain hydroxides, particularly hydroxides of tetraalkyl ammonium ions, such as tetramethyl ammonium hydroxide. Other developers include the aqueous solutions containing aliphatic amines, or N-containing heterocycles, or silicates, metasilicates, hydrogenphosphates, and dihydrogenphosphates, carbonates or hydrogen carbonates of alkali metals, alkaline earth and/or ammonium ions, and also ammonia and the like. Developers free of metals useful for microelectronic device manufacturing are described in U.S. Pat. No. 4,141,733, U.S. Pat. No. 4,628,023, or U.S. Pat. No. 4,729,941, or EP-A 23,758, EP-A 62,733 and EP-A 97,282, and these developers may also be used. The content of these substances in the developer solution is in general about 0.1 to 15% by weight, preferably about 0.5 to 5% by weight, based on the weight of the developer solution. Developers which are free of metals are preferably used. Small amounts of a wetting agent may be added to the developer in order to facilitate the stripping of the soluble portions of the recording layer.

EXAMPLES

The present invention will be described in more detail with reference to the following examples, though it is not limited to these examples only.

Synthesis Example 101

Preparation of diphenyl 4-t-butylphenyl 3,3,3,2,1,1-hexafluoropropane sulfonate (PAG 101)

A column having a length of 55 cm and an inner diameter of 5 cm was packed with 700 g of Amberlyst A-26 (tradename) dispersed in methanol in its chloride form. 3,000 ml of methanol was added to 3,000 ml of a 54% aqueous solution of tetramethyl ammonium hydroxide. This alkali solution was used to convert the chloride form of the Amberlyst ion-exchange resin to its hydroxide form. The column was then washed with methanol until the solution withdrawn from the column became neutral.

39.93 g (0.1 mol) of diphenyl 4-t-butylphenyl bromide was dissolved in about 50 ml of methanol. The solution was passed through the column by elution with methanol at a rate of 30 ml/hour. The eluate was monitored using a potentiometer and occasionally tested for the absence of bromide ions using an aqueous silver nitrate solution. Next, the concentration of the hydroxyl group was determined by titration with 0.1N HCl. The yield of diphenyl 4-t-butylphenyl hydroxide was about 100%. The solution was adjusted to 1.0 mmol/g diphenyl 4-t-butylphenyl hydroxide. With stirring, to 500 g (50 mmol) of the diphenyl 4-t-butylphenyl hydroxide was added dropwise 10.45 g (50 mmol) of freshly 3,3,3,2,1,1-hexafluoropropane sulfonic acid diluted with 50 ml of methanol at room temperature. The mixture was stirred at room temperature for 24 hours. The solvent was removed by evaporation. The oil (27.5 g (about 100%)) thus obtained was crystallized to give pure diphenyl 4-t-butylphenyl 3,3,3,2,1,1-hexafluoropropane sulfonate.

The purity was measured by HPLC and found to be >99%.

$^1$H-NMR (CDCl$_3$): 1.44 (s, 9H,4-t-butyl), 5.23–5.41 (d[m], 1H, CHF), 7.62–7.78 ppm (m, 14H, aromatic).

Synthesis Example 102

Preparation of triphenyl sulfonium 3,3,3,2,1,1-hexafluoropropane sulfonate (PAG 102)

91.03 g (0.45 mol) of diphenyl sulfoxide was dissolved in 1300 ml of benzene in a 2-liter three-neck round-bottom flask equipped with a stirrer, a thermometer, a dropping funnel, a condenser, and a nitrogen inlet. The mixture was cooled to 4° C. with vigorous stirring. A solution of 189.0 g of (0.90 mol) trifluoroacetic anhydride and 104.4 g (0.45 mol) of 1,1,1,2,3,3-hexafluoropropane sulfonic acid was added dropwise thereto, while the temperature was maintained under ice cooling. After completion of the addition, the mixture was stirred for 1 hour. The temperature was returned room temperature, followed by stirring for additional 15 hours. After standing overnight, two separate phases were formed. The upper phase was removed and discarded. The oily bottom phase of approximately 500 ml volume was dropped into 2000 ml of diethyl ether, upon which a semi-crystalline deposit was formed. The ether was decanted, and the precipitate was dissolved in a minimum amount of dichloromethane. The solution was added dropwise to 1000 ml of vigorously stirred diethyl ether to reprecipitate the product. After completion of the addition, stirring was continued for 2 hours. After the solid was separated from diethyl ether, this procedure was repeated once more to enhance the crystallinity of the product. The mixture was filtered, and the semi-crystals were collected yielding 165.0 g of crude sulfonium salt. The melting point of the crude sulfonium salt was 104–109° C. Depending on the purity, the crystals can be either recrystallized from ethyl acetate or dissolved in the minimum amount of dichloromethane and purified by column chromatography on silica gel using a 95:5 dichloromethane-methanol mixture to perform purification. The first fractions containing unreacted diphenyl sulfoxide were discarded. After collection of the main fractions, the solvent was evaporated to leave 135.5 g (yield 60.9%) of triphenyl sulfonium 3,3,3,2,1,1-hexafluoropropane sulfonate as white crystals (m.p. 111–112° C.).

$^1$H-NMR (CDCl$_3$): δ=5.24–5.41 (d[m], 1H), 7.63–7.74 (m, 15H) ppm.

The purity was determined by HPLC analysis and found to be >97%.

Synthesis Example 103

Preparation of tris-(4-t-butylphenyl) sulfonium 3,3,3,2,1,1-hexafluoropropane sulfonate (PAG 103)

48.18 g (0.15 mol) of bis-(4-t-butylphenyl) sulfoxide (prepared from diphenyl sulfide and t-butyl bromide via FeCl$_3$ catalyzed alkylation and subsequent oxidation with 2-chlorobenzoic acid) was dissolved in 400 ml of 4-t-butylbenzene in a 1-liter three-neck round-bottom flask equipped with a stirrer, a thermometer, a dropping funnel, a condenser and a nitrogen inlet. The mixture was cooled to 4° C. with vigorous stirring. A solution of 63.0 g (0.30 mol) of trifluoroacetic anhydride and 34.8 g (0.15 mol) of 1,1,1,2,3,3-hexafluoropropane sulfonic acid was added dropwise thereto, while the temperature was maintained under ice cooling. After completion of the addition, the mixture was stirred for 1 hour. The temperature was returned to room temperature, followed by stirring for additional 15 hours. After standing overnight, two separate phases were formed. The upper phase was removed and discarded. The oily bottom phase of approximately 150 ml volume was diluted with 800 ml of diethyl ether, and washed twice with water and a sodium bicarbonate solution. The organic phase was dried over MgSO$_4$. After removal of the solvent, a semicrystalline solid was obtained. The semicrystalline solid was recrystallized from diethyl ether. Thus, white crystals of tris-(4-t-butylphenyl) sulfonium 3,3,3,2,1,1-hexafluoropropane sulfonate (42%) (m.p. 238–240° C.) was obtained.

$^1$H-NMR (CDCl$_3$): δ=1.34 (s, 27H), 5.32–5.53 (d[m], 1H), 7.62–7.65 (d, 6H), 7.68–7.71 (d, 6H) ppm.

The purity was determined by HPLC analysis and found to be >97%.

Synthesis Examples 104 to 108

The following sulfonium salts were prepared in substantially the same manner as in the above synthesis examples (PAGs 104–108).

Tris-(4-methylphenyl) sulfonium 3,3,3,2,1,1-hexafluoropropane sulfonate (PAG 104)

$^1$H-NMR (CDCl$_3$): δ=2.42 (s, 9H), 5.24–5.41 (d[m], 1H), 7.43–7.45 (d, 6H), 7.51–7.53(d, 6H) ppm.

The purity was determined by HPLC analysis and found to be >97%.

4-Methylphenyl-diphenyl sulfonium 3,3,3,2,1,1-hexafluoropropane sulfonate (PAG 105)

$^1$H-NMR (CDCl$_3$): δ=2.45 (s, 3H), 5.24–5.40 (d[m], 1H), 7.44–7.46 (d, 2H), 7.51–7.53 (d, 2H), 7.63–7.76 (m, 10H) ppm.

The purity was determined by HPLC analysis and found to be >97%.

Bis-(4-methylphenyl)phenyl sulfonium 3,3,3,2,1,1-hexafluoropropane sulfonate (PAG 106)

$^1$H-NMR (CDCl$_3$): δ=2.43 (s, 6H), 5.23–5.40 (d[m], 1H), 7.44–7.46 (d, 4H), 7.52–7.54 (d, 4H), 7.65–7.78 (m, 5H) ppm.

The purity was determined by HPLC analysis and found to be >97%.

Bis-(4-t-butylphenyl)phenyl sulfonium 3,3,3,2,1,1-hexafluoropropane sulfonate (PAG 107)

$^1$H-NMR (CDCl$_3$): δ=1.34 (s, 18H), 5.32–5.54 (d[m], 1H), 7.63–7.79 (m, 13H) ppm.

4-Cyclohexylphenyl-diphenyl sulfonium 3,3,3,2,1,1-hexafluoropropane sulfonate (PAG 108)

$^1$H-NMR (CDCl$_3$): δ=1.12–1.74 (m, 10H), 2.41–2.43 (m, 1H), 5.28–5.50 (d[m], 1H), 7.24–7.27 (d, 4H), 7.63–7.79 (m ,9H) ppm.

Synthesis Example 109

Preparation of tris-(4-butoxyphenyl) sulfonium 3,3,3,2,1,1-hexafluoropropane sulfonate (PAG 109)

To a stirred solution of 60.0 g (0.164 mol) of bis-(4-t-butoxyphenyl) sulfoxide in 26.8 g (0.34 mol) of pyridine and 400 ml of tetrahydrofuran was dropped 75.6 g (0.34 mol) of trimethylsilyl 3,3,3,2,1,1-hexafluoropropane sulfonate while keeping the temperature below −5° C. with a salted ice bath. After completion of the addition, the reaction temperature was raised to 5° C., followed by stirring for 20 minutes. A Grignard solution was prepared from 8.4 g (0.34 mol) of magnesium, 100 g of tetrahydrofuran and 68.6 g (0.38 mol) of 4-t-butoxy chlorobenzene, and added dropwise to the above solution at 0° C. The mixture was stirred for 2 hours at this temperature. Then water was added to decompose the excess Grignard reagent, and the inorganic salts were removed by filtration. The solution was concentrated to about 160 ml and extracted with a mixture of 1200 ml of dichloromethane, 600 g of a saturated aqueous solution of ammonium chloride and 600 ml water. The organic phase was washed twice with water and dried. The solvent was removed to yield an oily product which was then purified by column chromatography on silica gel using dichloromethane as the eluant. Thus, tris-(4-butoxyphenyl) sulfonium 3,3,3,2,1,1-hexafluoropropane sulfonate was obtained as a slightly yellowish powder (m.p. 107° C.). The structure was confirmed by $^1$H-NMR (CDCl$_3$) with $\delta$=1.42 (s, 27H), 5.14–5.52 (d[m], 1H), 7.17–7.20 (d, 6H) and 7.55–7.60 ppm (d, 6H).

Synthesis Example 110

Preparation of tris-(4-t-butoxycarbonylmethoxyphenyl) sulfonium 3,3,3,2,1,1-hexafluoropropane sulfonate (PAG 110)

A solution of 56.8 g (0.08 mol) of tris-(4-butoxyphenyl) sulfonium 3,3,3,2,1,1-hexafluoropropane sulfonate and 1.86 g (0.008 mol) of 3,3,3,2,1,1-hexafluoropropane sulfonic acid in 200 ml of ethanol was refluxed for 8 hours with stirring. After evaporation of the solvent, the obtained crude product of tris-(4-hydroxyphenyl) sulfonium 3,3,3,2,1,1-hexafluoropropane sulfonate (yield about 100%) was dissolved in 160 g of N,N-dimethylformamide and reacted with 55.4 g (0.40 mol) of anhydrous potassium carbonate and 60.3 g (0.40 mol) of t-butyl chloroacetate at 80° C. for 3 hours. The cooled reaction mixture was poured into 700 ml of water and extracted with dichloromethane. The organic phase was washed with water and dried. The solvent was removed. The oily residue was purified by column chromatography on silica gel using a dichloromethane and methanol as the eluent. The white product was collected to yield 31.8 g (yield 45%) of analytically pure tris-(4-t-butoxycarbonylmethoxyphenyl) sulfonium 3,3,3,2,1,1-hexafluoropropane sulfonate. The melting point of the product was 78° C. The $^1$H-NMR spectrum gave the following signals (CDCl$_3$): $\delta$=1.45 (s, 27H), 4.56 (s, 6H), 5.20–5.56 (d[m], 1H), 7.10–7.13 (d, 6H), 7.55–7.60 (d, 6H).

Synthesis Example 111

Preparation of β-oxocyclohexyl 2-norbornyl methyl sulfonium 3,3,3,2,1,1-hexafluoropropane sulfonate (PAG 111)

To a solution of 14.14 g (0.106 mol) of 2-chlorocyclohexane in 100 ml of ethanol was added dropwise 50 ml of a 15% solution of methylmercaptane sodium salt. The mixture was stirred for 3 hours. Then 600 ml water was added, and the mixture was extracted with dichloromethane. The organic phase was dried, and the solvent was removed to yield crude P-oxocyclohexyl methyl sulfide, which was purified by distillation (b.p. 45–47° C./0.3 mmHg). 2.0 g (15.6 mmol) of this product was dissolved in 10 ml of nitromethane and added dropwise with 20 g (114 mmol) of 2-bromonorbornane and stirred at room temperature for 1 hour. After that, a solution of 1.89 g (15.6 mmol) of silver 3,3,3,2,1,1-hexafluoropropane sulfonate dissolved in 400 ml of nitromethane was added dropwise to the reaction mixture and stirred for three hours at room temperature. The silver bromide was removed by filtration. The filtrate was concentrated to 50 ml, and then added dropwise to 600 ml of diethyl ether. The precipitated solid was collected, washed with ether and recrystallized from ethyl acetate. The yield of β-oxocyclohexyl 2-norbornyl methyl sulfonium 3,3,3,2,1,1-hexafluoropropane sulfonate was 1.67 g.

$^1$H-NMR (CDCl$_3$): $\delta$=1.33–2.28 (m, 16H), 2.30–3.10 (m, 5H), 3.65–3.77 (m, 1H), 4.95–5.53 ppm (2m, 2H).

Synthesis Example 112

Preparation of bis-(4-cyclohexylphenyl) iodonium 3,3,3,2,1,1-hexafluoropropane sulfonate (PAG 112)

A 500 ml three-neck round bottom flask equipped with a stirrer, a thermometer, a dropping funnel, a condenser, and a nitrogen inlet was charged with 43 g (0.20 mol) of potassium iodate, 69.2 g (0.43 mol) of cyclohexylbenzene and 43 ml acetic anhydride. The mixture was cooled to −5° C. A mixture of 43 ml of acetic anhydride and 30.1 ml concentrated sulfuric acid was added dropwise thereto with vigorous stirring. During the addition, the reaction temperature was kept below 5° C. After the end of the addition, the temperature of the reaction solution was returned to room temperature over a period of 2 to 3 hours. The resulting mixture was left for 48 hours and cooled to 5° C. 100 g of a 1:1 ice/water mixture was added with stirring. During this operation, the reaction temperature was kept below 10° C. Precipitated crystals of potassium salts were removed by filtration, and the mixture was extracted twice with petroleum ether. To the remaining aqueous solution was added dropwise 45 g of ammonium bromide dissolved in 100 ml water with stirring. The precipitate of bis-(4-cyclohexylbenzene)iodonium bromide was isolated by filtration, washed, and dried.

15.26 g (28.5 mmol) of the bromide was dissolved in 100 ml of dichloromethane and 7.3 g (34.2 mmol) of 1,1,1,2,3,3-hexafluoropropane sulfonic acid was added. The mixture was stirred at reflux for 6 hours. Hydrogen bromide evolved. After cooling, the reaction mixture was washed twice with a 2.5% aqueous solution of tetramethyl ammonium hydroxide and then dried. The solvent was then removed. The yellowish residue was recrystallized from an isopropanol/isopropyl ether mixture to give 12.2 g (63%) of bis-(4-cyclohexylphenyl) iodonium 3,3,3,2,1,1-hexafluoropropane sulfonate. This product had a melting point of 97° C.

$^1$H-NMR (CDCl$_3$): $\delta$=1.12–1.76 (m, 20H), 2.41–2.44 (m, 2H), 4.96–5.18 (m, 1H), 7.16–7.19 (d, 4H), 7.78–7.81 (d, 4H) ppm.

The purity was determined by HPLC analysis and found to be >97%.

Synthesis Examples 113–115

The following sulfonium salts were synthesized in substantially the same manner as in the above synthesis examples (PAGs 113–115).

Diphenyl iodonium 3,3,3,2,1,1-hexafluoropropane sulfonate (PAG 113)

$^1$H-NMR (CDCl$_3$): $\delta$=4.98–5.20 (d[m], 1H), 7.61–7.78 (m, 10H) ppm.

Bis-(4-methylphenyl) iodonium 3,3,3,2,1,1-hexafluoropropane sulfonate (PAG 114)

$^1$H-NMR (CDCl$_3$): $\delta$=2.42 (s, 18H), 4.96–5.18 (d[m], 1H), 7.41– 7.43 (d, 4H), 7.50–7.52 (d, 4H) ppm.

Bis-(4-t-butylphenyl) iodonium 3,3,3,2,1,1-hexafluoropropane sulfonate (PAG 115)

$^1$H-NMR (CDCl$_3$): δ=1.34 (s, 18H), 5.00–5.22 (d[m], H), 7.62–7.65 (d, 6H), 7.68–7.71 (d, 6H) ppm.

Synthesis Example 116

Preparation of 4-methylphenyl phenyl iodonium 3,3,3,2,1,1-hexafluoropropane sulfonate (PAG 116)

To a stirred suspension of 4.40 g (20 mmol) of iodosylbenzene in 100 ml of dichloromethane was added dropwise 4.64 g (20 mmol) of 3,3,3,2,1,1-hexafluoropropane sulfonic acid at 0° C. under exclusion of moisture. The mixture was stirred at room temperature for 2 hours. The temperature was returned to 0° C. again. 1.84 mg (20 mmol) of toluene was added dropwise. After the addition, stirring was continued at room temperature for additional 1 hour. The solvent was evaporated. The oily residue was dissolved in diethyl ether. After cooling, crystals of 4-methylphenyl phenyl iodonium 3,3,3,2,1,1-hexafluoropropane sulfonate were obtained. The crystals were washed with hexane.

The yield was 5.2 g.

$^1$H-NMR (CDCl$_3$): δ=2.43 (s, 3H), 4.98–5.18 (d[m], 1H), 7.42–7.44 (d, 2H), 7.52–7.54 (d, 2H), 7.61–7.78 (m, 5H) ppm.

Synthesis Example 117

Preparation of bis-(4-butoxyphenyl)phenyl sulfonium 3,3,3,2,1,1-hexafluoropropane sulfonate (PAG 117)

To a stirred solution of 60.0 g (0.174 mol) of bis-(4-t-butoxyphenyl) sulfoxide in 26.8 g (0.34 mol) of pyridine and 400 ml of tetrahydrofuran was dropped 75.6 g (0.34 mol) of trimethylsilyl 3,3,3,2,1,1-hexafluoropropane sulfonate while keeping the solution temperature below −5° C. with a salted (sodium chloride) ice bath. After completion of the addition, the reaction temperature was raised to 5° C., followed by stirring for 20 minutes. A Grignard reagent solution was prepared from 8.4 g (0.34 mol) of shaved magnesium, 100 g of tetrahydrofuran and 42.8 g (0.38 mol) of chlorobenzene, and added dropwise to the above solution at 0° C. The mixture was stirred for 2 hours at this temperature. Then water was added to decompose the excess Grignard reagent. The inorganic salts were removed by filtration. The solution was concentrated to about 160 ml and extracted with 1200 ml of dichloromethane, 600 g of a saturated solution of ammonium chloride and 600 ml of water. The organic phase was washed twice with water and dried. The solvent was removed to yield an oily product which was applied to column chromatography on silica gel using dichloromethane as the developing solvent. The corresponding fractions were combined and concentrated to obtain bis-(4-butoxyphenyl) phenyl sulfonium 3,3,3,2,1,1-hexafluoropropane sulfonate as a slightly yellowish powder (m.p. 102° C.). The structure was confirmed by $^1$H-NMR (CDCl3) with δ=1.42 (s, 18H), 5.32–5.54 (d[m], 1H), 7.20–7.23 (d, 4H), and 7.63–7.79 ppm (m, 9H).

Synthesis Example 118

Preparation of bis-(4-methylphenyl)4-cyclohexylphenyl sulfonium 3,3,3,2,1,1-hexafluoropropane sulfonate (PAG 118)

A mixture of 10.36 g (4.5 mmol) of ditolyl sulfoxide with 7.21 g (4.5 mmol) of 4-cyclohexylbenzene was placed in a 125 ml flask. Then 20 ml of a previously prepared phosphorus pentaoxide/metanesulfonic acid reagent (prepared by dissolving 36 g of phosphorus pentaoxide in 360 g of methanesulfonic acid) was added thereto while stirring with a magnetic stirrer. The mixture was heated to about 50° C. Thus, a dark brown solution was obtained. After the exothermic reaction ceased, the mixture was stirred at 45° C. for additional 3 hours. The temperature was then returned to room temperature, and the mixture was poured into 100 ml of water and 100 g of ice. The slightly suspended solution was filtered, followed by addition of 10.44 g (4.5 mmol) of 3,3,3,2,1,1-hexafluoropropane sulfonic acid to yield a white oil. The oil was stirred for 1 hour, and 200 ml of ethyl acetate was added thereto. The mixture was extracted. The organic phase was washed several times with water, and then dried. The solvent was removed by distillation. The oily residue was recrystallized from ethyl acetate and diethyl ether to give 11.5 g of the contemplated material. The structure was confirmed by $^1$H-NMR (CDCl$_3$) with δ=1.08–1.74 (m, 10H), 2.41–2.43 (m, 7H), 5.27–5.48 (d[m], 1H), 7.16–7.19 (d, 2H), 7.43–7.46 (d, 4H), 7.50–7.53 (d, 4H), and 7.78–7.80 ppm (d, 2H).

The purity was determined by HPLC analysis and found to be >97%.

Synthesis Example 119

Preparation of tris-(4-chlorophenyl) sulfonium 3,3,3,2,1,1-hexafluoropropane sulfonate (PAG 119)

A mixture of 13.56 g (5.0 mmol) of 4,4'-dichlorophenyl sulfoxide with 5.63 g (5.0 mmol) of 4-chlorobenzene was placed in a 125 ml flask. Then 20 ml of a previously prepared phosphorus pentaoxide/metanesulfonic acid reagent (prepared by dissolving 36 g of phosphorus pentaoxide in 360 g of methanesulfonic acid) was added thereto while stirring with a magnetic stirrer. A slight exothermic reaction occurred. The system was further heated at 55° C. for 6 hours. This resulted in significant color development. The system was then cooled to room temperature. The reaction mixture was poured into 100 ml of water and 100 g of ice. The slightly suspended solution was filtered, followed by addition of 11.6 g (5.0 mmol) of 3,3,3,2,1,1-hexafluoropropane sulfonic acid to yield a yellow oil. The oil was stirred for 1 hour, and 200 ml of dichloromethane was added thereto. The mixture was extracted. The organic phase was washed several times with water, and then dried. The solvent was removed by distillation. The oily residue was recrystallized from ethyl acetate to give 6.5 g of the contemplated material. The structure was confirmed by $^1$H-NMR (CDCl$_3$) with δ=5.25–5.52 (d[m], 1H), 7.32–7.43 (d, 6H), and 7.63–7.74 (d, 6H) ppm.

The purity was determined by HPLC analysis and found to be >97%.

Synthesis Example 120

Preparation of tris-(t-butoxycarbonyloxyphenyl) sulfonium 3,3,3,2,1,1-hexafluoropropane sulfonate (PAG 120)

56.8 g (0.08 mol) of tris-(4-butoxyphenyl) sulfonium 3,3,3,2,1,1-hexafluoropropane sulfonate (Synthesis Example 110) and 1.86 g (0.008 mol) of 3,3,3,2,1,1-hexafluoropropane sulfonic acid were dissolved in 200 ml of ethanol. The solution was heated under ref lux for 8 hours with stirring. After removal of the solvent by distillation, the obtained crude product of tris-(4-hydroxyphenyl) sulfonium 3,3,3,2,1,1-hexafluoropropane sulfonate (yield about 100%) was dissolved in 160 g of N,N-dimethylformamide and reacted with 55.4 g (0.40 mol) of anhydrous potassium carbonate and 60.3 g (0.40 mol) of di-t-butyl dicarbonate at 20° C. for 3 hours. The reaction solution was poured into 700 ml of water and extracted with dichloromethane. The organic phase was washed with water and dried. The solvent was removed by distillation. The oily residue was purified by column chromatography on silica gel using a dichloromethane and methanol as the developing solvent. The white product was collected to yield 31.8 g (yield 45%) of analytically pure tris-(4-t-butoxycarbonylmethoxyphenyl) sulfonium 3,3,3,2,1,1-hexafluoropropane sulfonate. The melting point of the product was 78° C. The $^1$H-NMR spectrum gave the following signals (CDCl$_3$): $\delta$=1.45 (s, 27H), 5.30–5.56 (d[m], 1H), 7.10–7.13 (d, 6H), 7.55–7.60 (d, 6H).

Synthesis Example 121

Preparation of 4-methylphenyl dimethyl sulfonium 3,3,3,2,1,1-hexafluoropropane sulfonate (PAG 121)

A mixture of 7.81 g (10.0 mmol) of dimethyl sulfoxide with 9.21 g (10.0 mmol) of toluene was placed in a 200 ml flask. Then 40 ml of a previously prepared phosphorus pentaoxide/metanesulfonic acid reagent (prepared by dissolving 36 g of phosphorus pentaoxide in 360 g of methanesulfonic acid) was added thereto while stirring with a magnetic stirrer. A slight exothermic reaction occurred. The system was stirred at room temperature for 6 hours. The reaction mixture was poured into 150 ml of water and 150 g of ice. The slightly suspended solution was filtered, followed by addition of 23.2 g (10.0 mmol) of 3,3,3,2,1,1-hexafluoropropane sulfonic acid to yield a colorless oil. The oil was stirred for 1 hour, and 200 ml of dichloromethane was added thereto. The mixture was extracted. The organic phase was washed several times with water, and then dried. The solvent was removed by distillation. The oily residue was recrystallized from isopropyl alcohol to give 6.5 g of the contemplated material. The structure was confirmed by $^1$H-NMR (CDCl$_3$) with $\delta$=2.41 (s, 3H), 3.46 (s, 6H), 5.32–5.56 (d[m], 1H), 7.42–7.45 (d, 2H), 7.50–7.53 (d, 2H) ppm.

The purity was determined by HPLC analysis and found to be >97%.

Synthesis Example 122

Preparation of 4-hdroxy-3,5-dimethylphenyl diphenyl sulfonium 3,3,3,2,1,1-hexafluoropropane sulfonate (PAG 122)

A mixture of 13.56 g (5.0 mmol) of diphenyl sulfoxide with 5.63 g (5.0 mmol) of 4-hydroxy-3,5-dimethylbenzene was placed in a 125 ml flask. Then 20 ml of a previously prepared phosphorus pentaoxide/metanesulfonic acid reagent (prepared by dissolving 36 g of phosphorus pentaoxide in 360 g of methanesulfonic acid) was added thereto while stirring with a magnetic stirrer. A slight exothermic reaction occurred. The system was further heated at 55° C. for 6 hours. This resulted in significant color development. The system was then cooled to room temperature. The reaction mixture was poured into 100 ml of water and 100 g of ice. The slightly suspended solution was filtered, followed by addition of 11.6 g (5.0 mmol) of 3,3,3.2,1,1-hexafluoropropane sulfonic acid to yield an yellow oil. The oil was stirred for 1 hour, and 200 ml of dichloromethane was added thereto. The mixture was extracted. The organic phase was washed several times with water, and then dried. The solvent was removed by distillation. The oily residue was recrystallized from ethyl acetate to give 6.5 g of the contemplated material. The structure was confirmed by $^1$H-NMR (CDCl$_3$): $\delta$=2.33 (s,6H), 5.34–5.51 (d[m], 1H), 7.35 (s, 1H), 7.41 (s, 1H), 7.63–7.79 ppm (m, 10H.

The purity was determined by HPLC analysis and found to be >97%.

Synthesis Example 123

Preparation of 2-phenylcarbonylmethyl dimethyl sulfonium 3,3,3,2,1,1-hexafluoropropane sulfonate (PAG 123)

18.13 g (100 mmol) of 2-phenylcarbonylmethyl dimethyl chloride was dissolved in 350 ml of chloroform, and 24.36 g (105 mmol) of 3,3,3,2,1,1-hexafluoropropane sulfonate was added to the solution. The mixture was refluxed for 6 hours. During the reflux, hydrogen chloride was evolved. The reaction mixture was cooled, extracted with water, and dried. The solvent was removed by distillation. The resultant solid was purified by recrystallization from isopropanol and diisopropyl ether. The structure was confirmed by $^1$H-NMR (CDCl$_3$): $\delta$=3.44 (s, 6H), 5.88 (s, 2H), 5.34–5.54 (d[m], 1H) 7.62–7.70 ppm (m, 5H).

Synthesis Example 124

Preparation of di-(4-t-butyloxyphenyl) iodonium 3, 3,3,2,1,1-hexafluoropropane sulfonate (PAG 124)

6.2 g (0.11 mol) of potassium hydroxide was dissolved in 250 ml of ethanol. 27.2 g (0.05 mol) of bis-(4-hydroxyphenyliodonium) 3,3,3,2,1,1-hexafluoropropane sulfonate (prepared from a metathesis reaction of chloride) was added to the solution. The mixture was stirred for 3 hours. The solution was then heated to 50° C., and 15.1 g (0.11 mol) of t-butyl bromide was added dropwise thereto. The mixture was heated under reflux for 6 hours. The precipitates were removed by filtration. The solvent was removed from the filtrate by distillation. The residue was dissolved in 250 ml of ethyl acetate. The solution was washed several times with water, and then dried. The solvent was removed to obtain a yellow oil. The contemplated material was obtained by recrystallization from diethyl ether. The structure was confirmed by $^1$H-NMR (CDCl$_3$): $\delta$=1.43 (s, 18H), 5.00–5.30 (d[m], 1H), 7.17–7.21 (d, 4H), 7.55–7.59 ppm (d, 4H).

Synthesis Example 125

Preparation of di-(4-t-butylcarbonyloxymethyloxyphenyl) iodonium 3,3,3, 2,1,1-hexafluoropropane sulfonate (PAG 125)

The title compound was obtained in substantially the same manner as in the above synthesis example, except that t-butyl bromide was replaced with an equal amount of t-butyl bromoacetate. The structure was confirmed by $^1$H-NMR (CDCl$_3$): $\delta$=1.42 (s, 18H), 4.55 (s, 4H), 4.94–5.18 (d[m], 1H), 7.10–7.14 (d, 4H), 7.56– 7.60 ppm (d, 4H).

Synthesis Example 126

Preparation of 4-t-butylphenyl phenyl iodonium 3, 3,3,2,1,1-hexafluoropropane sulfonate (PAG 126)

4.4 g (20 mmol) of iodosylbenzene was suspended in 100 ml of dry dichloromethane. The suspension was cooled to 0°

C. with stirring. 4.65 g (20 mmol) of 3,3,3,2,1,1-hexafluoropropane sulfonic acid (optionally distilled) was added at the same temperature thereto under exclusion of moisture. The mixture was stirred at room temperature for 3 hours. The temperature of the mixture was returned to 0° C., and 2.68 g (20 mmol) of 4-t-butylbenzene was added thereto at that temperature. The temperature of the mixture was returned to room temperature, followed by stirring for 6 hours. Thereafter, the insolubles were removed by filtration. The solvent was removed from the filtrate. The oily residue was purified by recrystallization (twice) from diethyl ether. The structure was confirmed by $^1$H-NMR (CDCl$_3$): δ=0.81 (s, 9H), 4.98–5.22 (m[d], 1H), 7.18–7.23 (d, 2H), 7.58–7.65 ppm (m, 7H).

Example 101

A copolymer of 4-hydroxystyrene and 4-t-butyloxycarbonylstyrene was prepared by reacting monodisperse poly-4-hydroxystyrene with di-t-butylcarbonate. The copolymer had a molecular weight of 8,700 with a polydispersity of 1.18 as determined by GPC using polystyrene as the standard. The molar ratio of 4-hydroxystyrene:4-t-butyloxycarbonylstyrene was 7:3 as concluded from inspection of the $^1$H NMR spectrum. This copolymer will be hereinafter often referred to as "POLY 101."

The following ingredients were mixed together to prepare a solution of a positive-working chemically amplified radiation sensitive composition suitable for DUV (248 nm) exposure:
9.8 g of the above copolymer,
0.3 g of triphenyl sulfonium 3,3,3,2,1,1-hexafluoropropane sulfonate,
0.02 of tetramethyl ammonium hydroxide,
0.004 g of Megafac R-08 (tradename), and
64.2 g of propylene glycol monomethyl ether acetate.

The solution was filtered through a teflon filter having a pore diameter of 0.1 μm, spin coated on a silicon wafer pre-coated with DUV-18, an antireflective coating provided by Brewer Science at a film thickness of 115 nm (bake temperature: 200° C.), at 3,000 revolutions and dried at 90° C. for 60 seconds on a hot plate to remove the solvent. Thus, a 0.72 μm-thick thin film was obtained. The recording material thus obtained was imagewise exposed using a mask providing lines and spaces patterns down to 0.10 μm per image with a DUV stepper Nikon NSR 2005 EX 10B, having a numerical aperture (NA) of 0.55 during exposure and a coherence factor ( a ) of 0.55 with a dose of 18 mJ/cm$^2$. The medium was baked at 100° C. for 90 seconds to develop the latent image, and then processed at 23° C. by puddle development with AZ MIF 300, a surfactant free developer containing 2.38% by weight of tetramethyl ammonium hydroxide provided by Clariant Japan K.K. A defect-free image of the mask with high edge stability was obtained, structures <0.25 μm being resolved faithfully to detail and the width ratio (linearity of the resist) of nominally equal lines/space structures being virtually constant in the range between 1.00 μm and 0.25 μm. The resist profile was almost vertical and very smooth, as neither edge roughness nor standing waves were observed.

Example 102

Radical copolymerization of 4-acetoxystyrene, styrene and t-butylmethacrylate was carried out in the presence of 2,2-azo-bis-isobutyronitrile as a polymerization initiator, followed by hydrolysis of the acetate groups with an aqueous ammonium acetate solution to prepare a terpolymer of 4-hydroxystyrene, styrene and t-butyl methacrylate. The terpolymer had a molecular weight of 14,200 with a polydispersity of 1.69 as determined by GPC using polystyrene as the standard, and the molar ratio of 4-hydroxystyrene:styrene:t-butylmethacrylate was 7:2:1 as determined by $^1$H NMR. This polymer will be hereinafter often referred to as "POLY 102."

The following ingredients were mixed together to prepare a solution of a positive-working chemically amplified radiation sensitive composition suitable for DUV (248 nm) exposure:
9.8 g of the above copolymer,
0.3 g of diphenyl iodonium 3,3,3,2,1,1-hexafluoropropane sulfonate,
0.03 g of triphenyl sulfonium acetate,
0.004 g of Megafac R-08 (tradename), and
64.2 g of propylene glycol monomethyl ether acetate.

The solution thus obtained was filtered, spin-coated on a HMDS treated silicon wafer and baked for 60 seconds on a hot plate at 130° C. to yield a film thickness of 0.82 μm. The recording material was exposed in the same manner as in Example 101. The dose was 27 mJ/cm$^2$. The film was then baked at 130° C. for 90 seconds. Subsequent development as described in Example 101 resolved line and space patterns below 0.23 μm. From scanning electron microscope (SEM) inspection, it was concluded that the linewidth of isolated and dense lines was almost equal, i.e. the dense to iso bias was negligible. Isolated line patterns were resolved down to 0.16 μm.

Example 103 and Comparative Examples 101 and 102

Radical polymerization of 4-t-butyloxystyrene was carried out in the presence of 2,2-azo-bis-isobutyronitrile as a polymerization initiator, followed by partial hydrolysis of the t-butyloxy groups with a concentrated aqueous hydrogen chloride solution to prepare 4-hydroxystyrene with 12% of the t-butyloxy styrene units being left intact. This copolymer was then reacted with ethyl vinyl ether in the presence of p-toluenesulfonic acid as a catalyst to prepare a terpolymer of 4-hydroxystyrene, 4-(1-ethoxyethoxy)styrene and 4-t-butoxystyrene. The terpolymer thus obtained had a molecular weight of 23,400 with a polydispersity of 2.14 as determined by GPC using polystyrene as the standard, and the molar ratio of 4-hydroxystyrene:styrene:t-butyl methacrylate styrene was about 6.7:2.2:1.1 as measured by $^1$H NMR. This polymer will be hereinafter often referred to as "POLY 103."

The following ingredients were mixed together to prepare solutions of a positive-working chemically amplified radiation sensitive composition suitable for DUV (248 nm) exposure:
9.8 g of the above copolymer,
0.3 g (0.61 mmol) of triphenylsulfonium 3,3,3,2,1,1-hexafluoropropane sulfonate (Example 103),
0.3 g (0.61 mmol) of triphenyl sulfonium camphor sulfonate (Comparative Example 101,
0.25 g (0.61 mmol) of triphenyl sulfonium trifluoromethane sulfonate (Comparative Example 102), hereinafter often referred to as "triphenylsulfonium triflate"),
0.02 g of triphenyl sulfonium acetate,
0.05 g of 9-anthramethyl acetate (DUV absorber),
0.004 g of Megafac R-08 (tradename), and
64.2 g of propylene glycol monomethyl ether acetate The solutions were filtered, and spin-coated on three silicon wafers, which have been precoated with an experimental antireflective coating provided by Clariant Japan K.K. at a film thickness of 60 nm (bake temperature: 220° C.). The resist films were baked for 60 seconds on a hot plate at 130° C. to yield a film thickness of 0.71±0.02 μm.

The recording materials were exposed as described in Example 101 (NA=0.50, σ=0.50) and then baked at 105° C. for 60 seconds. Development was done as described in Example 101. The following results were obtained (Table 101; rating was added in parenthesis (1)=best, (2) intermediate, (3)=poor):

TABLE 101

|  | Example 103 | Comparative Example 101 | Comparative Example 102 |
|---|---|---|---|
| Dose (mJ/cm$^2$) | 18 (1) | 29 (3) | 18 (1) |
| Dense Line Resolution (μm) | 0.18 (1) | 0.26 (3) | 0.18 (1) |
| Isolated Line Resolution (μm) | 0.17 (1) | 0.19 (2) | 0.20 (3) |
| Dense Line DOF @ 0.22 μm (μm) | 1.4 (1) | 0.0 (3) | 1.1 (2) |
| Isolated Line DOF @ 0.22 μm (μm) | 1.0 (1) | 0.6 (3) | 0.7–0.8 (2) |
| Dense/iso bias @ 0.22 μm (μm) | 17 (1) | Na (3) | 31 (2) |

Remarks: The dose is defined as the exposure energy to delineate equal lines and spaces of 0.22 μm pattern width. The dense line resolution is defined as the smallest equal lines and spaces patterns fully reproduced at that dose. The isolated line resolution is defined as the smallest isolated line pattern without top film loss of the line at that dose. The dense line DOF is defined as the depth of focus of equal lines and spaces at that dose. The isolated line DOF is defined as the depth of focus of isolated lines at that dose. The dense/iso bias is defined as the linewidth difference between dense lines and isolated lines at that dose.

These results clearly demonstrate that the resist material using the resist material of the present invention has the best lithographic performance among these three samples.

Example 104 and Comparative Examples 103 and 104

Monodisperse poly-4-hydroxystyrene (Nippon Soda Co., Ltd., Mw=12,000, polydispersity=1.16) was reacted with 2-chloroethyl vinyl ether in the presence of p-toluenesulfonic acid as a catalyst to prepare a copolymer of 4-hydroxystyrene and 4-(1-(2-chloroethoxy)ethoxy)styrene. The copolymer had a molecular weight of 13,700 with a polydispersity of 1.21 as determined by GPC using polystyrene as the standard, and the molar ratio of 4-hydroxystyrene: 4-(1-(2-chloroethoxy)ethoxy)styrene was 7.1:2.9 as measured by $^1$H NMR. This polymer will be hereinafter often referred to as "POLY 104."

The following ingredients were mixed together to prepare three solutions of a positive-working chemically amplified radiation sensitive composition suitable for DUV (248 nm) exposure:

9.8 g of the above copolymer,
0.25 g of triphenyl sulfonium 3,3,3,2,1,1-hexafluoropropane sulfonate (Example 104),
0.25 g of triphenyl sulfonium triflate (Comparative Example 103),
0.25 g of triphenyl sulfonium propane sulfonate (Comparative Example 104),
0.03 g of triphenyl sulfonium acetate,
0.004 g of Megafac R-08 (tradename), and
64.2 g of propylene glycol monomethyl ether acetate.

The solutions thus obtained were filtered, spin coated on two HMDS treated silicon wafers each (total 6 wafers), baked for 90 seconds on a hot plate at 110° C. to yield a thin layer having a thickness of 0.75±0.02 μm. The recording material was exposed as described in Example 101 (NA=0.55, σ=0.55). The dose was as indicated in Table 102. While one of each wafer was placed immediately on a hot plate and baked for 90 seconds at 90° C. (Test A), the second wafers were stored in the clean room for 60 minutes and then baked under the same conditions (Test B). Next, these wafers were developed as described in Example 101.

The results are compiled in Table 102.

TABLE 102

|  | Example 104 | Comparative Example 103 | Comparative Example 104 |
|---|---|---|---|
| Test A |  |  |  |
| Dose (mJ/cm$^2$) | 22 (2) | 20 (1) | 37 (3) |
| Dense Line Resolution (μm) | 0.17 (1) | 0.18 (2) | 0.21 (3) |
| Isolated Line Resolution (μm) | 0.17 (1) | 0.19 (2) | 0.19 (2) |
| Dense Line DOF @ 0.22 μm (μm) | 1.4–1.5 | 1.1 (2) | 1.1 (2) |
| Isolated Line DOF @ 0.22 μm (μm) | 1.0 (1) | 0.6 (3) | 0.7–0.8 (2) |
| Dense/iso bias @ 0.22 μm (nm) | 17 (1) | 30 (3) | 27 (2) |
| T-top | None (1) | None (1) | None (1) |
| Test B (after one hour) |  |  |  |
| Dose (mJ/cm$^2$) | 22 (1) | 21 (2) | 34 (3) |
| Dense Line Resolution (μm) | 0.17 (1) | 0.18 (2) | 0.22 (3) |
| Isolated Line Resolution (μm) | 0.17 (1) | 0.21 (2) | 0.21 (2) |
| Dense Line DOF @ 0.22 μm (μm) | 1.4–1.5 (1) | 0.9 (2) | 0.6 (3) |
| Isolated Line DOF @ 0.22 μm (μm) | 0.9 (1) | 0.4 (3) | 0.6 (2) |
| Dense/iso bias @ 0.22 μm (nm) | 19 (1) | 37 (3) | 32 (2) |
| T-top | None | Yes, slight | Yes, medium |

Remarks: The definition of the test items is the same as given in Example 103. T-top indicates formation of an insoluble phase on top of the resist.

These results demonstrate superior performance of the resist material of the present invention (Test A) and superiority in dimensional stability upon delay time changes (Test B).

Example 105

Monodisperse poly-4-hydroxystyrene (manufactured by Nippon Soda Co., Ltd., Mw=2,000, polydispersity=1.16) was reacted with dihydropyran and a minor amount of α, ω-triethylene glycol divinyl ether in the presence of p-toluenesulfonic acid to prepare a copolymer of 4-hydroxystyrene and 4-tetrahydropyranyloxystyrene partially crosslinked by α, ω-triethylene glycol divinyl ether. The copolymer had an average molecular weight of 7,500 with an essentially trimodal molecular weight distribution at about 2,300, 4,600 and 7,000 and a minor amount of higher crosslinked parts as determined by GPC with polystyrene as the standard, and the molar ratio of 4-hydroxystyrene: 4-tetrahydropyranyloxystyrene was roughly 6.9:3.1 as measured by $^1$H NMR. This polymer will be hereinafter often referred to as "POLY 105."

The following ingredients were mixed together to prepare a solution of a positive-working chemically amplified radiation sensitive composition suitable for DUV (248 nm) exposure:
9.8 g of the above copolymer,
0.42 g of t-butyloxycarbonylphenyl diphenyl sulfonium 3,3,3,2,1,1-hexafluoropropane sulfonate,
0.03 g of tri-n-octylamine,
0.05 g of N,N-dimethylacetamide,
0.004 g of Megafac R-08 (tradename), and
64.2 g of propylene glycol monomethyl ether acetate.

The solution was filtered, spin coated on a silicon wafer covered with a phosphor-spin-on-glass layer, which has been pretreated bake at 150° C., and baked for 90 seconds on a hot plate at 115° C. to yield a thin layer having a thickness of 0.65 $\mu$m. The recording material was exposed as described in Example 101 (NA=0.55, $\sigma$=0.71) using a mask with contact hole patterns down to 0.15 $\mu$m at a dose of 55 mJ/cm$^2$ and baked for 90 seconds at 120° C. Next the material was developed as described in Example 101. Scanning electron microscope (SEM) inspection revealed that the recording material resolved 0.20 $\mu$m contact holes at a duty ratio of 1:1 with a usable depth-of-focus (DOF) of about 0.9 $\mu$m. The side walls of the contact holes were vertically, and virtually no footing was observed at the resist/substrate interface.

Example 106

Monodisperse poly-4-hydroxystyrene (manufactured by Nippon Soda Co., Ltd., Mw=8,000, polydispersity=1.09) was reacted with ethyl vinyl ether in the presence of p-toluenesulfonic acid as a catalyst to prepare a copolymer. The copolymer was reacted with di-t-butylcarbonate in the presence of triethylamine to prepare a terpolymer of 4-hydroxystyrene, 4-(1-ethoxyethoxystyrene) and 4-(t-butyloxycarbonyloxystyrene). The terpolymer had an average molecular weight of 10,200 with a polydispersity of 1.13 as determined by GPC using polystyrene as the standard, and the molar ratio of 4-hydroxystyrene:4-(1-ethoxyethoxy)styrene:4-t-butyloxycarbonyloxystyrene was 6.5:3.8:0.7 as measured by $^1$H NMR. This polymer will be hereinafter often referred to as "POLY 106."

The following ingredients were mixed together to prepare a solution of a positive-working chemically amplified radiation sensitive composition suitable for DUV (248 nm) exposure:
9.8 g of the above terpolymer,
0.35 g of bis-(4-cyclohexylphenyl) phenyl sulfonium 3,3,3,2,1,1-hexafluoropropane sulfonate,
0.02 g of tetrabutyl ammonium hydroxide,
0.02 g of N,N-dicyclohexylamine,
0.004 g of Megafac R-08 (tradename), and
64.2 g of ethyl lactate.

The solution thus obtained was filtered, spin-coated on a HMDS treated silicon wafer and baked for 90 seconds on a hot plate at 85° C. to yield a thin layer having a thickness of 0.57 $\mu$m. The recording material was exposed as described in Example 101 (NA=0.55, $\sigma$=0.71) using a mask with contact hole patterns down to 0.15 $\mu$m at a dose of 55 mJ/cm$^2$ and baked for 90 seconds at 120° C. Next the material was developed as described in Example 101. Exposure was performed as described in Example 101 using NA=0.50 and a $\sigma$-value=0.60 at a dose of 24 mJ/cm$^2$. The material was baked for 90 seconds at 105° C., and developed with the surfactant-free developer of Example 101 for 60 seconds at 23° C. followed by water rinsing.

The material resolved dense lines and spaces patterns down to 0.19 $\mu$m and isolated lines down to 0.16 $\mu$m. The pattern shape was rectangular and no standing waves were observed. The DOF of the isolated patterns was larger than 1.0 $\mu$m for 0.18 $\mu$m features.

Examples 107 and 108

Radical copolymerization of 4-acetoxystyrene with 4-t-butylacrylate was carried out in the presence of 2,2'-azobis-(4-dimethoxy-2,4-dimethylvaleronitrile) as a polymerization initiator, followed by hydrolysis of the acetate groups with an aqueous ammonium acetate solution. A part of the hydroxy groups in the copolymer thus obtained were reacted with ethyl vinyl ether in the presence of p-toluenesulfonic acid as a catalyst to prepare a terpolymer of 4-hydroxystyrene, 4-(1-ethoxyethoxystyrene) and 4-t-butylacrylate. The terpolymer had an average molecular weight of 8,700 with a polydispersity of 1.71 as determined by GPC using polystyrene as the standard, and the molar ratio of 4-hydroxystyrene:4-(1-ethoxyethoxy)styrene:4-t-butylacrylate was 7.1:1.8:1.1 as measured by $^1$H NMR. This polymer will be hereinafter often referred to as "POLY 107."

The following ingredients were mixed together to prepare a solution of a positive-working chemically amplified radiation sensitive composition suitable for DUV (248 nm) and e-beam exposure:
9.8 g of the above terpolymer,
0.28 g of bis-(4-cyclohexylphenyl) iodonium 3,3,3,2,1,1-hexafluoropropane sulfonate,
0.03 g of triphenyl sulfonium hydroxide,
0.004 g of Megafac R-08 (tradename), and
64.2 g of propylene glycol monomethyl ether acetate.

The solution was filtered, spin-coated on two HMDS treated silicon wafers and baked on a hot plate for 90 seconds at 110° C. to yield a thin layer having a thickness of 0.53 $\mu$m. One of the recording materials was exposed with excimer laser radiation provided by a Nikon NSR 2005 EX 10B stepper with an NA=0.55 and a coherence factor $\sigma$=0.80 using a mask with lines and spaces patterns down to 0.10 $\mu$m at a dose of 27 mJ/cm$^2$. The other recording material was pattern-wise exposed with e-beam radiation provided from a JEOL JBXX 5DII operating at 50 keV with a spot size of 10 nm (no proximity correction) at a dose of 18.2 $\mu$C/cm$^2$. The exposed wafers were placed on a hot plate and baked for 90 seconds at 120° C. The materials were then developed with AZ® MIF 300, a surfactant free developer containing 2.38% by weight of tetramethyl ammonium hydroxide provided by Clariant Japan K.K. for 60 seconds at 23° C. followed by water rinsing.

The excimer laser exposed material resolved dense lines and spaces patterns down to 0.18 $\mu$m and isolated lines and spaces down to 0.14 $\mu$m. The pattern shape was rectangular and only minor standing waves were observed. The DOF of the isolated patterns was larger than 1.0 $\mu$m for 0.16 $\mu$m features.

The e-beam exposed material resolved dense lines and spaces down to 0.16 $\mu$m and isolated lines down to 0.11 $\mu$m. The DOF of the isolated patterns was larger than 1.0 $\mu$m for 0.15 $\mu$m features.

Examples 109 and 110

A terpolymer of 4-hydroxystyrene, 4-(t-butoxystyrene) and 4-t-butylcarbonylmethyloxy styrene was prepared by acid hydrolysis of monodisperse poly-4-t-butoxystyrene to leave 15% of the butoxy groups intact. A part of the hydroxy groups in the copolymer were reacted with t-butyl bromoacetate in the pressence of triethylamine as a catalyst. The terpolymer had an average molecular weight of 8,700 with a polydispersity of 1.06 as determined by GPC using polystyrene as the standard, and the molar ratio of 4-hydroxystyrene:4-(t-butoxystyrene:4-t-butylcarbonyloxystrene was 7.1:1.4:1.5 as measured by $^1$H NMR. This polymer will be hereinafter often referred to as "POLY 108." The following ingredients were mixed together to prepare a solution of a positive-working chemically amplified radiation sensitive composition suitable for DUV (248 nm) and x-ray exposure:

9.8 g of the above terpolymer,
0.2 g of bis-(t-butylcarbonylmethyloxyphenyl) iodonium 3,3,3,2,1,1-hexafluoropropane sulfonate,
0.15 g of tris-(t-butylcarbonylmethyloxyphenyl) sulfonium 3,3,3,2,1,1-hexafluoropropane sulfonate,
0.03 g of tributylammonium pyrovate,
0.004 g of Megafac R-08 (tradename), and
64.2 g of methyl amyl ketone.

The solution was filtered, spin-coated on two HMDS treated silicon wafers and baked on a hot plate (90 sec/100° C.) to yield a thin layer having a thickness of 0.72 μm. One of the recording materials was exposed with excimer laser radiation provided by a Nikon NSR 2005 EX 10B stepper (NA=0.55, σ=0.55) using a mask with lines and spaces patterns down to 0.10 μm at a dose of 25 mJ/cm$^2$. The other recording material was patternwise exposed with x-ray radiation provided by a 0.6 GeV superconducting beam storage ring with a peak wavelength of 7.5 A using a Karl Suss XRS-200/3 stepper with a proximity gap of 30 μm at a dose of 60 mJ/cm$^2$. The x-ray mask had lines and spaces pattern down to 100 nm and was composed of 0.5 μm thick W-Ti absorber on a 2.0 μm thick SiC membrane. The exposed wafers were baked for 90 seconds at 110° C. and developed as described in Example 101. The excimer laser exposed material resolved dense lines and spaces patterns down to 0.16 μm but the isolated lines were somewhat unstable and collapsed at geometries below 0.18 μm. The pattern shape was rectangular and only minor standing waves were observed. The DOF of the isolated patterns was larger than 1.0 μm for 0.16 μm features.

The x-ray exposed material resolved dense lines and spaces down to 0.14 μm and isolated lines down to 0.14 μm. At smaller geometries the patterns tended to collapse. The DOF of the isolated patterns was larger than 1.0 μm for 0.15 μm features.

Example 111

The following ingredients were mixed together to prepare a solution of a positive-working chemically amplified radiation sensitive composition suitable for DUV (248 nm) exposure:

9.8 g of the terpolymer described in Example 107 (POLY 107),
0.8 g of 4,4'-(1-methylethylidene) bis-[4,1-phenyleneoxy acetic acid] di(1,1-dimethylethyl) ester,
0.2 g of bis-(4-cyclohexylphenyl) phenyl sulfonium 3,3,3,2,1,1-hexafluoropropane sulfonate,
0.03 g of triphenyl sulfonium hydroxide,
0.05 g of a condensation product of 2 moles 9-anthrylmethanol reacted with 1 mole toluene-1,3-diisocyanate (DUV absorber),
0.004 g of Megafac R-08 (tradename), and
64.2 g propylene glycol monomethyl ether acetate.

The solution was filtered, spin-coated on a HMDS treated silicon wafer and baked on a hot plate (90 sec/110° C.) to yield a thin layer having a thickness of 0.51 μm, exposed as described previously (NA=0.55) at a dose of 34 mJ/cm$^2$, baked for 90 seconds at 120° C. and developed.

The material resolved dense lines and spaces patterns down to 0.16 μm and isolated lines down to 0.14 μm. The pattern shape was rectangular and only minor standing waves were observed. The DOF of the isolated patterns was about 0.8 μm for 0.16 μm features.

Examples 112 and 113

4-Hydroxystyrene, tetracyclododecyl methacrylate, t-butyl methacrylate and methacrylic acid 2-tetrahydropyranyl ester was radically polymerized in the presence of 2,2'-azobis(isobutyronitrile) as a polymerization initiator to prepare a quaterpolymer. The quaterpolymer had an average molecular weight of 13,200 with a polydispersity of 2.4 as determined by GPC using polystyrene as the standard, and the molar ratio of the components was 1.5:3.5:2.5:2.5 as measured by $^1$H NMR. This polymer will be hereinafter often referred to as "POLY 109."

The following ingredients were mixed together to prepare a solution of a positive-working chemically amplified radiation sensitive composition suitable for DUV (248 nm) exposure and VDUV (193 nm) exposure:

7.8 g of the quaterpolymer described above,
2.8 g of 4,4'-(1-methylethylidene) bis-[4,1-cyclohexyleneoxy acetic acid] di(1,1-dimethylethyl) ester,
0.2 g of bis-(4-cyclohexylphenyl) iodonium 3,3,3,2,1,1-hexafluoropropane sulfonate,
0.03 g of triethanolamine,
0.004 g of Megafac R-08 (tradename), and
64.2 g of propylene glycol monomethyl ether acetate.

The solution was filtered, spin-coated on two silicon wafers pretreated with AZ® KrF-2, a commercially available antireflective coating available from Clariant Japan K.K, baked for 90 seconds at 120° C. to yield a thin layer having a thickness of 0.51±0.02 μm, and one wafer was exposed as described in Example 101 (NA=0.55, σ=0.80) at a dose of 24 mJ/cm$^2$, while the other wafer was exposed with an ISI ArF stepper with a NA=0.60 and a σ=0.75 at a dose of 11 mJ/cm$^2$. The exposed wafers were baked for 90 seconds at 125° C. and developed.

The KrF excimer laser exposed material resolved dense lines and spaces patterns below 0.16 μm, isolated lines down to 0.14 μm, but both with a slight tendency to form T-tops. The ArF excimer laser exposed material showed the same resolution and pattern characteristics as the KrF excimer laser exposed material, however, the DOF of 0.18 μm lines exceeded that of the KrF exposed material by 25%.

Examples 114–137

The following radiation sensitive compositions were prepared and processed according to the steps indicated in Table 103, where "Polymer" denotes the polymer used,
"PAG" denotes the PAG (photoacid generator) used,
"DissInh" denotes the dissolution inhibitor used,
"Base" denotes the basic additive used,
"Solv" denotes the solvent used,
"Ratio" denotes the component ratio in parts by weight,
"Substrate" denotes the substrate to be coated with the radiation sensitive composition,
"PB" denotes the applied prebake conditions (temperature/time),
"FT" denotes the film thickness of the radiation sensitive composition,
"Exposure Type" denotes the radiation wavelength employed (ArF=193 nm excimer laser, KrF=248 nm excimer laser, i-line=365 nm quartz lamp, e-beam=30 keV electron beams, x-ray=1.3 nm), "Dose" denotes the applied exposure dose (in mJ/cm² for ArF. KrF, I-line and x-rays and in μC/cm² for e-beam), PEB denotes the applied post exposure bake conditions (temperature/time), "Dev" denotes conditions for development (temperature/time) with an aqueous 2.38% tetramethyl ammonium hydroxide solution, "Res" denotes the resolution capability of dense 1:1 lines and spaces, "Delay Stability" denotes the linewidth change <10% upon delay between exposure and post exposure bake, "Profile Angle" denotes the angle between the substrate and the sidewall of 0.25 μm line patterns, and "DOF" denotes the depth of focus of dense 0.25 μm lines.

TABLE 103

| EXAMPLE # | 114 | 115 | 116 | 117 | 118 | 119 |
|---|---|---|---|---|---|---|
| Polymer | POLY 110 | POLY 110 | POLY 110 | POLY 111 | POLY 111 | POLY 111 |
| PAG | PAG 102 | PAG 102 | PAG 117 | PAG 104 | PAG 118 | PAG 110 |
| DissInh | — | DISS 101 | — | — | — | DISS 102 |
| Base | BASE 101 | BASE 101 | BASE 107 | BASE 102 | BASE 107 | BASE 103 |
| Solvent | SOLV 101 | SOLV 101 | SOLV 101 | SOLV 101 | SOLV 101 | SOLV 103 |
| Ratio (ppw) | 11.5/0.3/ 0.0/0.04/ 84.7 | 13.0/0.3/ 2.1/0.05/ 85.8 | 14.5/0.7/ 0.0/0.03/ 86.0 | 14.0/0.4/ 0.0/0.02/ 85.1 | 13.7/0.3/ 0.0/0.03/ 85.5 | 13.2/0.8/ 2.2/0.03/ 84.4 |
| Substrate | Si | BARC 101 | BARC 101 | BARC 102 | BARC 102 | BARC 102 |
| PB [° C./sec] | 90/60 | 90/60 | 90/60 | 110/60 | 135/60 | 135/60 |
| FT [μm] | 0.75 | 0.67 | 0.75 | 0.75 | 0.75 | 0.75 |
| Exposure Type | KrF | KrF | KrF | KrF | KrF | KrF |
| Dose [mJ (μC)/cm²] | 38 | 34 | 42 | 28 | 26 | 32 |
| PEB [° C./sec] | 105/90 | 115/90 | 105/90 | 120/90 | 135/90 | 135/90 |
| Dev [° C./sec] | 23/60 | 23/60 | 23/60 | 23/60 | 23/60 | 23/60 |
| Res [μm] | 0.18 | 0.19 | 0.17 | 0.19 | 0.18 | 0.18 |
| Delay Stability [hrs] | >2 | >2 | >4 | >2 | >4 | >4 |
| Profile Angle [°] | >86 | >87 | >86 | >86 | >86 | >86 |
| DOF @ 0.25 μm [μm] | 1.20 | 1.30 | 1.20 | 1.25 | 1.30 | 1.25 |

| EXAMPLE # | 120 | 121 | 122 | 123 | 124 | 125 |
|---|---|---|---|---|---|---|
| Polymer | POLY 112 | POLY 113 | POLY 114 | POLY 114 | POLY 115 | POLY 116 |
| PAG | PAG 122 | PAG 125 | PAG 102 | PAG 104 | PAG 126 | PAG 123 |
| DissInh | — | DISS 101 | — | — | — | DISS 102 |
| Base | BASE 107 | BASE 107 | BASE 107 | BASE 104 | BASE 106 | BASE 107 |
| Solvent | SOLV 101 | SOLV 102 | SOLV 101 | SOLV 101 | SOLV 101 | SOLV 101 |
| Ratio | 16.0/0.4/ 0.0/0.05/ 83.5 | 13.1/0.1/ 0.8/0.04/ 85.9 | 14.3/0.4/ 0.0/0.1/ 85.0 | 14.7/0.3/ 0.0/0.03/ 84.5 | 13.9/0.7/ 6.0/0.03/ 85.3 | 12.2/0.4/ 1.4/0.03/ 85.6 |
| Substrate | BARC 101 | Si | BARC 101 | BARC 103 | BARC 105 | BARC 101 |
| PB [° C./sec] | 90/60 | 110/60 | 90/60 | 110/60 | 115/60 | 115/60 |
| FT [μm] | 0.75 | 0.67 | 0.55 | 0.75 | 0.52 | 0.70 |
| Exposure Type | KrF | e-beam | KrF | KrF | ArF | KrF |
| Dose [mJ (μC)/cm²] | 38 | 26.4 | 47 | 28 | 14 | 52 |
| PEB [° C./sec] | 105/90 | 125/90 | 105/90 | 110/90 | 125/90 | 115/90 |
| Dev [° C./sec] | 23/60 | 23/60 | 23/60 | 23/60 | 23/20 | 23/60 |
| Res [μm] | 0.18 | 0.15 | 0.17 | 0.19 | 0.15 | 0.18 |
| Delay Stability [hrs] | >2 | >2 | >4 | >2 | >1 | >4 |
| Profile Angle [°] | >86 | >87 | >86 | >86 | >86 | >86 |
| DOF @ 0.25 μm [μm] | 1.20 | >1.30 | 1.20 | 1.25 | 1.30 | 1.25 |

| EXAMPLE # | 126 | 127 | 128 | 129 | 130 | 131 |
|---|---|---|---|---|---|---|
| Polymer | POLY 117 | POLY 118 | POLY 118 | POLY 115 | POLY 119 | POLY 120 |
| PAG | PAG 125/ 120 | PAG 102 | PAG 101 | PAG 124 | PAG 104 | PAG 110 |
| DissInh | — | — | DISS 3 | — | — | DISS 4 |
| Base | BASE 107 | BASE 101 | BASE 105 | BASE 103 | BASE 102 | BASE 104 |
| Solvent | SOLV 101 | SOLV 102 | SOLV 101 | SOLV 101 | SOLV 101 | SOLV 103 |
| Ratio | 14.3/0.8/ 0.0/0.1/ 87.0 | 16.5/0.4/ 0.0/0.04/ 83.5 | 16.1/0.1/ 0.8/0.04/ 85.9 | 14.3/0.4/ 0.0/0.1/ 85.0 | 14.7/0.4/ 0.0/0.03/ 84.5 | 17.9/0.5/ 0.0/0.03/ 85.3 |
| Substrate | Si | BARC 104 | BARC 101 | BARC 105 | BARC 101 | Si |
| PB [° C./sec] | 110/60 | 115/60 | 135/60 | 135/60 | 110/60 | 90/60 |
| FT [μm] | 0.75 | 0.67 | 0.75 | 0.45 | 0.65 | 0.75 |
| Exposure Type | x-ray | KrF | KrF | ArF | KrF | i-line |
| Dose [mJ (μC)/cm²] | 65 | 34 | 42 | 19 | 46 | 78 |
| PEB [° C./sec] | 125/90 | 125/90 | 135/90 | 135/90 | 120/90 | 100/90 |
| Dev [° C./sec] | 23/60 | 23/60 | 23/60 | 23/60 | 23/60 | 23/60 |
| Res [μm] | 0.12 | 0.17 | 0.19 | 0.15 | 0.18 | 0.24 |
| Delay Stability [hrs] | >2 | >2 | >4 | >2 | >4 | >4 |
| Profile Angle [°] | >86 | >87 | >86 | >86 | >86 | >86 |
| DOF @ 0.25 μm [μm] | >1.80 | 1.30 | 1.20 | 1.45 | 1.30 | 0.25 |

| EXAMPLE # | 132 | 133 | 134 | 135 | 136 | 137 |
|---|---|---|---|---|---|---|

TABLE 103-continued

| Polymer | POLY 110 | POLY 116 | POLY 121 | POLY 111 | POLY 111 | POLY 120 |
|---|---|---|---|---|---|---|
| PAG | PAG 102 | PAG 126 | PAG 124 | PAG 119 | PAG 102 | PAG 110 |
| DissInh | — | DISS 101 | — | — | — | DISS 102 |
| Base | BASE 101 | BASE 101 | BASE 103 | BASE 102 | BASE 103 | BASE 104 |
| Solvent | SOLV 101 | SOLV 102 | SOLV 101 | SOLV 101 | SOLV 101 | SOLV 103 |
| Ratio | 16.3/0.41 0.0/0.1/ 85.3 | 16.2/0.7/ 0.0/0.02/ 83.5 | 15.8/0.1/ 0.8/0.04/ 85.9 | 14.3/0.41 0.0/0.1/ 85.0 | 14.7/0.4/ 0.01/0.03/ 84.5 | 17.9/0.51 0.0/0.03/ 85.3 |
| Substrate | BARC 101 | Si | BARC 105 | BARC 102 | BARC 101 | Si |
| PB [° C./sec] | 90/60 | 90/60 | 125/60 | 110/60 | 135/66 | 95/60 |
| FT [μm] | 0.77 | 0.67 | 0.45 | 0.57 | 0.68 | 0.85 |
| Exposure Type | KrF | x-ray | ArF | KrF | KrF | i-line |
| Dose [mJ (μC)/cm²] | 38 | 54 | 12 | 28 | 26 | 96 |
| PEB [° C./sec] | 105/90 | 115/90 | 115/90 | 120/90 | 135/90 | 100/90 |
| Dev [° C./sec] | 23/60 | 23/60 | 23/60 | 23/60 | 23/60 | 23/60 |
| Res [μm] | 0.20 | 0.15 | 0.14 | 0.19 | 0.18 | 0.26 |
| Delay Stability [hrs] | >2 | >2 | >1 | >2 | >4 | >4 |
| Profile Angle [°] | >86 | >87 | >86 | >86 | >86 | >86 |
| DOF @ 0.25 μm [μm] | 1.05 | >1.80 | 1.40 | 1.25 | 1.35 | — |

The following abbreviations were used for the ingredients shown in the table.
POLY 101 to POLY 109=see the above examples
POLY 110=poly-(4-hydroxystyrene-co-4-(1-ethoxyethoxy)styrene), 6.7:3.3; Mw=8,700; D=1.12;
POLY 111=poly-(4-hydroxystryene-co-t-butylmethacrylate); 7.2:2.8; Mw=11,400; D=1.86;
POLY 112=poly-(4-hydroxystyrene-co-4-(1-ethoxyisopropoxy)styrene; 6.9:3.1; Mw=8,200; D=1.14;
POLY 113=poly-(3-hydroxystyrene-co-4-t-butyl vinylphenoxyacetate); 6.8:3.2; Mw=15,200, D=2.21;
POLY 114=poly-(4-hydroxystyrene-co-4-(1-ethoxyethoxy)styrene-co-4-methylstyrene); 6.0:3.2 0.8; Mw=14,000; D=1.84;
POLY 115=poly-(4-hydroxystyrene-co-8-methyl-8-t-butoxycarbonyltetracyclo[4.4.0.1$^{2.5}$.1$^{7.10}$]dodec-3-ene-co-maleic anhydride); 1:4:5; Mw=4,800; D=2.45;
POLY 116=poly-(4-hydroxystyrene-co-4-(1-ethoxyethoxy)styrene-co-4-tetrahydropyranyloxystyrene); 6.5:2.5:1.0; Mw=9,400; D=1.18;
POLY 117=poly-(4-hydroxystyrene-co-styrene-co-4-t-butyl vinylphenoxyacetate); 6.0:2.0:2.0; Mw=12,300; D=1.72;
POLY 118=poly-(4-hydroxystyrene-co-4-t-butyloxycarbonyloxystyrene-co-t-butylmethacrylate); 6.8:2.1:1.1; Mw=7,200; D=1.65;
POLY 119=poly-(-4-hydroxystyrene-co-4-butoxystyrene-co-4-(1-ethoxyethoxy)styrene-co-4-vinylbenoic acid t-butylester); 7.0:1.2:1.3:0.5; Mw=11,300, D=2.25;
POLY 120=poly-(4-hydroxystyrene-co-2-hydroxystyrene); 2:8; Mw=9,200, D=1.85;
POLY 121=poly-(2-hydroxystyrene-co-2-methyl-adamantyl methacrylate-co-mevalonyl methacrylate); 1:6:3; Mw=7,700, D=2.17;
PAG 101 to PAG 126=see the above synthesis examples
DISS 101=4,4'-(1-phenylethylidene)-bis-[4,1-phenyleneoxy acetic acid]-di-(1,1-dimethylethyl)ester,
DISS 102=ethylidene tris-[4,1-phenyleneoxy acetic acid]-tris-( 1,1-dimethylethyl)ester,
DISS 103=(1-methylethylidene)-di-4,1-phenylene-bis-(1,1-dimethylethyl)carbonic acid ester,
DISS 104=ethylidene-tris-4,1-phenylene-tris-(1,1-dimethylethyl)carbonic acid ester,
BASE 101=tetramethyl ammonium hydroxide,
BASE 102=tetra-n-butyl ammonium hydroxide,
BASE 103=tetra-n-butyl ammonium lactate,
BASE 104=methyldicyclohexylamine,
BASE 105=tri-n-octylamine,
BASE 106=triethanolamine,
BASE 107=triphenyl sulfonium acetate,
SOLV 101=propylene glycol monomethyl ether acetate,
SOLV 102=ethyl lactate,
SOLV 103=methyl amyl ketone,
BARC 101=DUV BARC AZ® KrF-3B® (available from Clariant Japan K.K.),
BARC 102=DUV BARC CD-9® (available from Brewer Science),
BARC 103 DUV BARC DUV18® (available from Brewer Science)
BARC 104 DUV BARC DUV42® (available from Brewer Science),
BARC 105=i-line BARC AZ® BarLi® II (available from Clariant Japan K.K.).

All formulations contain a minor amount(<0.01 ppw) of Megafac R-08 (tradename) surfactant.

Example 138 and Comparative Examples 105 and 106

The following ingredients were mixed together to prepare three solutions of a positive-working chemically amplified radiation sensitive composition suitable for DUV (248 nm) exposure:

9.8 g of the terpolymer (POLY 102) of the Example 102,
0.35 g (0.708 mmol) of triphenyl sulfonium 3,3,3,2,1,1-hexafluoropropane sulfonate (Example 138) or
0.54 g (0.708 mmol) of triphenyl sulfonium perfluorooctane sulfonate (Comparative Example 104) or
0.29 g (0.708 mmol) of triphenyl sulfonium trifluoromethane sulfonate (Comparative Example 105),
0.02 g of triphenyl sulfonium acetate,
0.004 g of Megafac R-08 (tradename), and
64.2 g of propylene glycol monomethyl ether acetate.

The solutions were filtered, and spin coated on two silicon wafers each, which have been precoated with DUV 30, an antireflective coating provided by Brewer Science at a film thickness of 90 nm (bake conditions: 190° C./60 sec). The substrate reflectivity at this film thickness was approximately 6%. The films were baked for 90 seconds at 120° C. to yield thin films having a thickness of 0.72±0.01 μm and exposed as described in Example 101. The exposure was followed by a post exposure bake at 120° C. for 60 seconds and a development.

The following results (Table 104) were obtained. The test items in the table were the same as those in Example 103.

TABLE 104

|  | Example 138 | Comparative Example 105 | Comparative Example 106 |
|---|---|---|---|
| Dose (mJ/cm$^2$) | 22 (2) | 26 (3) | 21 (1) |
| Dense Line Resolution ($\mu$m) | 0.22 (1) | 0.24 (3) | 0.22 (1) |
| Isolated Line Resolution ($\mu$m) | 0.12 (1) | 0.15 (3) | 0.13 (2) |
| Dense Line DOF @ 0.22 $\mu$m ($\mu$m) | 0.5–0.6 (1) | 0.0 (3) | 0.3–0.4 (2) |
| Isolated Line DOF @ 0.22 $\mu$m ($\mu$m) | 1.8 (1) | 1.6 (3) | 1.7–1.8 (2) |
| Dense/iso bias @ 0.22 $\mu$m (nm) | 22 (1) | Na (3) | 27 (2) |
| Dense Pattern Profile @ 0.18 $\mu$m | Good (2) | Very good (1) | Good (2) |
| Isolated Pattern Profile @ 0.15 $\mu$m | Good (1) | Film Loss (3) | Tapered (2) |
| Standing Waves | Visible (1) | Strong (2) | Visible (1) |
| Dense/iso bias @ 0.22 $\mu$m (nm) | 22 (1) | Na (3) | 27 (2) |

From these results, it can be concluded that the material of the present invention has some superiority in the overall performance.

Example 139 and Comparative Examples 107 and 108

The following ingredients were mixed together to prepare three solutions of a positive-working chemically amplified radiation sensitive composition suitable for DUV (248 nm) exposure.

9.8 g of the terpolymer (POLY 103) of Example 103,
0.5 g of α, α-bis(cyclohexylsulfonyl)diazomethane,
0.35 g of triphenyl sulfonium 3,3,3,2,1,1-hexafluoropropane sulfonate (Example 139) or
0.35 g of triphenyl sulfonium trifluoromethane sulfonate (Comparative Example 107) or
0.35 g of diphenyl iodonium trifluoromethane sulfonate (Comparative Example 108),
0.03 g of triphenyl sulfonium acetate,
0.004 g of Megafac R-08 (tradename), and
64.2 g of propylene glycol monomethyl ether acetate.

The solutions were filtered, and spin coated on two silicon wafers each, which have been precoated with DUV 42, a antireflective coating provided by Brewer Science Corp., USA, at a film thickness of 60 nm (bake conditions: 200° C./60 sec). The substrate reflectivity at this film thickness was less than 5%. Baking for 90 seconds at 90° C. provided a thin layer having a thickness of 0.65±0.01 $\mu$m. Top-view inspection of the photoresists by microscope and scanning electron microscope indicated that all three films exhibited smooth surfaces without any sign of pinholes, popcorns, or cracking. The recording materials were exposed as described in Example 101 (NA=0.55, σ=0.55) using a half-tone mask with 0.3 $\mu$m contact hole patterns at a dose of 18 mJ/cm$^2$, baked at 105° C. for 90 seconds and developed.

The results are summarized in Table 105.
The test items were the same as those in Example 103.

TABLE 105

|  | Example 139 | Comparative Example 107 | Comparative Example 108 |
|---|---|---|---|
| Dose (mJ/cm$^2$) | 42 (3) | 41 (2) | 32 (1) |
| Dense C/H Resolution ($\mu$m) | 0.22 (1) | 0.22 (1) | 0.22 (1) |
| Isolated C/H Resolution ($\mu$m) | 0.22 (1) | 0.23 (2) | 0.23 (2) |
| Dense C/H DOF @ 0.25 $\mu$m ($\mu$m) | 1.8 (1) | 1.7 (2) | 1.6 (3) |
| Isolated C/H DOF @ 0.25 $\mu$m ($\mu$m) | 1.3 (1) | 1.1 (3) | 1.2 (2) |
| C/H Sidewalls @ 0.25 $\mu$m | Vertical (1) | Vertical (1) | Tapered (2) |
| C/H Bottom @ 0.25 $\mu$m | Good (1) | Foot (2) | Undercut (3) |
| C/H Top @ 0.25 $\mu$m | Clear (1) | Round (3) | Round (2) |
| Standing Waves | Visible (1) | Visible (1) | Visible (1) |
| Surface After Development | Smooth (1) | Popcorn (2) | Popcorn (2) |

These results indicate the material of the present invention are superior in performance also in use as contact hole resist.

Example 140 and Comparative Example 109

Monodisperse poly-(4-hydroxystyrene) (provided from Nippon Soda Corp.) was reacted with ethyl vinyl ether to prepare a copolymer. The copolymer had a molecular weight of 6,800 with 32% of the phenolic hydroxy groups protected.

The following ingredients were mixed together to prepare two solutions of a positive-working chemically amplified radiation sensitive composition suitable for DUV (248 nm) exposure.

9.8 g of the above polymer,
1.2 g of a divinyl ether derivative prepared by the Williamson ether reaction of 1 mol bisphenol A with 2 moles 2-chloroethyl vinyl ether,
0.35 g (0.708 mmol) of triphenyl sulfonium 3,3,3,2,1,1-hexafluoropropane sulfonate (Example 140) or
0.29 g (0.708 mmol) of triphenyl sulfonium triflouromethane sulfonate (Comparative Example 109) or
0.03 g of triphenyl sulfonium acetate,
0.004 g of Megafac R-08 (tradename), and
64.2 g of propylene glycol monomethyl ether acetate.

The solutions thus obtained were filtered and spin coated on two silicon wafers each, which have been precoated with AZ KrF-2 (tradename), an antireflective coating provided by Clariant Japan K.K., at a film thickness of 60 nm (bake conditions: 220° C./60 sec). The photoresist films were baked for 90 seconds at 115° C. to yield a film thickness of 0.62±0.01 $\mu$m. After exposure as described in Example 101 (NA=0.55, σ=0.55) at a dose of 29 mJ/cm$^2$, the exposed wafers were baked at 120° C. for 90 seconds and developed.

The recording material of the present invention resolved lines and spaces down to 0.20 $\mu$m with vertical sidewalls profiles. The material of the Comparative Example 109 showed a resolution limit at 0.28 $\mu$m and strong foot formation. A dissolution rate analysis revealed that the contrast of the comparative material was significantly degraded probably due to a crosslinking reaction of the divinyl ether derivative at the selected post exposure bake temperature.

Example 141

The following ingredients were mixed together to prepare a solution of positive-working chemically amplified radiation sensitive composition suitable for i-line (365 nm) exposure:

8.6 g of a copolymer (molecular weight 12,200) of 3-methyl-4-hydroxystyrene and 4-hydroxystyrene (2:1),
2.8 g of the poly-N,O-acetal described in Example 138,
0.45 g of 2-anthryl diphenyl sulfonium 3,3,3,2,1,1-hexafluoropropane sulfonate,
0.04 g of triphenyl sulfonium hydroxide,
0.004 g of Megafac R-08 (tradename), and
88.5 g of ethyl lactate.

The solution thus obtained was filtered and spin coated on a wafer precoated with a 160 nm thick film of AZ Barli (tradename), a commercial antireflective coating available from Clariant Japan K.K., which has been baked at 200° C. for 60 seconds. The photoresist was baked at 110° C. for 60 seconds to give a film thickness of 850 nm. The coated wafer was exposed through a mask with line and space patterns down to 0.20 µm using a Nikon SNR1705I stepper (NA=0.50) at a dose of 56 mJ/cm². After the exposure, the wafer was baked at 90° C. for 60 seconds and developed as described in Example 101. After water rinsing, the wafer was dried and observed under SEM. The material resolved 0.26 µm lines and space patterns free of scum and T-top formation.

Example 142

A solution of a positive-working chemically amplified radiation sensitive composition suitable for VDUV (193 nm) exposure was prepared from the following ingredients:
11.14 g of poly(2-hydroxystyrene-co-2-methyl-2-adamantyl methacrylate-co-mevalonic lactone methacrylate) with a molecular weight of 8,000 and a polydisersity of 1.82,
0.31 g of bis-4-cyclohexylphenyl iodonium 3,3,3,2,1,1-hexafluoropropane sulfonate,
0.04 g of methyl diethanolamine,
0.004 g of Megafac R-08 (tradename), and
88.5 g of ethyl lactate.

The solution thus obtained was filtered and spin coated on a wafer precoated with a 60 nm thick film of an experimental methacrylate based antireflective coating developed by Clariant Japan K.K., which has been baked at 200° C. for 60 seconds. The photoresist was baked at 90° C. for 60 seconds to give a film thickness of 450 nm and exposed through a mask with line and space patterns down to 0.10 µm using a ISI ArF excimer laser with a NA=0.60 at a dose of 14.5 mJ/cm². After the exposure, the wafer was baked at 110° C. for 60 seconds and developed with an aqueous developer AZ MIF 300 (tradename: available from Clariant Japan K.K.) containing 2.38% tetramethyl ammonium hydroxide for 60 seconds at 230° C. The material resolved 0.14 µm lines and space pattern without any T-top formation. The interface between the antireflective coating and the photoresist was free of scum.

Example 143

A solution of negative-working chemically amplified radiation sensitive composition suitable for DUV (248 nm) exposure was prepared from the following ingredients:
7.9 g of a copolymer of 4-hydroxystyrene and styrene prepared by radical polymerization in the presence of 2,2'-azobis(4-methoxy-2,4-dimethylvaleronitrile) as a polymerization initiator, the copolymer having a molecular weight of 9,200 and a polydispersity of 2.14 as determined by GPC using polystyrene as the standard and a monomer ratio of 8:2 as determined by $^1$H-NMR,
2.0 g of distilled hexamethoxymethyl melamine,
0.3 g of triphenyl sulfonium 3,3,3,2,1,1-hexafluoropropane sulfonate,
0.02 g of tetrabutyl ammonium lactate,
0.004 g of Megafac R-08 (tradename), and
62.4 g of propylene glycol monomethyl ether acetate.

The solution thus obtained was filtered, spin coated onto a HMDS treated silicon wafer at 3,000 rpm, and baked on a hot plate at 115° C. for 60 seconds. The resulting film thickness was 0.72 µm. An exposure as described in Example 101 followed at a dose of 28 mJ/cm². The exposed material was then subjected to a post exposure bake on a hot plate at 125° C. for 90 seconds and developed. The fine lines and spaces were resolved down to 0.20 µm. Isolated lines were resolved down to 0.16 µm when a dose of 34 mJ/cm² was applied. The depth-of-focus of the 0.16 µm lines was about 0.80 µm.

Examples 144 and 145

A solution of negative-working chemically amplified radiation sensitive composition suitable for DUV (248 nm) and e-beam exposure was prepared from the following ingredients:
7.9 g of a copolymer of 4-hydroxystyrene and 4-methoxystyrene prepared by radical polymerization in the presence of 2,2'-azobis(isobutyronitrile) as a polymerization initiator, the copoylmer having a molecular weight of 9,600 and a polydispersity of 2.21 as determined by GPC using polystyrene as the standard and a monomer ratio of 7.8:2.2 as determined by $^1$H-NMR,
2.0 g of recrystallized tetramethoxymethyl glucoril,
0.5 g of tetrabutoxymethyl glucoril,
0.3 g of tris-(4-t-butylphenyl) sulfonium 3,3,3,2,1,1-hexafluoropropane sulfonate,
0.02 g of tetramethyl ammonium hydroxide,
0.004 g of Megafac R-08 (tradename), and
62.4 g of propylene glycol monomethyl ether acetate.

The solution thus obtained was filtered and spin coated onto two silicon wafers treated with an adhesion promoter (hexamethyl disilazane) at 3,000 rpm. After baking on a hot plate at 95° C. for 60 seconds, a film thickness of 0.74±0.2 µm was obtained. One wafer was subjected to an exposure through a mask with fine lines and space patterns down to 0.10 µm using a Nikon NSR 2005 EX 10B KrF excimer laser stepper (NA=0.55, σ=0.80) at a dose of 24 mJ/cm². The other wafer was exposed with e-beam using the e-beam writer described in Example 108 at a dose of 14.3 µC/cm². The exposed materials then were subjected to a post exposure bake on a hot plate at 95° C. for 90 seconds and developed.

The excimer laser exposed material resolved fine lines and spaces down to 0.20 µm. Isolated lines were resolved down to 0.15 µm when a dose of 31 mJ/cm² was applied. The depth-of-focus of the 0.15 µm lines was about 0.90 µm.

The e-beam exposed material yielded isolated lines with a linewidth below 0.10 µm.

Examples 146 and 147

A solution of a negative-working chemically amplified radiation sensitive composition suitable for DUV (248 nm) and x-ray exposure was prepared from the following ingredients:
5.9 g of a terpolymer of 4-hydroxystyrene, styrene and N-hydroxymethyl methacrylamide with a molecular weight of 11, 500, a polydispersity of 1.69, and a monomer ratio of 8:1.8:0.2,
1.5 g of recrystallized tetramethoxymethyl glucoril,
0.5 g of 4,4'-(1-methylethylidene)-bis-[2,6-bis-(hydroxymethyl)-phenol]

0.3 g of di-(4-t-butylphenyl) iodonium 3,3,3,2,1,1-hexafluoropropane sulfonate,
0.02 g of tetramethyl ammonium hydroxide,
0.004 g of Megafac R-08 (tradename), and
62.4 g of propylene glycol monomethyl ether acetate.

The solution thus obtained was filtered and spin coated onto two silicon wafers treated with an adhesion promoter (hexamethyl disilazane) at 3,000 rpm. After baking on a hot plate at 95° C. for 60 seconds, a film thickness of 0.67±0.02 μm was obtained.

One of the wafers was subjected to an exposure through a mask with fine lines and space patterns down to 0.10 μm using a Nikon NSR 2005 EX 10B KrF excimer laser stepper (NA=0.55, σ=0.55) at a dose of 18 mJ/cm$^2$. The other wafer was exposed with x-rays as described in Example 110 at a dose of 52 mJ/cm$^2$. The exposed materials were then subjected to a post exposure bake on a hot plate at 95° C. for 90 seconds and developed.

The fine lines and spaces of the excimer laser exposed material were resolved down to 0.22 μm. Isolated lines were resolved down to 0.18 μm when a dose of 25 mJ/cm$^2$ was applied. The depth-of-focus of the 0.18 μm lines was about 1.25 μm.

The x-ray exposed material resolved dense lines and spaces down to 0.16 μm while isolated lines were resolved down below 0.16 μm.

Example 148 and Comparative Example 110

Two negative-working chemically amplified radiation sensitive composition solutions suitable for i-line (365 nm) exposure were prepared from the following ingredients:
7.2 g of a copolymer (molecular weight 15,000, glass transition temperature 145° C.) of 3,5-dimethyl-4-hydroxystyrene and 4-hydroxystyrene (3:7),
2.0 g of distilled hexamethoxymethyl melamine,
0.02 g of tetramethyl ammonium hydroxide,
0.004 g of Megafac R-08 (tradename), and
42.4 g of propylene glycol monomethyl ether acetate.

To one of the base formulations, a solution of 0.35 g of (4-phenyl-thiophenyl) diphenyl sulfonium 3,3,3,2,1,1-hexafluoropropane sulfonate dissolved in 20 g of propylene glycol monomethyl ether acetate was added (Example 145), while the other base formulation,
0.35 g of (4-phenyl-thiophenyl) diphenyl sulfonium trifluoromethane sulfonate dissolved in 20 g of propylene glycol monomethyl ether acetate was added (Comparative Example 110).

The solutions thus obtained were filtered and spin coated onto HMDS treated silicon wafers at 2,400 rpm. After baking on a hot plate at 90° C. for 60 seconds, both materials yielded a film thickness of 1.06±0.03 μm.

The wafers were subjected to an exposure through a mask with fine lines and space patterns down to 0.20 μm using a Nikon NSR 1755i 7a i-line stepper at a dose of 82 mJ/cm$^2$. The exposed materials were then baked on a hot plate at 105° C. for 90 seconds and developed.

The material of the Example 145 resolved 0.28 μm lines and spaces patterns and the profile of the resist patterns were ideally rectangular. No whisker-like raised portions or scum were observed. The dose to print isolated lines with a width of 0.28 μm was found to be 91 mJ/cm$^2$.

The material of the Comparative Example 110 also resolved 0.28 μm lines and spaces patterns. However, the top of the line patterns was rounded, and the bottom of the line patterns had an undercut structure combined with severe scum. The dose to print isolated lines with a width of 0.28 μm was found to be 95 mJ/cm$^2$ and therefore this formulation was judged to be clearly inferior to that of the Example 145.

Example 149 and Comparative Example 111

From Example 104, it is evident that the replacement of triflate based PAGs with the hexaflate based PAGs of the present invention yields radiation sensitive compositions with identical sensitivity and resolution capability.

A quartz wafer (wafer 1) was coated with a solution containing a mixture of
5.0 g of poly-(4-hydroxystyrene), and
0.3 g of triphenyl sulfonium 3,3,3,2,1,1-hexafluoropropane sulfonate (Example 149, wafer 1) dissolved in
50 g of propylene glycol monomethyl ether actetate and baked at 120° C. for 60 seconds.

A second quartz wafer (wafer 2) was coated with a solution containing a mixture of
5.1 g poly-(4-hydroxystyrene), and
0.3 g triphenyl sulfonium triflate (Comparative Example 111, wafer 2) dissolved in
50 g propylene glycol monomethyl ether acetate and baked at 120° C. for 60 seconds.

In addition, two other quartz wafers (wafer 3 and wafer 4) were coated with a solution of
5.0 g poly-(4-t-butyloxycarbonyloxystyrene) dissolved in
50 g propylene glycol monomethyl ether acetate and baked at 90° C. for 90 seconds. Wafers 3 and 4 were subjected to a quantitative FIR spectrum analysis with respect to the intensity of the carbonyl bond. Then the film of wafer 3 was brought into intimate contact with the film of wafer 1 and the film of wafer 4 with the film of wafer 2 each at a pressure of about 0.05 kg/cm$^2$. Both wafer pairs were subjected to a flood irradiation with DUV KrF excimer laser irradiation at a dose of 80 mJ/cm$^2$ and baked at 90° C. for 90 seconds with wafers 3 and 4 on the upper side. The wafers 3 and 4 were separated from wafers 1 and 2 and their FIR spectra were again recorded. After substraction of the two spectra (before and after exposure/bake), it became evident that 47% of the t-butyloxycarbonyloxy groups of the polymer on wafer 4 had been cleaved into hydroxy groups by trifluoromethanesulfonic acid produced during exposure and diffusing into the polymer during the post exposure bake, while only 14% of the t-butyloxycarbonyloxy groups of the polymer on wafer 3 had been cleaved, indicating that the trifluoromethane sulfonic acid produced from wafer 2 was much more volatile than the 3,3,3,2,1,1-hexafluoropropanesulfonic acid produced from wafer 1. From this experiment, it can be concluded that the amount of acidic, corrosive and volatile products which might cause destruction of the irradiation equipment and pose hazards to the health of the workers is significantly reduced, when triflate generating PAGs were replaced with the PAGs of the present invention.

Example 150

The radiation sensitive composition of Example 141 was coated on a mechanically surface grained aluminum foil and dried to a weight of about 1.2 g/m$^2$. After imagewise exposure through a positive-working original with a 5 kW metal halide light source for 23 seconds, the foil was heated at 100° C. for 8 minutes in a convection oven. The printed image was developed with a developer solution containing the following ingredients by a plush paddle method:
5.0 g of sodium lauryl sulfate,
1.5 g of sodium metasilicate pentahydrate,
1.6 g of trisodium phosphate dodecahydrate, and
92.5 g of ion-exchanged water.

The plate was then rinsed with pure water and dried. Step 6 of a silver-film continuous-tone step having a density range from 0.05 to 3.05 and density increments of 0.15 was completely reproduced on the copy. Even the finest screens and lines of the original were clearly visible. The printing plate obtained in the manner described gave 32,000 high quality impressions on a sheetfed offset printing machine.

Example 151 and Comparative Example 112

Monodisperse poly-4-hydroxystyrene (Nippon Soda Co., Ltd., Mw=about 9,000, polydispersity=1.08) was reacted with ethylene vinyl ether in the presence of p-toluenesulfonic acid as a catalyst to prepare a copolymer of 4-hydroxystyrene and 4-(2-ethoxy)-ethoxystyrene. The copolymer had an average molecular weight of 10,500 as determined by GPC using polystyrene as the standard. The molar ratio of 4-hydroxystyrene:4-(2-ethoxy)-ethoxystyrene was about 6.9:3.1 as measured by $^1$H NMR. The following ingredients were mixed together to prepare two solutions of a positive-working chemically amplified radiation sensitive composition suitable for DUV (248 nm) exposure:

9.8 g of the above copolymer,
0.42 g of tris-4-t-butylphenyl sulfonium 3,3,3,2,1,1-hexafluoropropane sulfonate (Example 51) or
0.36 g of triphenyl sulfonium triflate (Comparative Example 112),
0.03 g of triethanolamine,
0.05 g of N,N-dimethylacetamide,
0.004 g of Megafac R-08 (tradename), and
64.2 g of propylene glycol monomethyl ether acetate.

The solutions thus obtained were filtered and spin coated on silicon covered with a phosphor-spin-on-glass (PSG) layer, which has been pretreated by a dehydration bake at 150° C., and baked on a hot plate at 95° C. for 90 seconds to yield a thin layer having a thickness of about 0.65 μm. The recording material was exposed as described in Example 101 (NA=0.55, σ=0.71) using a mask with contact hole patterns down to 0.15 μm at a dose of 52 mJ/cm$^2$ and baked for 90 seconds at 115° C. Next the material was developed as described in Example 101.

SEM inspection revealed that the recording material of the present invention resolved 0.18 μm contact holes at a duty ratio of 1:1 with a depth-of-focus (DOF) of about 1.40 μm. The side walls of the contact holes were vertical, and virtually no footing was observed at the resist/substrate interface. The comparative material resolved 0.20 μm contact holes with a depth-of-focus (DOF) of less than 0.8 μm.

Example 152 and Comparative Example 113

The following ingredients were mixed together to prepare two solutions of a positive-working chemically amplified radiation sensitive composition suitable for DUV (248 nm) exposure:

9.8 g of the above terpolymer (POLY 102),
0.4 g of tris-(4-t-butylphenyl)sulfonium 3,3,3,2,1,1-hexafluoropropane sulfonate (Example 152) or
0.35 g of triphenyl sulfonium triflate (Comparative Example 113),
0.03 g of triphenyl sulfonium acetate,
0.004 g of Megafac R-08 (tradename), and
64.2 g of propylene glycol monomethyl ether acetate.

The solution thus obtained was filtered, spin-coated on a HMDS treated silicon wafer and baked for 60 seconds on a hot plate at 135° C. to yield a thin layer having a thickness of about 0.82 μm. The recording material was exposed in the same manner as in Example 101. The dose was 29 mJ/cm$^2$ at which 1:1 lines and spaces of 0.25 μm were provided. The film was then baked at 135° C. for 90 seconds. For both the materials, subsequent development as described in Example 101 yielded resolved line and space patterns below 0.21 μm. SEM revealed that, for the material of the present invention, the linewidth of isolated and dense lines was almost equal, i.e. the iso to dense bias was negligible, whereas, for the comparative material, a large iso to dense bias existed in the lines. Further, for the material of the present invention, the isolated lines were free from dropouts of the film and resolved own to 0.12 μm. On the other hand, for the comparative material, here were dropouts of isolated lines of less than 0.14 μm from the substrate.

Synthesis Example 201

Preparation of diphenyl 4-t-butylphenyl sulfonium nonafluorobutane sulfonate (PAG 201)

A column having a length of 55 cm and an inner diameter of 5 cm was packed with 700 g of Amberlyst A-26 (tradename) dispersed in methanol in its chloride form. 3,000 ml of methanol was added to 3,000 ml of a 54% aqueous solution of tetramethyl ammonium hydroxide. This alkali solution was used to convert the chloride form of the Amberlyst ion-exchange resin to its hydroxide form. The column was then washed with methanol until the solution withdrawn from the column became neutral.

39.93 g (0.1 mol) of diphenyl 4-t-butylphenyl sulfonium bromide was dissolved in about 50 ml of methanol. The solution was passed through the column by elution with methanol at a rate of 30 ml/hour. The eluate was monitored using a potentiometer and occasionally tested for the absence of bromide ions using an aqueous silver nitrate solution. Next, the concentration of the hydroxyl group was determined by titration with 0.1 N HCl. The yield of diphenyl 4-t-butylphenyl sulfonium hydroxide was about 100%. The solution was adjusted to 1.0 mmol/g diphenyl 4-t-butylphenyl hydroxide.

With stirring, to 500 g (50 mmol) of the diphenyl 4-t-butylphenyl hydroxide was added dropwise 15.01 g (50 mmol) of distilled nonafluorobutane sulfonic acid diluted with 50 ml of methanol at room temperature. The mixture was stirred at room temperature for 24 hours. The solvent was removed by evaporation. The oil (30.9 g (about 100%)) thus obtained was crystallized to give pure diphenyl 4-t-butylphenyl sulfonium nonafluorobutane sulfonate. The purity was measured by HPLC and found to be >99%. $^1$H-NMR (CDCl$_3$): 1.44 (s, 9H, 4-t-butyl), 7.62–7.71 (m, 14H, aromatic) ppm.

Synthesis Example 202

Preparation of triphenyl sulfonium nonafluorobutane sulfonate (PAG 202)

91.03 g (0.45 mol) of diphenyl sulfoxide was dissolved in 1300 ml of benzene in a 2-liter three-neck round-bottom flask equipped with a stirrer, a thermometer, a dropping funnel, a condenser, and a nitrogen inlet. The mixture was cooled to 4° C. with vigorous stirring. A solution of 189.0 g (0.90 mol) of trifluoroacetic anhydride and 135.1 g (0.45 mol) of nonafluorobutane sulfonic acid was added dropwise thereto, while the temperature was maintained under ice cooling. After completion of the addition, the mixture was stirred for 1 hour. The temperature was returned room temperature, followed by stirring for additional 15 hours. After standing overnight, two separate phases were formed. The upper phase was removed and discarded. The oily bottom phase of approximately 500 ml volume was dropped into 2000 ml of diethyl ether, upon which a semi-crystalline deposit was formed. The ether was decanted, and the precipitate was dissolved in a minimum amount of dichloromethane. The solution was added dropwise to 1000 ml of vigorously stirred diethyl ether to reprecipitate the product. After completion of the addition, stirring was continued for 2 hours. After the solid was separated from diethyl ether, this procedure was repeated once more to enhance the crystallinity of the product. The mixture was filtered, and the semi-crystals were collected yielding 173.7 g of crude sulfonium salt. The melting point of the crude sulfonium salt was 75–78° C. Depending on the purity, the crystals can be either recrystallized from ethyl acetate or dissolved in the minimum amount of dichloromethane and purified by column chromatography on silica gel using a 95:5 dichloromethane-methanol mixture to perform purification. The first fractions containing unreacted diphenyl sulfoxide were discarded. After collection of the main fractions, the solvent was evaporated to leave 139.1 g (yield 58.7%) of triphenyl nonafluorobutane sulfonate as white crystals (m.p. 83–85.5° C.).

$^1$H-NMR (CDCl$_3$): δ=7.71–7.83 (m, 15H) ppm.

The purity was determined by HPLC analysis and found to be >97%.

Synthesis Example 203

Preparation of tris-(4-t-butylphenyl) sulfonium nonafluorobutane sulfonate (PAG 203)

48.18 g (0.15 mol) of bis-(4-t-butylphenyl) sulfoxide (prepared from diphenyl sulfide and t-butyl bromide via FeCl$_3$ catalyzed alkylation and subsequent oxidation with 2-chlorobenzoic acid) was dissolved in 400 ml of 4-t-butylbenzene in a 1-liter three-neck round-bottom flask equipped with a stirrer, a thermometer, a dropping funnel, a condenser and a nitrogen inlet. The mixture was cooled to 4° C. with vigorous stirring. A solution of 63.0 g (0.30 mol) of trifluoroacetic anhydride and 45.0 g (0.15 mol) of nonafluorobutane sulfonic acid was added dropwise thereto, while the temperature was maintained under ice cooling. After completion of the addition, the mixture was stirred for 1 hour. The temperature was returned to room temperature, followed by stirring for additional 15 hours. After standing overnight, two separate phases were formed. The upper phase was removed and discarded. The oily bottom phase of approximately 150 ml volume was diluted with 800 ml of diethyl ether, and washed twice with water and a sodium bicarbonate solution. The organic phase was dried over MgSO$_4$. After removal of the solvent, a semicrystalline solid was obtained. The semicrystalline solid was recrystallized from diethyl ether. Thus, 66.1 g (60.2%) of white crystals of tris-(4-t-butylphenyl) sulfonium nonafluorobutane sulfonate (m.p. 198–200° C.) was obtained.

$^1$H-NMR (CDCl$_3$): δ=1.36 (s, 27H), 7.81–7.88 (d, 12H) ppm.

The purity was determined by HPLC analysis and found to be >97%.

Synthesis Examples 204 to 208

The following sulfonium salts were synthesized in substantially the same manner as in the above synthesis examples.

Tris-(4-methylphenyl) sulfonium nonafluorobutane sulfonate (PAG 204)

$^1$H-NMR (CDCl$_3$): δ=2.42 (s, 9H), 7.37–7.47 (d, 12H) ppm.

The purity was determined by HPLC analysis and found to be >97%.

4-Methylphenyl-diphenyl sulfonium nonafluorobutane sulfonate (PAG 205)

$^1$H-NMR (CDCl$_3$): δ=2.45 (s, 3H), 7.40–7.55 (d, 14H) ppm.

The purity was determined by HPLC analysis and found to be >97%.

Bis-(4-methylphenyl)phenyl sulfonium nonafluorobutane sulfonate (PAG 206)

$^1$H-NMR (CDCl$_3$): δ=2.43 (s, 6H), 7.43–7.53 (d, 13H) ppm.

The purity was determined by HPLC analysis and found to be >97%.

Bis-(4-t-butylphenyl)-phenyl sulfonium nonafluorobutane sulfonate (PAG 207)

$^1$H-NMR (CDCl$_3$): δ=1.48 (s, 18H), 7.67–8.12 (m, 13H) ppm.

The purity was determined by HPLC analysis and found to be >97%.

4-Cyclohexylphenyl-diphenyl sulfonium nonafluorobutane sulfonate (PAG 208)

$^1$H-NMR (CDCl$_3$): δ=1.53–2.45 (m, 11H), 7.42–8.01 (m ,14H) ppm.

The purity was determined by HPLC analysis and found to be >97%.

Synthesis Example 209

Preparation of tris-(4-butoxyphenyl) sulfonium nonafluorobutane sulfonate (PAG 209)

To a stirred solution of 60.0 g (0.164 mol) of bis-(4-t-butoxyphenyl) sulfoxide in 26.8 g (0.34 mol) of pyridine and 400 ml of tetrahydrofuran was dropped 126.57 g (0.34 mol) of trimethylsilyl nonafluorobutane sulfonate while keeping the temperature below −5° C. with a salted ice bath. After completion of the addition, the reaction temperature was raised to 5° C., followed by stirring for additional 20 minutes. A Grignard solution was prepared from 8.4 g (0.34 mol) of magnesium, 100 g of tetrahydrofuran and 68.6 g (0.38 mol) of 4-t-butoxy chlorobenzene, and added dropwise to the above solution at 0° C. The mixture was stirred for 2 hours at this temperature. Then water was added to decompose the excess Grignard reagent, and the inorganic salts were removed by filtration. The solution was concentrated to about 160 ml and extracted with a mixture of 1200 ml of dichloromethane, 600 g of a saturated aqueous solution of ammonium chloride and 600 ml water. The organic phase was washed twice with water and dried. The solvent was removed to yield an oily product which was then purified by column chromatography on silica gel using dichloromethane as the eluant. Thus, tris-(4-butoxyphenyl) sulfonium nonafluorobutane sulfonate was obtained as a slightly yellowish powder. The structure was confirmed by $^1$H-NMR (CDCl$_3$) with δ=1.42 (s, 27H), 7.35–7.42 (d, 6H) and 7.78–7.93 ppm (d, 6H).

Synthesis Example 210

Preparation of tris-(4-t-butoxycarbonylmethoxyphenyl) sulfonium nonafluorobutane sulfonate (PAG 210)

A solution of 62.2 g (0.08 mol) of tris-(4-butoxyphenyl) sulfonium nonafluorobutane sulfonate and 2.40 g (0.008 mol) of nonafluorobutane sulfonic acid in 200 ml of ethanol was refluxed for 8 hours with stirring. After evaporation of the solvent, the crude product of tris-(4-hydroxyphenyl) sulfonium nonafluorobutane sulfonate (yield about 100%) was dissolved in 160 g of N,N-dimethylformamide and reacted with 55.4 g (0.40 mol) of anhydrous potassium carbonate and 60.3 g (0.40 mol) of t-butyl chloroacetate at 80° C. for 3 hours. The cooled reaction mixture was poured into 700 ml of water and extracted with dichloromethane. The organic phase was washed with water and dried. The solvent was removed. The oily residue was purified by column chromatography on silica gel using a dichloromethane and methanol as the eluent. The white product was collected to yield 34.4 g (yield 45%) of analytically pure tris-(4-t-butoxycarbonylmethoxyphenyl) sulfonium nonafluorobutane sulfonate. The $^1$H-NMR spectrum gave the following signals (CDCl$_3$): δ=1.45 (s, 27H), 4.76 (s, 6H), 7.15–7.18 (d, 6H). 7.74–7.87 (d, 6H).

Synthesis Example 211

Preparation of β-oxocyclohexyl 2-norbornylmethyl sulfonium nonafluorobutane sulfonate (PAG 211)

To a solution of 14.14 g (0.106 mol) of 2-chlorocyclohexane in 100 ml of ethanol was added dropwise 50 ml of a 15% solution of methylmercaptane sodium salt. The mixture was stirred for 3 hours. Then 600 ml water was added, and the mixture was extracted with dichloromethane. The organic phase was dried, and the solvent was removed to yield crude β-oxocyclohexyl methyl sulfide, which was purified by distillation (b.p. 45–47° C./0.3 mmHg).

2.0 g (15.6 mmol) of this product was dissolved in 10 ml of nitromethane and added dropwise with 20 g (114 mmol) of 2-bromonorbornane and stirred at room temperature for 1 hour. After that, a solution of 2.28 g (15.6 mmol) of silver nonafluorobutane sulfonate dissolved in 400 ml of nitromethane was added dropwise to the reaction mixture and stirred for three hours at room temperature. The silver bromide was removed by filtration. The filtrate was concentrated to 50 ml, and then added dropwise to 600 ml of diethyl ether. The precipitated solid was collected, washed with ether and recrystallized from ethyl acetate. The yield of β-oxocyclohexyl 2-norbornyl methyl sulfonium nonafluorobutane sulfonate was 1.88 g.
$^1$H-NMR (CDCl$_3$): δ=1.33–2.28 (m, 16H), 2.30–3.10 (m, 5H), 4.95–5.53 ppm (2m, 2H).

Synthesis Example 212

Preparation of bis-(4-cyclohexylphenyl) iodonium nonafluorobutane sulfonate (PAG 212)

A 500 ml three-neck round bottom flask equipped with a stirrer, a thermometer, a dropping funnel, a condenser, and a nitrogen inlet was charged with 43 g (0.20 mol) of potassium iodate, 69.2 g (0.43 mol) of cyclohexylbenzene and 43 ml acetic anhydride. The mixture was cooled to –5° C. A mixture of 43 ml of acetic anhydride and 30.1 ml concentrated sulfuric acid was added dropwise thereto with vigorous stirring. During the addition, the reaction temperature was kept below 5° C. After the end of the addition, the temperature of the reaction solution was returned to room temperature over a period of 2 to 3 hours. The resulting mixture was left for 48 hours and cooled to 5° C. 100 g of a 1:1 ice/water mixture was added with stirring. During this operation, the temperature of the reaction solution was kept below 10° C. Precipitated crystals of potassium salts were removed by filtration, and the precipitates were extracted twice with petroleum ether. To the remaining aqueous solution was added dropwise 45 g of ammonium bromide dissolved in 100 ml water with stirring. The precipitate of bis-(4-cyclohexylbenzene)iodonium bromide was isolated by filtration, washed, and dried.

15.26 g (28.5 mmol) of the bromide was dissolved in 100 ml of dichloromethane and 10.3 g (34.2 mmol) of nonafluorobutane sulfonic acid was added. The mixture was stirred at reflux for 6 hours. Hydrogen bromide evolved. After cooling, the reaction mixture was washed twice with a 2.5% aqueous solution of tetramethyl ammonium hydroxide and then dried. The solvent was then removed. The yellowish residue was recrystallized from an isopropanol/isopropyl ether mixture to give 12.2 g (63%) of bis-(4-cyclohexylphenyl) iodonium nonafluorobutane sulfonate.
$^1$H-NMR (CDCl$_3$): δ=1.12–1.75 (m, 22H), 7.23–7.90 (d, 8H) ppm.

The purity was determined by HPLC analysis and found to be >97%.

Synthesis Examples 213–215

The following iodonium salts were synthesized in substantially the same manner as in the above synthesis examples. Diphenyl iodonium nonafluorobutane sulfonate (PAG 213)
$^1$H-NMR (CDCl$_3$): δ=7.20–7.35 (m, 10H) ppm.

The purity was determined by HPLC analysis and found to be >97%.

Bis-(4-methylphenyl) iodonium nonafluorobutane sulfonate (PAG 214)

$^1$H-NMR (CDCl$_3$): δ=2.25 (s, 6H), 7.20–7.58 (d, 8H) ppm.

The purity was determined by HPLC analysis and found to be >97%.

Bis-(4-t-butylphenyl) iodonium nonafluorobutane sulfonate (PAG 215)

$^1$H-NMR (CDCl$_3$): δ=1.48 (s, 18H), 7.35–7.49 (d, 8H) ppm.

The purity was determined by HPLC analysis and found to be >97%.

Synthesis Example 216

Preparation of 4-methylphenyl phenyl iodonium nonafluorobutane sulfonate (PAG 216)

To a stirred suspension of 4.40 g (20 mmol) of iodosylbenzene in 100 ml of dichloromethane was added dropwise 6.0 g (20 mmol) of nonafluorobutane sulfonic acid at 0° C. under exclusion of moisture. The mixture was stirred at room temperature for 2 hours. The temperature was returned to 0° C. again. 1.84 g (20 mmol) of toluene was added dropwise. After the addition, stirring was continued at room temperature for additional 1 hour. The solvent as evaporated. The oily residue was dissolved in diethyl ether. The solution was cooled to obtain crystals of 4-methylphenyl phenyl iodonium nonafluorobutane sulfonate. The crystals were washed with hexane. The yield was 6.7 g.
$^1$H-NMR (CDCl$_3$): δ=2.25 (s, 3H), 7.18–7.58 (m, 9H) ppm.

The purity was determined by HPLC analysis and found to be >97%.

Example 201

A copolymer of 4-hydroxystyrene and 4-t-butyloxycarbonylstyrene was prepared by reacting monodisperse poly-4-hydroxystyrene with di-t-butylcarbonate. The copolymer had a molecular weight of 8,700 with a polydispersity of 1.18 as determined by GPC using polystyrene as the standard. The molar ratio of 4-hydroxystyrene:4-t-butyloxycarbonylstyrene was 7:3 as concluded from inspection of the $^1$H NMR spectrum (POLY 201). The following ingredients were mixed together to prepare a solution of a positive-working chemically amplified radiation sensitive composition suitable for DUV (248 nm) exposure:

9.8 g of the above copolymer,
0.3 g of tris(4-t-butylphenyl) sulfonium nonafluorobutane sulfonate,
0.02 g of tetramethyl ammonium hydroxide,
0.004 g of Megafac R-08 (tradename), and
64.2 g of propylene glycol monomethyl ether acetate.

The solution was filtered through a teflon filter having a pore diameter of 0.1 μm, spin coated on a silicon wafer pre-coated with DUV-18, an antireflective coating provided by Brewer Science at a film thickness of 115 nm (bake temperature: 200° C.), at 3,000 revolutions and dried at 90° C. for 60 seconds on a hot plate to remove the solvent. Thus, a 0.75 μm-thick film was obtained. The recording material thus obtained was imagewise exposed using a mask providing lines and spaces patterns down to 0.10 μm per image with a DUV stepper Nikon NSR 2005 EX 10B, having a numerical aperture (NA) of 0.55 during exposure and a coherence factor (σ) of 0.55 with a dose of 22 mJ/cm$^2$. The material was baked at 100° C. for 90 seconds to develop the latent image, and then processed at 23° C. by puddle development with AZ 300 MIF (tradename), a surfactant free developer containing 2.38% by weight of tetramethyl ammonium hydroxide provided by Clariant Japan K.K. A defect-free image of the mask with high edge stability was obtained, structures <0.25 μm being resolved faithfully to detail and the width ratio (linearity of the resist) of nominally equal lines/space structures being virtually constant in the range between 1.00 μm and 0.25 μm. In 250 nm image, the difference in linewidth between dense lines and isolated lines was not more than 5 nm, and the dense/iso bias was very small. The resist profile was almost vertical and very smooth, as neither line edge roughness nor standing waves were observed.

Example 202

Radical copolymerization of 4-acetoxystyrene, styrene and t-butylmethacrylate was carried out in the presence of 2,2-azo-bis-isobutyronitrile as a polymerization initiator, followed by hydrolysis of the acetate groups of the copolymer with an aqueous ammonium acetate solution to prepare a terpolymer of 4-hydroxystyrene, styrene and t-butyl methacrylate. The terpolymer had a molecular weight of 14,200 with a polydispersity of 1.69 as determined by GPC using polystyrene as the standard, and the molar ratio of 4-hydroxystyrene:styrene:t-butylmethacrylate was 7:2:1 as determined by $^1$H NMR (POLY 202). The following ingredients were mixed together to prepare a solution of a positive-working chemically amplified radiation sensitive composition suitable for DUV (248 nm) exposure:

9.8 g of the above copolymer,
0.3 g of bis-(4-t-butylphenyl) iodonium nonafluorobutane sulfonate,
0.03 g of triphenyl sulfonium acetate,
0.004 g of Megafac R-08 (tradename), and
64.2 g of propylene glycol monomethyl ether acetate.

The solution thus obtained was filtered, spin-coated on a HMDS treated silicon wafer and baked for 60 seconds on a hot plate at 130° C. to yield a film thickness of 0.82 μm. The recording material was exposed in the same manner as in Example 201. The dose was 30 mJ/cm$^2$. The film was then baked at 130° C. for 90 seconds. Subsequent development as described in Example 201 resolved line and space patterns below 0.22 μm. From scanning electron microscope (SEM) inspection, it was concluded that the linewidth of isolated and dense lines was almost equal, i.e. the dense to iso bias was negligible. Isolated line patterns were resolved down to 0.14 μm.

Example 203 and Comparative Examples 201 and 202

Radical polymerization of 4-t-butyloxystyrene was carried out in the presence of 2,2-azo-bis-isobutyronitrile as a polymerization initiator, followed by partial hydrolysis of the t-butyloxy groups with a concentrated aqueous hydrogen chloride solution to prepare 4-hydroxystyrene with 12% of the t-butyloxy groups being left intact. This copolymer was then reacted with ethyl vinyl ether in the presence of p-toluenesulfonic acid as a catalyst to prepare a terpolymer of 4-hydroxystyrene, 4-(1-ethoxyethoxy)styrene and 4-t-butoxystyrene. The terpolymer thus obtained had a molecular weight of 23,400 with a polydispersity of 2.14 as determined by GPC using polystyrene as the standard, and the molar ratio of 4-hydroxystyrene styrene:t-butyl methacrylate was 6.7:2.2:1.1 as measured by $^1$H NMR (POLY 203).

The following ingredients were mixed together to prepare solutions of a positive-working chemically amplified radiation sensitive composition suitable for DUV (248 nm) exposure:

9.8 g of the above copolymer,
0.3 g (0.41 mmol) of tris-(4-t-butylphenyl)sulfonium nonafluorobutane sulfonate (Example 203),
0.02 g of triphenyl sulfonium acetate,
0.05 g of 9-anthramethyl acetate (DUV absorber),
0.004 g of Megafac R-08 (tradename), and
64.2 g of propylene glycol monomethyl ether acetate.

For comparison, positive-working chemically amplified radiation sensitive composition solutions were prepared in the same manner as described just above, except that 0.27 g (0.41 mmol) of tris-(4-t-butylphenyl)sulfonium camphor sulfonate (Comparative Example 201) or 0.24 g (0.41 mmol) of tris-(4-t-butylphenyl)sulfonium phenylsulfonium trifluoromethane sulfonate (Comparative Example 202) was used instead of 0.3 g (0.41 mmol) of tris-(4-t-butylphenyl) sulfonium nonafluorobutane sulfonate.

The solutions were filtered, and spin-coated on three silicon wafers, which have been precoated with an experimental antireflective coating provided by Clariant Japan K.K. at a film thickness of 60 nm (bake temperature: 220° C.). The resist films were baked for 60 seconds on a hot plate at 90° C. to yield a film thickness of 0.75±0.02 μm.

The recording materials were exposed as described in Example 201 (NA=0.50, σ=0.50) and then baked at 105° C. for 60 seconds. Development was done as described in Example 201. The results were as follows.

TABLE 201

|  | Example 203 | Comparative Example 201 | Comparative Example 202 |
|---|---|---|---|
| Dose (mJ/cm$^2$) | 22 (1) | 31 (3) | 22 (1) |
| Dense Line Resolution ($\mu$m) | 0.17 (1) | 0.26 (3) | 0.18 (1) |
| Isolated Line Resolution ($\mu$m) | 0.15 (1) | 0.19 (2) | 0.20 (3) |
| Dense Line DOF @ 0.22 $\mu$m ($\mu$m) | 1.4 (1) | 0.0 (3) | 1.1 (2) |
| Isolated Line DOF @ 0.22 $\mu$m ($\mu$m) | 1.0 (1) | 0.6 (3) | 0.7–0.8 (2) |
| Dense/iso bias @ 0.22 $\mu$m ($\mu$m) | 9 (1) | Na (3) | 27 (2) |

Remarks

In the table, rating was added in parenthesis (1)=best, (2)=intermediate, (3)=poor.

The dose is defined as the exposure energy to delineate equal lines and spaces of 0.22 $\mu$m pattern width.

The dense line resolution is defined as the smallest equal lines and spaces patterns fully reproduced at that dose.

The isolated line resolution is defined as the smallest isolated line pattern without top film loss of the line at that dose.

The dense line DOF is defined as the depth of focus of equal lines and spaces at that dose.

The isolated line DOF is defined as the depth of focus of isolated lines at that dose.

The dense/iso bias is defined as the linewidth difference between dense lines and isolated lines at that dose.

These results clearly demonstrate that the material using the resist material of the present invention has the best lithographic performance among these three samples.

Example 204 and Comparative Examples 203 and 204

Monodisperse poly-4-hydroxystyrene (Nippon Soda Co., Ltd., Mw=12,000, polydispersity=1.16) was reacted with 2-chloroethyl vinyl ether in the presence of p-toluenesulfonic acid as a catalyst to prepare a copolymer of 4-hydroxystyrene and 4-(1-(2-chloroethoxy)ethoxy) styrene. The copolymer had a molecular weight of 13,700 with a polydispersity of 1.21 as determined by GPC using polystyrene as the standard, and the monomer ratio of 4-hydroxystyrene:4-(1-(2-chloroethoxy)ethoxy)styrene was 7.1:2.9 as measured by $^1$H NMR (POLY 204).

The following ingredients were mixed together to prepare three solutions of a positive-working chemically amplified radiation sensitive composition suitable for DUV (248 nm) exposure:

9.8 g of the above copolymer,
0.25 g of tris-(4-t-butylphenyl) sulfonium nonafluorobutane sulfonate (Example 204),
0.03 g of triphenyl sulfonium acetate,
0.004 g of Megafac R-08 (tradename), and
64.2 g of propylene glycol monomethyl ether acetate.

For comparison, positive-working chemically amplified radiation sensitive composition solutions were prepared in the same manner as described just above, except that 0.25 g of tris-(4-t-butylphenyl)sulfonium triflate (Comparative Example 203) or 0.25 g of tris-(4-t-butylphenyl)sulfonium propane sulfonate (Comparative Example 204) was used instead of 0.25 g of tris-(4-t-butylphenyl) sulfonium nonafluorobutane sulfonate. The solutions were filtered, spin coated on two HMDS treated silicon wafers each (total 6 wafers), baked for 90 seconds on a hot plate at 110° C. to yield a layer having a thickness of 0.75±0.02 $\mu$m. The recording material was exposed as described in Example 201 (NA=0.55, σ=0.55). The dose was as indicated in Table 202. While one of each wafer was placed immediately on a hot plate and baked for 90 seconds at 75° C. (Test A), the second wafers were stored in the clean room for 60 minutes and then baked under the same conditions (Test B). Next, these wafers were developed as described in Example 201. The results are compiled in Table 202.

TABLE 202

|  | Example 204 | Comparative Example 203 | Comparative Example 204 |
|---|---|---|---|
| Test A |  |  |  |
| Dose (mJ/cm$^2$) | 24 (2) | 22 (1) | 37 (3) |
| Dense Line Resolution ($\mu$m) | 0.17 (1) | 0.17 (1) | 0.21 (2) |
| Isolated Line Resolution ($\mu$m) | 0.15 (1) | 0.15 (1) | 0.19 (2) |
| Dense Line DOF @ 0.22 $\mu$m ($\mu$m) | 1.4–1.5 (1) | 1.1 (2) | 1.1 (2) |
| Isolated Line DOF @ 0.22 $\mu$m ($\mu$m) | 1.0 (1) | 0.6 (3) | 0.7–0.8 (2) |
| Dense/iso bias @ 0.22 $\mu$m (nm) | 17 (1) | 30 (3) | 27 (2) |
| T-top | None (1) | None (1) | None (1) |
| Test B (after one hour) |  |  |  |
| Dose (mJ/cm$^2$) | 24 (1) | 23 (2) | 34 (3) |
| Dense Line Resolution ($\mu$m) | 0.17 (1) | 0.18 (2) | 0.22 (3) |
| Isolated Line Resolution ($\mu$m) | 0.15 (1) | 0.16 (2) | 0.21 (3) |
| Dense Line DOF @ 0.22 $\mu$m ($\mu$m) | 1.4–1.5 (1) | 0.9 (2) | 0.6 (3) |
| Isolated Line DOF @ 0.22 $\mu$m ($\mu$m) | 1.0 (1) | 0.4 (3) | 0.6 (2) |
| Dense/iso bias @ 0.22 $\mu$m (nm) | 15 (1) | 37 (3) | 32 (2) |
| T-top | None (1) | Yes, slight | Yes, medium |

Remarks

The definition of the test items is the same as given in Example 203. T-top indicates formation of an insoluble phase on top of the resist.

These results demonstrate superior performance of the resist material of the present invention (Test A) and superiority in dimensional stability upon delay time changes (Test B).

Example 205

Monodisperse poly-4-hydroxystyrene (manufactured by Nippon Soda Co., Ltd., Mw=2,000, polydispersity=1.16) was reacted with dihydropyran and a minor amount of α, ω-triethylene glycol divinyl ether in the presence of p-toluenesulfonic acid to prepare a copolymer of 4-hydroxystyrene and 4-tetrahydropyranyloxystyrene partially crosslinked by α, ω-triethylene glycol divinyl ether. The copolymer had an average molecular weight of 7,500 with an essentially trimodal molecular weight distribution at about 2,300, 4,600 and 7,000 and a minor amount of higher crosslinked parts as determined by GPC with polystyrene as the standard, and the monomer ratio of 4-hydroxystyrene:4-tetrahydropyranyloxystyrene was roughly 6.9:3.1 as measured by $^1$H NMR (POLY 205).

The following ingredients were mixed together to prepare a solution of a positive-working chemically amplified radia tion sensitive composition suitable for DUV (248 nm) exposure:
9.8 g of the above copolymer,
0.42 g of t-butyloxycarbonylphenyl diphenyl sulfonium nonafluorobutane sulfonate,
0.03 g of tri-n-octylamine,
0.05 g of N,N-dimethylacetamide,
0.004 g of Megafac R-08 (tradename), and
64.2 g of propylene glycol monomethyl ether acetate.

The solution was filtered, spin coated on a silicon wafer covered with a phosphor-spin-on-glass layer, which has been pretreated bake at 150° C., and baked for 90 seconds on a hot plate at 115° C. to yield a layer having a thickness of 0.65 µm. The recording material was exposed as described in Example 201 (NA=0.55, σ=0.71) using a mask with contact hole patterns down to 0.15 µm at a dose of 62 mJ/cm² and baked for 90 seconds at 120° C. Next the material was developed as described in Example 201. Scanning electron microscope (SEM) inspection revealed that the recording material resolved 0.19 µm contact holes at a duty ratio of 1:1 with a usable depth-of-focus (DOF) of about 0.7 µm. The sidewalls of the contact holes were vertically, and virtually no footing was observed at the resist/substrate interface.

Example 206

Monodisperse poly-4-hydroxystyrene (manufactured by Nippon Soda Co., Ltd., Mw=8,000, polydispersity=1.09) was reacted with ethyl vinyl ether in the presence of p-toluenesulfonic acid as a catalyst to prepare a copolymer. The copolymer was reacted with di-t-butylcarbonate in the presence of triethylamine to prepare a terpolymer of 4-hydroxystyrene, 4-(1-ethoxyethoxystyrene) and 4-(t-butyloxycarbonyloxystyrene). The terpolymer had an average molecular weight of 10,200 with a polydispersity of 1.13 as determined by GPC using polystyrene as the standard, and the monomer ratio of 4-hydroxystyrene:4-(1-ethoxyethoxy)styrene:4-t-butyloxycarbonyloxystyrene was 6.5:3.8:0.7 as measured by $^1$H NMR (POLY 206).

The following ingredients were mixed together to prepare a solution of a positive-working chemically amplified radiation sensitive composition suitable for DUV (248 nm) exposure:
9.8 g of the above terpolymer,
0.35 g of bis-(4-cyclohexylphenyl) phenyl sulfonium nonafluorobutane sulfonate,
0.02 g of tetrabutyl ammonium hydroxide,
0.02 g of N,N-dicyclohexylamine,
0.004 g of Megafac R-08 (tradename), and
64.2 g of ethyl lactate.

The solution thus obtained was filtered, spin-coated on a HMDS treated silicon wafer and baked for 90 seconds on a hot plate at 100° C. to yield a layer having a thickness of 0.55 µm. The recording material was exposed as described in Example 201 (NA=0.55, σ=0.71) using a mask with contact hole patterns down to 0.15 µm at a dose of 55 mJ/cm² and baked for 90 seconds at 120° C. Next the material was developed as described in Example 201. Exposure was performed as described in Example 201 using NA=0.50 and a σ-value=0.60 at a dose of 26 mJ/cm². The material was baked for 90 seconds at 105° C., and developed with the surfactant-free developer of Example 201 for 60 seconds at 23° C. followed by water rinsing.

The material resolved dense lines and spaces patterns down to 0.18 µm and isolated lines down to 0.14 µm. The pattern shape was rectangular and no standing waves were observed. The DOF of the isolated patterns was larger than 1.0 µm for 0.18 µm features.

Examples 207 and 208

Radical copolymerization of 4-acetoxystyrene with 4-t-butylacrylate was carried out in the presence of 2,2'-azobis-(4-dimethoxy-2,4-dimethylvaleronitrile) as a polymerization initiator, followed by hydrolysis of the acetate groups with an aqueous ammonium acetate solution. A part of the hydroxy groups in the copolymer thus obtained were reacted with ethyl vinyl ether in the presence of p-toluenesulfonic acid as a catalyst to prepare a terpolymer of 4-hydroxystyrene, 4-(1-ethoxyethoxystyrene) and 4-t-butylacrylate. The terpolymer had an average molecular weight of 8,700 with a polydispersity of 1.71 as determined by GPC using polystyrene as the standard, and the molar ratio of 4-hydroxystyrene:4-(1-ethoxyethoxy)styrene:4-t-butylacrylate was 7.1:1.8:1.1 as measured by $^1$H NMR (POLY 207). The following ingredients were mixed together to prepare a solution of a positive-working chemically amplified radiation sensitive composition suitable for DUV (248 nm) and e-beam exposure:
9.8 g of the above terpolymer,
0.28 g of bis-(4-cyclohexylphenyl) iodonium nonafluorobutane sulfonate,
0.03 g of triphenyl sulfonium hydroxide,
0.004 g of Megafac R-08 (tradename), and
64.2 g of propylene glycol monomethyl ether acetate.

The solution was filtered, spin-coated on two HMDS treated silicon wafers and baked on a hot plate for 90 seconds at 110° C. to yield a layer having a thickness of 0.53 µm. One of the recording materials was exposed with excimer laser radiation provided by a Nikon NSR 2005 EX 10B stepper with an NA=0.55 and a coherence factor σ=0.80 using a mask with lines and spaces patterns down to 0.10 µm at a dose of 22 mJ/cm². The other recording material was pattern-wise exposed with e-beam radiation provided from a JEOL JBXX 5DII operating at 50 keV with a spot size of 10 nm (no proximity correction) at a dose of 16.2 µC/cm². The exposed wafers were placed on a hot plate and baked for 90 seconds at 120° C. The materials were then developed with AZ® MIF 300, a surfactant free developer containing 2.38% by weight of tetramethyl ammonium hydroxide provided by Clariant Japan K.K. for 60 seconds at 23° C. followed by pure water rinsing. The excimer laser exposed material resolved dense lines and spaces patterns down to 0.18 µm and isolated lines and spaces down to 0.14 µm. The pattern shape was rectangular and only minor standing waves were observed. The DOF of the isolated patterns was larger than 1.0 µm for 0.16 µm features.

The e-beam exposed material resolved dense lines and spaces down to 0.16 µm and isolated lines down to 0.11 µm. The DOF of the isolated patterns was larger than 1.0 µm for 0.15 µm features.

Examples 209 and 210

A terpolymer of a 4-hydroxystyrene derivative, 4-(t-butoxystyrene) and 4-t-butylcarbonylmethyloxy styrene was prepared by acid hydrolysis of monodisperse poly-4-t-butoxystyrene to leave 15% of the butoxy groups intact. A part of the hydroxy groups in the copolymer were reacted with t-butyl bromoacetate in the presence of triethylamine as a catalyst. The terpolymer had an average molecular weight of 8,700 with a polydispersity of 1.06 as determined by GPC using polystyrene as the standard, and the molar ratio of 4-hydroxystyrene:4-(t-butoxystyrene:4-t-butylcarbonyloxystrene was 7.1:1.4:1.5 as measured by $^1$H NMR (POLY 208).

The following ingredients were mixed together to prepare a solution of a positive-working chemically amplified radiation sensitive composition suitable for DUV (248 nm) and x-ray exposure:

9.8 g of the above terpolymer,
0.2 g of bis-(t-butylcarbonylmethyloxyphenyl) iodonium nonafluorobutane sulfonate,
0.15 g of tris-(t-butylcarbonylmethyloxyphenyl) sulfonium nonafluorobutane sulfonate,
0.03 g of tributylammonium pyrovate,
0.004 g of Megafac R-08 (tradename), and
64.2 g of methyl amyl ketone.

The solution was filtered, spin-coated on two HMDS treated silicon wafers and baked on a hot plate (90 sec/100° C.) to yield a layer having a thickness of 0.72 µm. One of the recording materials was exposed with excimer laser radiation provided by a Nikon NSR 2005 EX 10B stepper (NA=0.55, σ=0.55) using a mask with lines and spaces patterns down to 0.10 µm at a dose of 25 mJ/cm². The other recording material was patternwise exposed with x-ray radiation provided by a 0.6 GeV superconducting beam storage ring with a peak wavelength of 7.5 A using a Karl Suss XRS-200/3 stepper with a proximity gap of 30 µm at a dose of 70 mJ/cm². The x-ray mask had lines and spaces pattern down to 100 nm and was composed of 0.5 µm thick W-Ti absorber on a 2.0 µm thick SiC membrane. The exposed wafers were baked for 90 seconds at 110° C. and developed as described in Example 201.

The excimer laser exposed material resolved dense lines and spaces patterns down to 0.16 µm but the isolated lines were somewhat unstable and collapsed at geometries below 0.18 µm. The pattern shape was rectangular and only minor standing waves were observed. The DOF of the isolated patterns was larger than 1.0 µm for 0.16 µm features.

The x-ray exposed material resolved dense lines and spaces down to 0.14 µm and isolated lines down to 0.14 µm. At smaller geometries the patterns tended to collapse. The DOF of the isolated patterns was larger than 1.0 µm for 0.15 µm features.

Example 211

The following ingredients were mixed together to prepare a solution of a positive-working chemically amplified radiation sensitive composition suitable for DUV (248 nm) exposure:
9.8 g of the terpolymer described in Example 207 (POLY 207),
0.8 g of 4,4'-(1-methylethylidene) bis-[4,1-phenyleneoxy acetic acid] di(1,1-dimethylethyl) ester,
0.2 g of bis-(4-cyclohexylphenyl) phenyl sulfonium nonafluorobutane sulfonate,
0.03 g of triphenyl sulfonium hydroxide,
0.05 g of a condensation product of 2 moles 9-anthrylmethanol reacted with 1 mole toluene-1,3-diisocyanate (DUV absorber),
0.004 g of Megafac R-08 (tradename), and
64.2 g propylene glycol monomethyl ether acetate.

The solution was filtered, spin-coated on a HMDS treated silicon wafer and baked on a hot plate (90 sec/100° C.) to yield a layer having a thickness of 0.55 µm, exposed as described previously (NA=0.55) at a dose of 35 mJ/cm², baked for 90 seconds at 120° C. and developed.

The material resolved dense lines and spaces patterns down to 0.16 µm and isolated lines down to 0.14 µm. The pattern shape was rectangular and only minor standing waves were observed. The DOF of the isolated patterns was about 0.6 µm for 0.16 µm features.

Examples 212 and 213

4-Hydroxystyrene, tetracyclododecyl methacrylate, t-butyl methacrylate and methacrylic acid 2-tetrahydropyranyl ester was radically polymerized in the presence of 2,2'-azobis(isobutyronitrile) as a polymerization initiator to prepare a quaterpolymer. The quaterpolymer had an average molecular weight of 13,200 with a polydispersity of 2.4 as determined by GPC using polystyrene as the standard, and the monomer ratio of the components was 1.5:3.5:2.5:2.5 as measured by $^1$H NMR (POLY 209).

The following ingredients were mixed together to prepare a solution of a positive-working chemically amplified radiation sensitive composition suitable for DUV (248 nm) exposure and VDUV (193 nm) exposure:
7.8 g of the quaterpolymer described above,
2.8 g of 4,4'-(1-methylethylidene) bis-[4,1-cyclohexyleneoxy acetic acid] di(1,1-dimethylethyl) ester,
0.2 g of bis-(4-cyclohexylphenyl) iodonium nonafluorobutane sulfonate,
0.03 g of triethanolamine,
0.004 g of Megafac R-08 (tradename), and
64.2 g of propylene glycol monomethyl ether acetate.

The solution was filtered, spin-coated on two silicon wafers pretreated with AZ® KrF-2, a commercially available antireflective coating available from Clariant Japan K.K, baked for 90 seconds at 120° C. to yield a layer having a thickness of 00.55±0.02 µm, and one wafer was exposed as described in Example 201 (NA=0.55, σ=0.80) at a dose of 26 mJ/cm², while the other wafer was exposed with an ISI ArF stepper with a NA=0.60 and a σ=0.75 at a dose of 12.5 mJ/cm². The exposed wafers were baked for 90 seconds at 125° C. and developed.

The KrF excimer laser exposed material resolved dense lines and spaces patterns below 0.16 µm, isolated lines down to 0.14 µm, but both with a slight tendency to form T-tops. The ArF excimer laser exposed material showed the same resolution and pattern characteristics as the KrF excimer laser exposed material, however, the DOF of 0.18 µm lines exceeded that of the KrF exposed material by 25%.

Examples 214–237

The following radiation sensitive compositions were prepared and processed according to the steps indicated in Table 203, where
"Polymer" denotes the polymer used,
"PAG" denotes the PAG (photoacid generator) used,
"DissInh" denotes the dissolution inhibitor used,
"Base" denotes the basic additive used,
"Solv" denotes the solvent used,
"Ratio" denotes the component ratio in parts by weight used,
"Substrate" denotes the substrate to be coated with the radiation sensitive composition used,
"PB" denotes the applied prebake conditions (temperature/time),
"FT" denotes the film thickness of the radiation sensitive composition used,
"Exposure Type" denotes the radiation wavelength employed (ArF=193 nm excimer laser, KrF=248 nm excimer laser, i-line=365 nm quartz lamp, e-beam=30 keV electron beams, x-ray=1.3 nm),
"Dose" denotes the applied exposure dose (in mJ/cm² for ArF, KrF, I-line and x-rays and in µC/cm² for e-beam),
PEB denotes the applied post exposure bake conditions (temperature/time),
"Dev" denotes conditions for development (temperature/time) with an aqueous 2.38% tetramethyl ammonium hydroxide solution,
"Res" denotes the resolution capability of dense 1:1 lines and spaces,
"Delay Stability" denotes the linewidth change <10% upon delay between exposure and post exposure bake,
"Profile Angle" denotes the angle between the substrate and the sidewall of 0.25 µm line patterns, and
"DOF" denotes the depth of focus of 0.25 µm lines.

TABLE 203

| EXAMPLE # | 214 | 215 | 216 | 217 | 218 | 219 |
|---|---|---|---|---|---|---|
| Polymer | POLY 210 | POLY 210 | POLY 210 | POLY 211 | POLY 211 | POLY 211 |
| PAG | PAG 202 | PAG 202 | PAG 217 | PAG 204 | PAG 218 | PAG 210 |
| DissInh | — | DISS 201 | — | — | — | DISS 202 |
| Base | BASE 201 | BASE 201 | BASE 207 | BASE 202 | BASE 207 | BASE 203 |
| Solvent | SOLV 201 | SOLV 292 | SOLV 201 | SOLV 201 | SOLV 201 | SOLV 203 |
| Ratio (ppw) | 11.5/0.3/ 0.0/0.04/ 84.7 | 13.0/0.3/ 2.11/0.05/ 85.8 | 14.5/0.7/ 0.0/0.03/ 86.0 | 14.0/0.4/ 0.0/0.02/ 85.1 | 13.7/0.31 0.01/0.03/ 85.5 | 13.2/0.8/ 2.2/0.03/ 84.4 |
| Substrate | Si | BARC 201 | BARC 201 | BARC 202 | BARC 202 | BARC 202 |
| PB [° C./sec] | 90/60 | 90/60 | 90/60 | 110/60 | 135/60 | 135/60 |
| FT [μm] | 0.75 | 0.67 | 0.75 | 0.75 | 0.75 | 0.75 |
| Exposure Type | KrF | KrF | KrF | KrF | KrF | KrF |
| Dose [mJ/cm$^2$] | 39 | 35 | 40 | 29 | 27 | 35 |
| PEB [° C./sec] | 105/90 | 115/90 | 105/90 | 120/90 | 135/90 | 135/90 |
| Dev [° C./sec] | 23/60 | 23/60 | 23/60 | 23/60 | 23/60 | 23/60 |
| Res [μm] | 0.18 | 0.19 | 0.17 | 0.19 | 0.18 | 0.18 |
| Delay Stability [hrs] | >3 | >3 | >4 | >3 | >4 | >4 |
| Profile Angle [°] | >86 | >87 | >86 | >86 | >86 | >86 |
| DOF @ 0.25 μm [μm] | 1.20 | 1.30 | 1.20 | 1.25 | 1.30 | 1.25 |

| EXAMPLE # | 220 | 221 | 222 | 223 | 224 | 225 |
|---|---|---|---|---|---|---|
| Polymer | POLY 212 | POLY 213 | POLY 214 | POLY 214 | POLY 215 | POLY 216 |
| PAG | PAG 222 | PAG 225 | PAG 202 | PAG 204 | PAG 226 | PAG 223 |
| DissInh | — | DISS 201 | — | — | — | DISS 202 |
| Base | BASE 207 | BASE 207 | BASE 207 | BASE 204 | BASE 206 | BASE 207 |
| Solvent | SOLV 201 | SOLV 202 | SOLV 201 | SOLV 201 | SOLV 201 | SOLV 201 |
| Ratio | 16.0/0.4/ 0.0/0.05/ 83.5 | 13.1/0.1/ 0.8/0.04/ 85.9 | 14.3/0.41 0.0/0.1/ 85.0 | 14.7/0.31 0.0/0.03/ 84.5 | 13.9/0.7/ 0.0/0.03/ 85.3 | 12.2/0.4/ 1.4/0.03/ 85.6 |
| Substrate | BARC 201 | Si | BARC 201 | BARC 203 | BARC 205 | BARC 201 |
| PB [° C./sec] | 90/60 | 110/60 | 90/60 | 110/60 | 115/60 | 115/60 |
| FT [μm] | 0.75 | 0.67 | 0.55 | 0.75 | 0.52 | 0.70 |
| Exposure Type | KrF | e-beam | KrF | KrF | ArF | KrF |
| Dose [mJ (μC)/cm$^2$] | 40 | 18.2 | 42 | 31 | 12 | 53 |
| PEB [° C./sec] | 105/90 | 125/90 | 105/90 | 110/90 | 125/90 | 115/90 |
| Dev [° C./sec] | 23/60 | 23/60 | 23/60 | 23/60 | 23/20 | 23/60 |
| Res [μm] | 0.18 | 0.15 | 0.17 | 0.19 | 0.15 | 0.18 |
| Delay Stability [hrs] | >3 | >3 | >4 | >3 | >1 | >4 |
| Profile Angle [°] | >86 | >87 | >86 | >86 | >86 | >86 |
| DOF @ 0.25 μm [μm] | 1.20 | >1.30 | 1.20 | 1.25 | 1.30 | 1.25 |

| EXAMPLE # | 226 | 227 | 228 | 229 | 230 | 231 |
|---|---|---|---|---|---|---|
| Polymer | POLY 217 | POLY 218 | POLY 218 | POLY 215 | POLY 219 | POLY 220 |
| PAG | PAG 225/ 220 | PAG 202 | PAG 201 | PAG 224 | PAG 204 | PAG 210 |
| DissInh | — | — | DISS 203 | — | — | DISS 204 |
| Base | BASE 207 | BASE 201 | BASE 205 | BASE 203 | BASE 202 | BASE 204 |
| Solvent | SOLV 201 | SOLV 202 | SOLV 201 | SOLV 201 | SOLV 201 | SOLV 203 |
| Ratio | 14.3/0.8/ 0.0/0.1/ 87.0 | 16.5/0.4/ 0.0/0.04/ 83.5 | 16.1/0.1/ 0.8/0.04/ 85.9 | 14.3/0.4/ 0.0/0.1/ 85.0 | 14.7/0.2/ 0.0/0.03/ 84.5 | 17.9/0.5/ 0.0/0.03/ 85.3 |
| Substrate | Si | BARC 204 | BARC 201 | BARC 205 | BARC 201 | Si |
| PB [° C./sec] | 110/60 | 115/60 | 135/60 | 135/60 | 110/60 | 90/60 |
| FT [μm] | 0.75 | 0.67 | 0.75 | 0.45 | 0.65 | 0.75 |
| Exposure Type | x-ray | KrF | KrF | ArF | KrF | i-line |
| Dose [mJ (μC)/cm$^2$] | 75 | 36 | 39 | 17 | 42 | 88 |
| PEB [° C./sec] | 125/90 | 125/90 | 135/90 | 135/90 | 120/90 | 100/90 |
| Dev [° C./sec] | 23/60 | 23/60 | 23/60 | 23/60 | 23/60 | 23/60 |
| Res [μm] | 0.12 | 0.17 | 0.19 | 0.15 | 0.18 | 0.24 |
| Delay Stability [hrs] | >3 | >3 | >4 | >3 | >4 | >4 |
| Profile Angle [°] | >86 | >87 | >86 | >86 | >86 | >86 |
| DOF @ 0.25 μm [μm] | >1.60 | 1.20 | 1.15 | 1.45 | 1.30 | 1.25 |

| EXAMPLE # | 232 | 233 | 234 | 235 | 236 | 237 |
|---|---|---|---|---|---|---|
| Polymer | POLY 210 | POLY 216 | POLY 221 | POLY 211 | POLY 211 | POLY 220 |
| PAG | PAG 202 | PAG 226 | PAG 224 | PAG 219 | PAG 202 | PAG 210 |
| DissInh | — | DISS 201 | — | — | — | DISS 202 |
| Base | BASE 201 | BASE 201 | BASE 203 | BASE 202 | BASE 203 | BASE 204 |
| Solvent | SOLV 201 | SOLV 202 | SOLV 201 | SOLV 201 | SOLV 201 | SOLV 203 |
| Ratio (ppw) | 16.3/0.4/ 0.0/0.1/ 85.3 | 16.2/0.71 0.0/0.02/ 83.5 | 15.8/0.1/ 0.8/0.04/ 85.9 | 14.3/0.4/ 0.0/0.1/ 85.0 | 14.7/0.4/ 0.0/0.03/ 84.5 | 17.9/0.5/ 0.0/0.03/ 85.3 |
| Substrate | BARC 201 | Si | BARC 205 | BARC 202 | BARC 201 | Si |
| PB [° C./sec] | 90/60 | 90/60 | 125/60 | 110/60 | 135/60 | 95/60 |

TABLE 203-continued

| FT [μm] | 0.77 | 0.67 | 0.45 | 0.57 | 0.68 | 0.85 |
|---|---|---|---|---|---|---|
| Exposure Type | KrF | x-ray | ArF | KrF | KrF | i-line |
| Dose [mJ/cm$^2$] | 32 | 59 | 9 | 28 | 23 | 91 |
| PEB [° C./sec] | 105/90 | 115/90 | 115/90 | 120/90 | 135/90 | 100/90 |
| Dev [° C./sec] | 23/60 | 23/60 | 23/60 | 23/60 | 23/60 | 23/60 |
| Res [μm] | 0.20 | 0.15 | 0.14 | 0.19 | 0.18 | 0.26 |
| Delay Stability [hrs] | >3 | >3 | >2 | >3 | >4 | >4 |
| Profile Angle [°] | >86 | >87 | >86 | >86 | >86 | 86 |
| DOF @ 0.25 μm [μm] | 1.15 | >1.60 | 1.30 | 1.25 | 1.35 | — |

The following abbreviations were used for the ingredients shown in the table.
POLY 201 to POLY 209=see the above examples
POLY 210=poly-(4-hydroxystyrene-co-4-(1-ethoxyethoxy)styrene), 6.7:3.3; Mw=8,700; D=1.12;
POLY 211=poly-(4-hydroxystryene-co-t-butylmethacrylate); 7.2:2.8; Mw=11,400; D=1.86;
POLY 212=poly-(4-hydroxystyrene-co-4-(1-ethoxyisopropoxy)styrene; 6.9:3.1; Mw=8,200; D=1.14;
POLY 213=poly-(3-hydroxystyrene-co-4-t-butyl vinylphenoxyacetate); 6.8:3.2; Mw=15,200, D=2.21;
POLY 214=poly-(4-hydroxystyrene-co-4-(1-ethoxyethoxy)styrene-co-4-methylstyrene); 6.0:3.2 0.8; Mw=14,000; D=1.84;
POLY 215=poly-(4-hydroxystyrene-co-8-methyl-8-t-butoxycarbonyltetracyclo[4.4.0.1$^{2.5}$.1$^{7.10}$]dodec-3-ene-co-maleic anhydride); 1:4:5; Mw=4,800; D=2.45;
POLY 216=poly-(4-hydroxystyrene-co-4-(1-ethoxyethoxy)styrene-co-4-tetrahydropyranyloxystyrene); 6.5:2.5:1.0; Mw=9,400; D=1.18;
POLY 217=poly-(4-hydroxystyrene-co-styrene-co-4-t-butyl vinylphenoxyacetate); 6.0:2.0:2.0; Mw=12,300; D=1.72;
POLY 218=poly-(4-hydroxystyrene-co-4-t-butyloxycarbonyloxystyrene-co-t-butylmethacrylate); 6.8:2.1:1.1; Mw=7,200, D=1.65;
POLY 219=poly-(-4-hydroxystyrene-co-4-butoxystyrene-co-4-(1-ethoxyethoxy)styrene-co-4-vinylbenoic acid t-butylester); 7.0:1.2:1.3:0.5; Mw=11,300, D=2.25;
POLY 220=poly-(4-hydroxystyrene-co-2-hydroxystyrene); 2:8; Mw=9,200, D=1.85;
POLY 221=poly-(2-hydroxystyrene-co-2-methyl-adamantyl methacrylate-co-mevalonyl methacrylate); 1:6:3; Mw=7,700, D=2.17;
PAG 201 to PAG 216=see the above synthesis examples
PAG 217=bis-(4-butoxyphenyl diphenyl sulfonium nonafluorobutane sulfonate,
PAG 218=bis-(4-methylphenyl) phenyl sulfonium nonafluorobutane sulfonate,
PAG 219=tris-(4-chlorophenyl) sulfonium nonafluorobutane sulfonate,
PAG 220=tris-(t-butyloxycarbonyloxyphenyl) nonafluorobutane sulfonate,
PAG 221=phenyl dimethyl sulfonium nonafluorobutane sulfonate,
PAG 222=4-hydroxy-3,5-dimethylphenyl diphenyl sulfonium nonafluorobutane sulfonate,
PAG 223=2-naphthylcarbonylmethyl dimethyl nonafluorobutane sulfonate,
PAG 224=di-(4-t-butyloxyphenyl) iodonium nonafluorobutane sulfonate,
PAG 225=di-(4-t-butylcarbonylmethyloxyphenyl) nonafluorobutane sulfonate,
PAG 226=4-t-butylphenyl phenyl iodonium nonafluorobutane sulfonate,
DISS 201=4,4'-(1-phenylethylidene)-bis-[4,1-phenyleneoxy acetic acid]-di-(1,1-dimethylethyl)ester,
DISS 202=ethylidene tris-[4,1-phenyleneoxy acetic acid]-tris-(1,1-dimethylethyl)ester,
DISS 203=(1-methylethylidene)-di-4,1-phenylene-bis-(1,1-dimethylethyl)carbonic acid ester,
DISS 204=ethylidene-tris-4,1-phenylene-tris-(1,1-dimethylethyl)carbonic acid ester,
BASE 201=tetramethyl ammonium hydroxide,
BASE 202=tetra-n-butyl ammonium hydroxide,
BASE 203=tetra-n-butyl ammonium lactate,
BASE 204=methyldicyclohexylamine,
BASE 205=tri-n-octylamine,
BASE 206=triethanolamine,
BASE 207=triphenyl sulfonium acetate,
SOLV 201=propylene glycol monomethyl ether acetate,
SOLV 202=ethyl lactate,
SOLV 203=methyl amyl ketone,
BARC 201=DUV BARC AZ® KrF-3B® (available from Clariant Japan K.K.),
BARC 202=DUV BARC CD-9® (available from Brewer Science),
BARC 203=DUV BARC DUV18® (available from Brewer Science),
BARC 204=DUV BARC DUV42® (available from Brewer Science),
BARC 205=i-line BARC AZ® BarLi® II (available from Clariant Japan K.K.).
All formulations contain a minor amount(<0.01 ppw) of Megafac R-08 (tradename) surfactant.

Example 238 and Comparative Examples 205 and 206

The following ingredients were mixed together to prepare three solutions of a positive-working chemically amplified radiation sensitive composition suitable for DUV (248 nm) exposure:
9.8 g of the terpolymer (POLY 202) of the Example 202,
0.52 g (0.708 mmol) of tris-(4-t-butylphenyl) sulfonium nonafluorobutane sulfonate (Example 238),
0.66 g (0.708 mmol) of tris-(4-t-butylphenyl) sulfonium perfluorooctane sulfonate (Comparative Example 205) or
0.41 g (0.708 mmol) of tris-(4-t-butylphenyl) sulfonium trifluoromethane sulfonate (Comparative Example 206),
0.02 g of triphenyl sulfonium acetate,
0.004 g of Megafac R-08 (tradename), and
64.2 g of propylene glycol monomethyl ether acetate.

For comparison, positive-working chemically amplified radiation sensitive composition solutions were prepared in the same manner as described just above, except that 0.66 g (0.708 mmol) of tris-(4-t-butylphenyl)sulfonium perfluorooctane sulfonate (Comparative Example 205) or 0.41 g (0.708 mmol) of tris-(4-t-butylphenyl)sulfonium trifluoromethane sulfonate (Comparative Example 206) was used instead of 0.52 g (0.708 mmol) of tris-(4-t-butylphenyl) sulfonium nonafluorobutane sulfonate. The solutions were filtered, and spin coated on two silicon wafers each, which have been precoated with DUV 30, an antireflective coating provided by Brewer Science at a film thickness of 90 nm (bake conditions: 190° C./60 sec). The substrate reflectivity at this film thickness was approximately 6%. The films were baked for 90 seconds at 120° C. to yield films having a thickness of 0.72±0.01 µm and exposed as described in Example 201. The exposure was followed by a post exposure bake at 120° C. for 60 seconds and a development.

The following results (Table 204) were obtained.

TABLE 204

|  | Example 238 | Comparative Example 205 | Comparative Example 206 |
|---|---|---|---|
| Dose (mJ/cm$^2$) | 25 (2) | 33 (3) | 24 (1) |
| Dense Line Resolution (µm) | 0.20 (1) | 0.24 (3) | 0.22 (1) |
| Isolated Line Resolution (µm) | 0.12 (1) | 0.15 (3) | 0.13 (2) |
| Dense Line DOF @ 0.22 µm (µm) | 0.5–0.6 (1) | 0.0 (3) | 0.3–0.4 (2) |
| Isolated Line DOF @ 0.22 µm (µm) | 1.8 (1) | 1.6 (3) | 1.7–1.8 (2) |
| Dense Pattern Profile @ 0.18 µm | Very Good (1) | good (2) | Good (2) |
| Isolated Pattern Profile @ 0.15 µm | Good (1) | Film Loss (3) | Tapered (2) |
| Standing Waves | Visible (2) | Strong (2) | Visible (1) |
| Dense/iso bias @ 0.22 µm (nm) | 12 (1) | Na (3) | 23 (2) |

The test items in the table were the same as those in Table 203. From these results, it can be concluded that the material of the present invention has some superiority in the overall performance.

Example 239 and Comparative Examples 207 and 208

The following ingredients were mixed together to prepare three solutions of a positive-working chemically amplified radiation sensitive composition suitable for DUV (248 nm) exposure.
9.8 g of the terpolymer (POLY 203) of Example 203,
0.5 g of α, α-bis(cyclohexylsulfonyl)diazomethane,
0.52 g of tris-(4-t-butylphenyl) sulfonium nonafluorobutane sulfonate (Example 239),
0.03 g of triphenyl sulfonium acetate,
0.004 g of Megafac R-08 (tradename), and
64.2 g of propylene glycol monomethyl ether acetate.

For comparison, positive-working chemically amplified radiation sensitive composition solutions were prepared in the same manner as described just above, except that 0.52 g of tris-(4-t-butylphenyl)sulfonium trifluoromethane sulfonate (Comparative Example 207) or 0.52 g of bis-(4-t-butylphenyl)iodonium trifluoromethane sulfonate (Comparative Example 208) was used instead of 0.52 g of tris-(4-t-butylphenyl)sulfonium nonafluorobutane sulfonate.

The solutions were filtered, and spin coated on two silicon wafers each, which have been precoated with DUV 42, a antireflective coating provided by Brewer Science Corp., USA, at a film thickness of 60 nm (bake conditions: 200° C./60 sec). The substrate reflectivity at this film thickness was less than 5%. Baking for 90 seconds at 90° C. provided a layer having a thickness of 0.65±0.01 µm. Top-view inspection of the photoresists by microscope and scanning electron microscope indicated that all three films exhibited smooth surfaces without any sign of pinholes, popcorns, or cracking. The recording materials were exposed as described in Example 201 (NA=0.55, σ=0.55) using a half-tone mask with 0.3 µm contact hole patterns at the following dose, baked at 105° C. for 90 seconds and developed.

The results are summarized in Table 205.

TABLE 205

|  | Example 239 | Comparative Example 207 | Comparative Example 208 |
|---|---|---|---|
| Dose (mJ/cm$^2$) | 45 (3) | 44 (2) | 35 (1) |
| Dense C/H Resolution (µm) | 0.22 (1) | 0.22 (1) | 0.22 (1) |
| Isolated C/H Resolution (µm) | 0.22 (1) | 0.23 (2) | 0.23 (2) |
| Dense C/H DOF @ 0.25 µm (µm) | 1.8 (1) | 1.7 (2) | 1.6 (3) |
| Isolated C/H DOF @ 0.25 µm (µm) | 1.3 (1) | 1.1 (3) | 1.2 (2) |
| C/H Sidewalls @ 0.25 µm | Vertical (1) | Vertical (1) | Tapered (2) |
| C/H Bottom @ 0.25 µm | Good (1) | Foot (2) | Undercut (3) |
| C/H Top @ 0.25 µm | Clear (1) | Round (3) | Round (2) |
| Standing Waves | Visible (1) | Visible (1) | Visible (1) |
| Surface After Development | Smooth (1) | Popcorn (2) | Popcorn (2) |

The test items were the same as those in Table 203. These results indicate the material of the present invention are superior in performance also in use as contact hole resist.

Example 240 and Comparative Example 209

Monodisperse poly-(4-hydroxystyrene) (provided from Nippon Soda Corp.) was reacted with ethyl vinyl ether to prepare a copolymer. The copolymer had a molecular weight of 6,800 with 32% of the phenolic hydroxy groups protected.

The following ingredients were mixed together to prepare two solutions of a positive-working chemically amplified radiation sensitive composition suitable for DUV (248 nm) exposure.
9.8 g of the above resin,
1.2 g of a divinyl ether derivative prepared by the Williamson ether reaction of 1 mol bisphenol A with 2 moles 2-chloroethyl vinyl ether,
0.52 g (0.708 mol) of tris-(4-t-butylphenyl) sulfonium nonafluorobutane sulfonate (Example 240),
0.03 g of triphenyl sulfonium acetate,
0.004 g of Megafac R-08 (tradename), and
64.2 g of propylene glycol monomethyl ether acetate.

For comparison, positive-working chemically amplified radiation sensitive composition solutions were prepared in the same manner as described just above, except that 0.41 g (0.708 mmol) of tris-(4-t-butylphenyl)sulfonium trifluoromethane sulfonate (Comparative Example 209) was used instead of 0.52 g (0.708 mmol) of tris-(4-t-butylphenyl) sulfonium nonafluorobutane sulfonate.

The solutions thus obtained were filtered and spin coated on two silicon wafers each, which have been precoated with AZ KrF-2 (tradename), an antireflective coating provided by Clariant Japan K.K., at a film thickness of 60 nm (bake conditions: 220° C./60 sec). The photoresist films were baked for 90 seconds at 115° C. to yield a film thickness of 0.62±0.01 µm. After exposure as described in Example 201 (NA=0.55, σ=0.55) at a dose of 32 mJ/cm$^2$, the exposed wafers were baked at 120° C. for 90 seconds and developed.

The recording material of the present invention resolved lines and spaces down to 0.20 µm with vertical sidewalls profiles. The material of the Comparative Example 209 showed a resolution limit at 0.28 µm and strong foot formation. A dissolution rate analysis revealed that the contrast of the comparative material was significantly degraded probably due to a crosslinking reaction of the divinyl ether derivative at the selected post exposure bake temperature.

Example 241

The following ingredients were mixed together to prepare two positive-working chemically amplified radiation sensitive composition solutions suitable for i-line (365 nm) exposure:
8.6 g of a copolymer (molecular weight 12,200) of 3-methyl-4-hydroxystyrene and 4-hydroxystyrene (2:1),
2.8 g of the poly-N,O-acetal described in Example 238,
0.45 g of 2-anthryl diphenyl sulfonium nonafluorobutane sulfonate,
0.04 g of triphenyl sulfonium hydroxide,
0.004 g of Megafac R-08 (tradename), and
88.5 g of ethyl lactate.

The solution thus obtained was filtered and spin coated on a wafer precoated with a 160 nm thick film of AZ Barli (tradename), a commercial antireflective coating available from Clariant Japan K.K., which has been baked at 200° C. for 60 seconds. The photoresist was baked at 110° C. for 60 seconds to give a film thickness of 850 nm. The coated wafer was exposed through a mask with line and space patterns down to 0.20 $\mu$m using a Nikon SNR1705I stepper (NA=0.50) at a dose of 56 mJ/cm$^2$. After the exposure, the wafer was baked at 90° C. for 60 seconds and developed as described in Example 201. After pure water rinsing, the wafer was dried and observed under SEM. The material resolved 0.26 $\mu$m lines and space patterns free of scum and T-top formation.

Example 242

Two solutions of a positive-working chemically amplified radiation sensitive composition suitable for VDUV (193 nm) exposure were prepared by mixing the following ingredients together:
11.14 g of poly(2-hydroxystyrene-co-2-methyl-2-adamantyl methacrylate-co-mevalonic lactone methacrylate) with a molecular weight of 8,000 and a polydisersity of 1.82,
0.31 g of bis-4-cyclohexylphenyl iodonium nonafluorobutane sulfonate,
0.04 g of methyl diethanolamine,
0.004 g of Megafac R-08 (tradename), and
88.5 g of ethyl lactate.

The solution thus obtained was filtered and spin coated on a wafer precoated with a 60 nm thick film of an experimental methacrylate based antireflective coating provided by Clariant Japan K.K., which has been baked at 200° C. for 60 seconds. The photoresist was baked at 90° C. for 60 seconds to give a film thickness of 450 nm and exposed through a mask with line and space patterns down to 0.10 $\mu$m using a ISI ArF excimer laser with a NA=0.60 at a dose of 14.5 mJ/cm$^2$. After the exposure, the wafer was baked at 110° C. for 60 seconds and developed with an aqueous developer AZ MIF 300 (tradename: available from Clariant Japan K.K.) containing 2.38% tetramethyl ammonium hydroxide for 60 seconds at 23° C. The material resolved 0.14 $\mu$m lines and space pattern without any T-top formation. The interface between the antireflective coating and the photoresist was free of scum.

Example 243

Two solutions of negative-working chemically amplified radiation sensitive composition suitable for DUV (248 nm) exposure were prepared by mixing the following ingredients together:
7.9 g of a copolymer of 4-hydroxystyrene and styrene prepared by radical polymerization in the presence of 2,2'-azobis(4-methoxy-2,4-dimethylvaleronitrile) as a polymerization initiator, the copolymer having a molecular weight of 9,200 and a polydispersity of 2.14 as determined by GPC using polystyrene as the standard and a monomer ratio of 8:2 as determined by $^1$H-NMR,
2.0 g of distilled hexamethoxymethyl melamine,
0.3 g of tris-(4-t-butylphenyl) sulfonium nonafluorobutane sulfonate,
0.02 g of tetrabutyl ammonium lactate,
0.004 g of Megafac R-08 (tradename), and
62.4 g of propylene glycol monomethyl ether acetate.

The solution thus obtained was filtered, spin coated onto a HMDS treated silicon wafer at 3,000 rpm, and baked on a hot plate at 115° C. for 60 seconds. The resulting film thickness was 0.72 $\mu$m. An exposure as described in Example 201 followed at a dose of 32 mJ/cm$^2$. The exposed material was then subjected to a post exposure bake on a hot plate at 125° C. for 90 seconds and developed. The fine lines and spaces were resolved down to 0.20 $\mu$m. Isolated lines were resolved down to 0.16 $\mu$m when a dose of 38 mJ/cm$^2$ was applied. The depth-of-focus of the 0.16 $\mu$m lines was about 0.80 $\mu$m.

Examples 244 and 245

A solution of negative-working chemically amplified radiation sensitive composition suitable for DUV (248 nm) and e-beam exposure was prepared by mixing the following ingredients together:
7.9 g of a copolymer of 4-hydroxystyrene and 4-methoxystyrene prepared by radical polymerization in the presence of 2,2'-azobis(isobutyronitrile) as a polymerization initiator, the copoylmer having a molecular weight of 9,600 and a polydispersity of 2.21 as determined by GPC using polystyrene as the standard and a monomer ratio of 7.8:2.2 as determined by $^1$H-NMR,
2.0 g of recrystallized tetramethoxymethyl glucoril,
0.5 g of tetrabutoxymethyl glucoril,
0.3 g of tris-(4-t-butylphenyl) sulfonium nonafluorobutane sulfonate,
0.02 g of tetramethyl ammonium hydroxide,
0.004 g of Megafac R-08 (tradename), and
62.4 g of propylene glycol monomethyl ether acetate.

The solution thus obtained was filtered and spin coated onto two silicon wafers treated with an adhesion promoter (hexamethyl disilazane) at 3,000 rpm. After baking on a hot plate at 95° C. for 60 seconds, a film thickness of 0.74±0.2 $\mu$m was obtained. One wafer was subjected to an exposure through a mask with fine lines and space patterns down to 0.10 $\mu$m using a Nikon NSR 2005 EX 10B KrF excimer laser stepper (NA=0.55, $\sigma$=0.80) at a dose of 24 mJ/cm$^2$. The other wafer was exposed with e-beam using the e-beam writer described in Example 208 at a dose of 14.3 $\mu$C/Cm$^2$. The exposed materials then were subjected to a post exposure bake on a hot plate at 95° C. for 90 seconds and developed.

The excimer laser exposed material resolved fine lines and spaces down to 0.20 $\mu$m. Isolated lines were resolved down to 0.15 $\mu$m when a dose of 31 mJ/cm$^2$ was applied. The depth-of-focus of the 0.15 $\mu$m lines was about 0.90 $\mu$m.

The e-beam exposed material yielded isolated lines with a linewidth below 0.10 $\mu$m.

Examples 246 and 247

Two solutions of a negative-working chemically amplified radiation sensitive composition suitable for DUV (248 nm) and x-ray exposure were prepared by mixing the following ingredients together:

5.9 g of a terpolymer of 4-hydroxystyrene, styrene and N-hydroxymethyl methacrylamide with a molecular weight of 11,500, a polydispersity of 1.69, and a monomer ratio of 8:1.8:0.2,
1.5 g of recrystallized tetramethoxymethyl glucoril,
0.5 g of 4,4'-(1-methylethylidene)-bis-[2,6-bis-(hydroxymethyl)-phenol]
0.3 g of bis-(t-butylphenyl) iodonium nonafluorobutane sulfonate,
0.02 g of tetramethyl ammonium hydroxide,
0.004 g of Megafac R-08 (tradename), and
62.4 g of propylene glycol monomethyl ether acetate.

The solution thus obtained was filtered and spin coated onto two silicon wafers treated with an adhesion promoter (hexamethyl disilazane) at 3,000 rpm. After baking on a hot plate at 95° C. for 60 seconds, a film thickness of 0.67±0.02 µm was obtained. One of the wafers was subjected to an exposure through a mask with fine lines and space patterns down to 0.10 µm using a Nikon NSR 2005 EX 10B KrF excimer laser stepper (NA=0.55, σ=0.55) at a dose of 18 mJ/cm². The other wafer was exposed with x-rays as described in Example 210 at a dose of 52 mJ/cm². The exposed materials were then subjected to a post exposure bake on a hot plate at 95° C. for 90 seconds and developed.

The fine lines and spaces of the excimer laser exposed material were resolved down to 0.22 µm. Isolated lines were resolved down to 0.18 µwhen a dose of 25 mJ/cm²was applied. The depth-of-focus of the 0.18 µm lines was about 1.25 µm.

The x-ray exposed material resolved dense lines and spaces down to 0.16 µm while isolated lines were resolved down below 0.16 µm.

Example 248 and Comparative Example 210

Two negative-working chemically amplified radiation sensitive composition solutions suitable for i-line (365 nm) exposure were prepared by mixing the following ingredients together:
7.2 g of a copolymer (molecular weight 15,000, glass transition temperature 145° C.) of 3,5-dimethyl-4-hydroxystyrene and 4-hydroxystyrene (3:7),
2.0 g of distilled hexamethoxymethyl melamine,
0.02 g of tetramethyl ammonium hydroxide,
0.004 g of Megafac R-08 (tradename), and
42.4 g of propylene glycol monomethyl ether acetate.

To one of the base formulations, a solution of 0.35 g of (4-phenyl-thiophenyl) diphenyl sulfonium nonafluorobutane sulfonate dissolved in 20 g of propylene glycol monomethyl ether acetate was added (Example 248), while to the other base formulation,
0.35 g of (4-phenyl-thiophenyl) diphenyl sulfonium trifluoromethane sulfonate dissolved in 20 g of propylene glycol monomethyl ether acetate was added (Comparative Example 210). The solutions thus obtained were filtered and spin coated onto HMDS treated silicon wafers at 2,400 rpm. After baking on a hot plate at 90° C. for 60 seconds, both materials yielded a film thickness of 1.06±0.03 µm.

The wafers were subjected to an exposure through a mask with fine lines and space patterns down to 0.20 µm using a Nikon NSR 1755i 7a i-line stepper at a dose of 82 mJ/cm². The exposed materials were then baked on a hot plate at 105° C. for 90 seconds and developed.

The material of the Example 248 resolved 0.28 µm lines and spaces patterns and the profile of the resist patterns were ideally rectangular. No whisker-like raised portions or scum were observed. The dose to print isolated lines with a width of 0.28 µm was found to be 91 mJ/cm².

The material of the Comparative Example 210 also resolved 0.28 µm lines and spaces patterns. However, the top of the line patterns was rounded, and the bottom of the line patterns had an undercut structure combined with severe scum. The dose to print isolated lines with a width of 0.28 µm was found to be 95 mJ/cm²and therefore this formulation (Comparative Example 210) was judged to be clearly inferior to that of the Example 248.

Example 249 and Comparative Example 211

From Example 204, it is evident that the replacement of triflate based PAGs with the nonaflate based PAGs of the present invention yields radiation sensitive compositions with identical sensitivity and resolution capability.

A first quartz wafer was coated with a solution containing a mixture of
5.0 g of poly-(4-hydroxystyrene), and
0.3 g of tris-(4-t-butylphenyl)sulfonium nonafluorobutane sulfonate dissolved in 50 g of propylene glycol monomethyl ether actetate and baked at 120° C. for 60 seconds (Example 249, wafer 201).

A second quartz wafer was coated with a solution containing a mixture of
5.1 g poly-(4-hydroxystyrene), and
0.3 g tris-(4-t-butylphenyl)sulfonium triflate dissolved in 50 g propylene glycol monomethyl ether acetate and baked at 120° C. for 60 seconds (Comparative Example 211, wafer 202).

In addition, two other quartz wafers were coated with a solution of
5.0 g poly-(4-t-butyloxycarbonyloxystyrene) dissolved in 50 g propylene glycol monomethyl ether acetate and baked at 90° C. for 90 seconds (wafer 203 and wafer 204). Wafers 203 and 204 were subjected to a quantitative FIR spectrum analysis with respect to the absorption intensity of the carbonyl bond. Then the film on wafer 203 was brought into intimate contact with the film on wafer 201 and the film on wafer 204 with the film on wafer 202 each at a pressure of about 0.05 kg/cm². Both wafer pairs were subjected to a flood irradiation with DUV KrF excimer laser irradiation at a dose of 80 mJ/cm² and baked at 90° C. for 90 seconds with wafers 203 and 204 on the upper side. The wafers 203 and 204 were separated from wafers 201 and 202 and their FIR spectra were again recorded. After substraction of the two spectra (before and after exposure/bake), it became evident that 47% of the t-butyloxycarbonyloxy groups of the polymer on wafer 204 had been cleaved into hydroxy groups by trifluoromethanesulfonic acid produced during exposure and diffusing into the polymer during the post exposure bake, while only 14% of the t-butyloxycarbonyloxy groups of the polymer on wafer 203 had been cleaved, indicating that the trifluoromethane sulfonic acid produced from wafer 202 was much more volatile than the nonafluorobutane sulfonic acid produced from wafer 201. From this experiment, it can be concluded that the amount of acidic, corrosive and volatile products which might cause destruction of the irradiation equipment and pose hazards to the health of the workers is significantly reduced, when triflate generating PAGs were replaced with the PAGs of the present invention.

Example 250

The radiation sensitive composition of Example 241 was coated on a mechanically surface grained aluminum foil and dried to a weight of about 1.2 g/m². After imagewise exposure through a positive-working original with a 5 kW metal halide light source for 23 seconds, the foil was heated at 100° C. for 8 minutes in a convection oven. The printed image was developed with a developer solution containing the following ingredients by a splash paddle method:

5.0 g of sodium lauryl sulfate,
1.5 g of sodium metasilicate pentahydrate,
1.6 g of trisodium phosphate dodecahydrate, and
92.5 g of ion-exchanged water.

The plate was then rinsed with pure water and dried. Step 6 of a silver-film continuous-tone step having a density range from 0.05 to 3.05 and density increments of 0.15 was completely reproduced on the copy. Even the finest screens and lines of the original were clearly visible. The printing plate obtained in the manner described gave 32,000 high quality impressions on a sheetfed offset printing machine.

What is claimed is:

1. A chemically amplified radiation sensitive composition comprising:

an onium salt precursor, which generates a fluorinated alkanesulfonic acid, as a photoacid generator, wherein the alkanesulfonic acid has 4 carbon atoms, and wherein the onium salt precursor which generates a fluorinated alkanesulfonic acid is a sulfonium or iodonium salt of nonafluorobutane sulfonate, and wherein the photoacid generator is a sulfonium or iodonium salt of a fluorinated alkane sulfonic acid, represented by formula (I):

$$Y^+ASO_3^-  \quad (I)$$

wherein A represents $CF_3CF_2CF_2CF_2$; and

Y represents

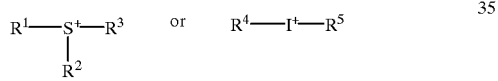

wherein $R^1$, $R^2$, $R^3$, $R^4$, and $R^5$ each independently represent an alkyl group, a monocyclic or bicyclic alkyl group, a cyclic alkylcarbonyl group, a naphthyl group, an anthryl group, a peryl group, a pyryl group, a thienyl group, an aralkyl group, or an arylcarbonylmethylene group, or any two of $R^1$, $R^2$, and $R^3$ or $R^4$ and $R^5$ together represent an alkylene or an oxyalkylene which forms a five- or six-membered ring together with the interposing sulfur or iodine, said ring being optionally condensed with aryl groups, one or more hydrogen atoms of $R^1$, $R^2$, $R^3$, $R^4$, and $R^5$ being optionally substituted by one or more groups selected from the group consisting of a halogen atom, an alkyl group, a cyclic alkyl group, an alkoxy group, a cyclic alkoxy group, a dialkylamino group, a cyclic dialkylamino group, a hydroxyl group, a cyano group, a nitro group, an aryl group, an aryloxy group, an arylthio group, and groups of formulae (II) to (VI):

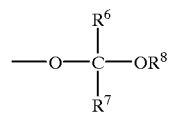 (II)

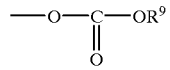 (III)

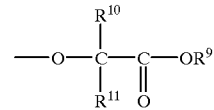 (IV)

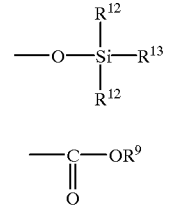 (V)

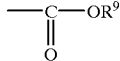 (VI)

wherein $R^6$ and $R^7$ each independently represent a hydrogen atom, an alkyl group, which may be substituted by one or more halogen atoms, or a cyclic alkyl group, which may be substituted by one or more halogen atoms, or $R^6$ and $R^7$ together can represent an alkylene group to form a ring, $R^8$ represents an alkyl group, a cyclic alkyl group, or an aralkyl group, or $R^6$ and $R^8$ together represent an alkylene group which forms a ring together with the interposing —C—O— group, the carbon atom in the ring being optionally substituted by an oxygen atom, $R^9$ represents an alkyl group or a cyclic alkyl group, one or two carbon atoms in the alkyl group or the cyclic alkyl group being optionally substituted by an oxygen atom, an aryl group, or an aralkyl group, $R^{10}$ and $R^{11}$ each independently represent a hydrogen atom, an alkyl group, or a cyclic alkyl group, $R^{12}$ represents an alkyl group, a cyclic alkyl group, an aryl group, or an aralkyl group, and $R^{13}$ represents an alkyl group, a cyclic alkyl group, an aryl group, an aralkyl group, the group —Si($R^{12})_2R^{13}$, or the group —O—Si($R^{12})_2R^{13}$; and a film forming hydroxystyrene based resin, wherein said film forming hydroxystyrene based resin is a polymer of 4-hydroxystyrene, 3-hydroxystyrene, or 2-hydroxystyrene, or a co-, ter-, quarter- or pentapolymer of the styrenes and other monomers, or wherein said film forming hydroxystyrene resin that is a polymer of 4hydroxystyrene, 3-hydroxystyrene, or 2-hydroxystyrene, or a co-, ter-, quarter- or pentapolymer of the styrenes and other monomers, is made alkali insoluble by protecting alkali soluble groups on the resin with an acid cleavable protecting group.

2. The composition according to claim 1, which is a positive-working chemically amplified radiation sensitive composition.

3. The composition according to claim 2, wherein said resin has multiple acid cleavable C—O—C or C—O—Si bonds.

4. The composition according to claim 2, wherein said resin has a molecular weight of 2,000 to 200,000 and a polydispersity of 1.01 to 2.80.

5. The composition according to claim 2, which further comprises a dissolution inhibitor with at least one acid cleavable C—O—C or C—O—Si bond.

6. The composition according to claim 5, wherein said dissolution inhibitor is a phenolic and/or carboxylic acid type compound with at least one acid cleavable C—O—C or C—O—Si bond and having a molecular weight of approximately 100 to 20,000.

7. The composition according to claim 2, which further comprises other performance improving additives.

8. A composition which comprises:
   (1) 0.1 to 30 parts by weight of a sulfonium or iodonium salt of a fluorinated alkane sulfonic acid, represented by formula (I) of claim 1;
   (2) 100 parts by weight of said film forming hydroxystyrene based resin of claim 1, with multiple acid cleavable C—O—C or C—O—Si bonds;
   (3) 0 to 50 parts by weight of a dissolution inhibitor with at least one acid cleavable C—O—C or C—O—Si bond; and
   (4) 0.01 to 5.0 parts by weight of a performance improving additive.

9. The composition according to claim 1, which is a negative-working chemically amplified radiation sensitive composition.

10. The composition according to claim 9, wherein said film forming hydroxystyrene based resin is an alkali soluble and acid-sensitive self-crosslinkable resin.

11. The composition according to claim 9, which further comprises an acid-sensitive crosslinking agent.

12. The composition according to claim 11, wherein said crosslinking agent is a melamine/formaldehyde condensate and/or a urea/formaldehyde condensate with at least two acid-crosslinkable groups.

13. The composition according to claim 9, wherein said resin has a molecular weight of 2,000 to 200,000 and a polydispersity of 1.01 to 2.80.

14. The composition according to claim 9, which further comprises other performance improving additives.

15. The composition according to claim 14, which comprises:
   (1) 0.1 to 30 parts by weight of a sulfonium or iodonium salt of a fluorinated alkane sulfonic acid, represented by formula (I);
   (2) 100 parts by weight of said hydroxystyrene based resin;
   (3) 3 to 70 parts by weight of an acid-sensitive crosslinking agent; and
   (4) 0.01 to 5.0 parts by weight of said performance improving additives.

16. The composition according to claim 1, wherein said radiation sensitive photoacid generator is a compound of formula (I), where $R^1$, $R^2$, $R^3$, $R^4$, and $R^5$ each independently represent
   a $C_{1-12}$ alkyl group,
   a $C_{6-12}$ monocyclic or bicyclic alkyl group,
   a $C_{4-12}$ cyclic alkylcarbonyl group,
   a naphthyl group,
   an anthryl group,
   a peryl group,
   a pyryl group,
   a thienyl group,
   an aralkyl group, or
   an arylcarbonylmethylene group with up to 15 carbon atoms, or
   any two of $R^1$, $R^2$, and $R^3$, or $R^4$ and $R^5$ together represent an alkylene or an oxyalkylene which forms a five- or six-membered ring together with the interposing sulfur or iodine atom, said ring being optionally condensed with aryl groups.

17. The composition according to claim 16, wherein said radiation sensitive photoacid generator is a compound of formula (I),
   wherein one or more hydrogen atoms of $R^1$, $R^2$, $R^3$, $R^4$, and $R^5$ are optionally substituted by at least one group selected from the group consisting of a halogen atom, a $C_{1-6}$ alkyl group, a $C_{3-6}$ cyclic alkyl group, a $C_{1-6}$ alkoxy group, a $C_{3-6}$ cyclic alkoxy group, a di-$C_{1-3}$ alkylamino group, a cyclic di-$C_{6-12}$ alkylamino group, a hydroxyl group, a cyano group, a nitro group, an aryloxy group, an arylthio group, and groups represented by formulae (II), (III), (IV), (V), and (VI),
   wherein $R^6$ and $R^7$ each independently represent a hydrogen atom, a $C_{1-6}$ alkyl group, which may be substituted by one or more halogen atoms, or a $C_{3-6}$ cyclic alkyl group, which may be substituted by one or more halogen atoms, or $R^6$ and $R^7$ together represent an alkylene group to form a five-membered or six-membered ring,
   $R^8$ represents a $C_{1-6}$ alkyl group, a $C_{3-6}$ cyclic alkyl group, or a $C_{7-12}$ aralkyl group, or $R^6$ and $R^8$ together represent an alkylene group which forms a five- or six-membered ring together with the interposing —C—O— group, the carbon atom in the ring being optionally substituted by an oxygen atom,
   $R^9$ represents a $C_{1-6}$ alkyl group or a $C_{3-6}$ cyclic alkyl group, one or two carbon atoms in the alkyl group or the cyclic alkyl group being optionally substituted by an oxygen atom, a $C_{6-12}$ aryl group, or a $C_{7-12}$ aralkyl group,
   $R^{10}$ and $R^{11}$ each independently represent a hydrogen atom, a $C_{1-6}$ alkyl group, or a $C_{3-6}$ cyclic alkyl group,
   $R^{12}$ represents a $C_{1-6}$ alkyl group, a $C_{3-6}$ cyclic alkyl group, a $C_{6-12}$ aryl group, or a $C_{7-12}$ aralkyl group, and
   $R^{13}$ represents a $C_{1-6}$ alkyl group, a $C_{3-6}$ cyclic alkyl group, a $C_{6-12}$ aryl group, a $C_{7-12}$ aralkyl group, group —Si$(R^{12})_2R^{13}$, or group —O—Si$(R^{12})_2R^{13}$.

18. The composition according to claim 1, wherein, in the compound of formula (I),
   $R^1$, $R^2$, $R^3$, $R^4$, and $R^5$ each independently represent a $C_{1-3}$ alkyl group, a $C_{3-6}$ monocyclic alkyl group, $C_{10-12}$ bicyclic alkyl group, a $C_{3-6}$ cyclic alkylcarbonyl group, or a naphthyl group, or any two of $R^1$, $R^2$ and $R^3$, or $R^4$ and $R^5$ together represent an alkylene group to form a five- or six-membered alkylene ring,
   one or more hydrogen atoms of $R^1$, $R^2$, $R^3$, $R^4$, and $R^5$ optionally substituted by at least one group selected from the group consisting of a hydrogen atom, a halogen atom, a $C_{1-6}$ alkyl group, a $C_{3-6}$ cyclic alkyl group, a $C_{1-6}$ alkoxyl group, a $C_{3-6}$ cyclic alkoxyl group, a hydroxyl group, an aryloxy group, an arylthio group, and groups of formulae (II), (III), (IV), (V), and (VI),
   wherein $R^6$ and $R^7$ each independently represent either a hydrogen atom or a methyl group, provided that $R^6$ and $R^7$ do not simultaneously represent hydrogen, $R^8$ represents either a $C_{1-4}$ alkyl group or $R^6$ and $R^8$ together represent an alkylene group which forms a ring together with the interposing —C—O— group, $R^9$ represents a $C_{1-4}$ alkyl group, $R^{10}$ and $R^{11}$ represent a hydrogen atom, $R^{12}$ represents a methyl group, and $R^{13}$ represents a methyl group.

19. An iodonium salt of formula (I) as defined in claim 1.

20. A sulfonium salt of formula (I) as defined in claim 1, wherein at least one hydrogen atom on group represented by $R^1$, $R^2$, or $R^3$ is substituted by a substituent defined in claim 1.

21. A chemically amplified radiation sensitive composition comprising: an onium salt precursor, which generates a fluorinated alkanesulfonic acid, as a photoacid generator, wherein the alkanesulfonic acid has 3 carbon atoms, and wherein the onium salt precursor which generates a fluorinated alkanesulfonic acid is a sulfonium or iodonium salt of hexafluoropropane sulfonate, and wherein the photoacid generator is a sulfonium or iodonium salt of a fluorinated alkane sulfonic acid, represented by formula (I):

$$Y^+ASO_3^- \qquad (I)$$

wherein A represents $CF_3CHFCF_2$; and

Y represents

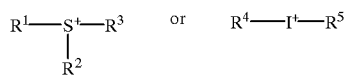

wherein $R^1$, $R^2$, $R^3$, $R^4$, and $R^5$ each independently represent an alkyl group, a monocyclic or bicyclic alkyl group, a cyclic alkylcarbonyl group, a phenyl group, a naphthyl group, an anthryl group, a peryl group, a pyryl group, a thienyl group, an aralkyl group, or an arylcarbonylmethylene group, or any two of $R^1$, $R^2$, and $R^3$ or $R^4$ and $R^5$ together represent an alkylene or an oxyalkylene which forms a five- or six-membered ring together with the interposing sulfur or iodine, said ring being optionally condensed with aryl groups, one or more hydrogen atoms of $R^1$, $R^2$, $R^3$, $R^4$, and $R^5$ being optionally substituted by one or more groups selected from the group consisting of a halogen atom, an alkyl group, a cyclic alkyl group, an alkoxy group, a cyclic alkoxy group, a dialkylamino group, a cyclic dialkylamino group, a hydroxyl group, a cyano group, a nitro group, an aryl group, an aryloxy group, an arylthio group, and groups of formulae (II) to (VI):

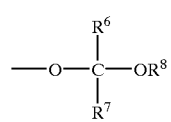

(II)

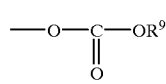

(III)

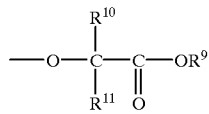

(IV)

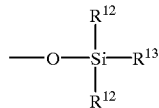

(V)

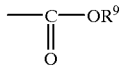

(VI)

wherein $R^6$ and $R^7$ each independently represent a hydrogen atom, an alkyl group, which may be substituted by one or more halogen atoms, or a cyclic alkyl group, which may be substituted by one or more halogen atoms, or $R^6$ and $R^7$ together can represent an alkylene group to form a ring, $R^8$ represents an alkyl group, a cyclic alkyl group, or an aralkyl group, or $R^6$ and $R^8$ together represent an alkylene group which forms a ring together with the interposing —C—O— group, the carbon atom in the ring being optionally substituted by an oxygen atom, $R^9$ represents an alkyl group or a cyclic alkyl group, one or two carbon atoms in the alkyl group or the cyclic alkyl group being optionally substituted by an oxygen atom, an aryl group, or an aralkyl group, $R^{10}$ and $R^{11}$ each independently represent a hydrogen atom, an alkyl group, or a cyclic alkyl group, $R^{12}$ represents an alkyl group, a cyclic alkyl group, an aryl group, or an aralkyl group, and $R^{13}$ represents an alkyl group, a cyclic alkyl group, an aryl group, an aralkyl group, the group —Si($R^{12}$)$_2$$R^{13}$, or the group —O—Si($R^{12}$)$_2$$R^{13}$; and a film forming hydroxystyrene based resin, wherein said film forming hydroxystyrene based resin is a ter-, quarter- or pentapolymer of 4-hydroxystyrene, 3-hydroxystyrene, or 2-hydroxystyrene, and other monomers, or wherein said film forming hydroxystyrene based resin that is a ter-, quarter- or pentapolymer of 4-hydroxystyrene, 3-hydroxystyrene, or 2-hydroxystyrene, and other monomers, is made alkali insoluble by protecting alkali soluble groups on the resin with an acid cleavable protecting group.

22. The composition according to claim 21, which is a positive-working chemically amplified radiation sensitive composition.

23. The composition according to claim 22, wherein said resin has multiple acid cleavable C—O—C or C—O—Si bonds.

24. The composition according to claim 22, wherein said resin has a molecular weight of 2,000 to 200,000 and a polydispersity of 1.01 to 2.80.

25. The composition according to claim 22, which further comprises a dissolution inhibitor with at least one acid cleavable C—O—C or C—O—Si bond.

26. The composition according to claim 25, wherein said dissolution inhibitor is a phenolic and/or carboxylic acid type compound with at least one acid cleavable C—O—C or C—O—Si bond and having a molecular weight of approximately 100 to 20,000.

27. The composition according to claim 22, which further comprises other performance improving additives.

28. A composition which comprises:
  (1) 0.1 to 30 parts by weight of a sulfonium or iodonium salt of a fluorinated alkane sulfonic acid, represented by formula (I) of claim 21;
  (2) 100 parts by weight of said film forming hydroxystyrene based resin of claim 21, with multiple acid cleavable C—O—C or C—O—Si bonds;
  (3) 0 to 50 parts by weight of a dissolution inhibitor with at least one acid cleavable C—O—C or C—O—Si bond; and
  (4) 0.01 to 5.0 parts by weight of a performance improving additive.

29. The composition according to claim 21, which is a negative-working chemically amplified radiation sensitive composition.

30. The composition according to claim 29, wherein said film forming hydroxystyrene based resin is an alkali soluble and acid-sensitive self-crosslinkable resin.

31. The composition according to claim 29, which further comprises an acid-sensitive crosslinking agent.

32. The composition according to 31, wherein said crosslinking agent is a melamine/formaldehyde condensate and/or a urea/formaldehyde condensate with at least two acid-crosslinkable groups.

33. The composition according to claim 29, wherein said resin has a molecular weight of 2,000 to 200,000 and a polydispersity of 1.01 to 2.80.

34. The composition according to claim 29, which further comprises other performance improving additives.

35. A composition which comprises:
  (1) 0.1 to 30 parts by weight of a sulfonium or iodonium salt of a fluorinated alkane sulfonic acid, represented by formula (I) of claim 21;
  (2) 100 parts by weight of said film forming hydroxystyrene based resin of claim 21;
  (3) 3 to 70 parts by weight of an acid-sensitive crosslinking agent; and
  (4) 0.01 to 5.0 parts by weight of a performance improving additive.

36. The composition according to claim 21, wherein said radiation sensitive photoacid generator is a compound of formula (I), where $R^1$, $R^2$, $R^3$, $R^4$, and $R^5$ each independently represent
  a $C_{1-12}$ alkyl group,
  a $C_{6-12}$ monocyclic or bicyclic alkyl group,
  a $C_{4-12}$ cyclic alkylcarbonyl group,
  a phenyl group,
  a naphtyl group,
  an anthryl group,
  a peryl group,
  a pyryl group,
  a thienyl group,
  an aralkyl group, or
  an arylcarbonylmethylene group with up to 15 carbon atoms, or
  any two of $R^1$, $R^2$, and $R^3$, or $R^4$ and $R^5$ together represent an alkylene or an oxyalkylene which forms a five- or six-membered ring together with the interposing sulfur or iodine atom, said ring being optionally condensed with aryl groups.

37. The composition according to claim 36, wherein said radiation sensitive photoacid generator is a compound of formula (I),
  wherein one or more hydrogen atoms of $R^1$, $R^2$, $R^3$, $R^4$, and $R^5$ are optionally substituted by at least one group selected from the group consisting of a halogen atom, a $C_{1-6}$ alkyl group, a $C_{3-6}$ cyclic alkyl group, a $C_{1-6}$ alkoxy group, a $C_{3-6}$ cyclic alkoxy group, a di-$C_{1-3}$ alkylamino group, a cyclic di-$C_{6-12}$ alkylamino group, a hydroxyl group, a cyano group, a nitro group, an aryl group, an aryloxy group, an arylthio group, and groups represented by formulae (II), (III), (IV), (V), and (VI),
  wherein $R^6$ and $R^7$ each independently represent a hydrogen atom, a $C_{1-6}$ alkyl group, which may be substituted by one or more halogen atoms, or a $C_{3-6}$ cyclic alkyl group, which may be substituted by one or more halogen atoms, or $R^6$ and $R^7$ together represent an alkylene group to form a five-membered or six-membered ring,
  $R^8$ represents a $C_{1-6}$ alkyl group, a $C_{3-6}$ cyclic alkyl group, or a $C_{7-12}$ aralkyl group, or $R^6$ and $R^8$ together represent an alkylene group which forms a five- or six-membered ring together with the interposing —C—O— group, the carbon atom in the ring being optionally substituted by an oxygen atom,
  $R^9$ represents a $C_{1-6}$ alkyl group or a $C_{3-6}$ cyclic alkyl group, one or two carbon atoms in the alkyl group or the cyclic alkyl group being optionally substituted by an oxygen atom, a $C_{6-12}$ aryl group, or a $C_{7-12}$ aralkyl group,
  $R^{10}$ and $R^{11}$ each independently represent a hydrogen atom, a $C_{1-6}$ alkyl group, or a $C_{3-6}$ cyclic alkyl group,
  $R^{12}$ represents a $C_{1-6}$ alkyl group, a $C_{3-6}$ cyclic alkyl group, a $C_{6-12}$ aryl group, or a $C_{7-12}$ aralkyl group, and
  $R^{13}$ represents a $C_{1-6}$ alkyl group, a $C_{3-6}$ cyclic alkyl group, a $C_{6-12}$ aryl group, a $C_{7-12}$ aralkyl group, group —Si$(R^{12})_2 R^{13}$, or group —O—Si$(R^{12})_2 R^{13}$.

38. The composition according to claim 21, wherein, in the compound of formula (I),
  $R^1$, $R^2$, $R^3$, $R^4$, and $R^5$ each independently represent a $C_{1-3}$ alkyl group, a $C_{3-6}$ monocyclic alkyl group, $C_{10-12}$ bicyclic alkyl group, a $C_{3-6}$ cyclic alkylcarbonyl group, a phenyl group, or a naphthyl group, or any two of $R^1$, $R^2$ and $R^3$, or $R^4$ and $R^5$ together represent an alkylene group to form a five- or six-membered alkylene ring,
  one or more hydrogen atoms of $R^1$, $R^2$, $R^3$, $R^4$, and $R^5$ optionally substituted by at least one group selected from the group consisting of a hydrogen atom, a halogen atom, a $C_{1-6}$ alkyl group, a $C_{3-6}$ cyclic alkyl group, a $C_{1-6}$ alkoxyl group, a $C_{3-6}$ cyclic alkoxyl group, a hydroxyl group, an aryl group, an aryloxy group, an arylthio group, and groups of formulae (II), (III), (IV), (V), and (VI),
  wherein $R^6$ and $R^7$ each independently represent either a hydrogen atom or a methyl group, provided that $R^6$ and $R^7$ do not simultaneously represent hydrogen, $R^8$ represents either a $C_{1-4}$ alkyl group or $R^6$ and $R^8$ together represent an alkylene group which forms a ring together with the interposing —C—O— group, $R^9$ represents a $C_{1-4}$ alkyl group, $R^{10}$ and $R^{11}$ represent a hydrogen atom, $R^{12}$ represents a methyl group, and $R^{13}$ represents a methyl group.

39. The composition according to claim 21, wherein said compound of formula (I) is a tris-(4-t-butylphenyl) sulfonium salt of a fluorinated alkane sulfonate.]

40. An iodonium salt of formula (I) as defined in claim 21.

41. A sulfonium salt of formula (I) as defined in claim 21, wherein at least one hydrogen atom on group represented by $R^1$, $R^2$, or $R^3$ is substituted by a substituent defined in claim 21.

42. Tris-(4-t-butylphenyl)sulfonium 3,3,3,2,1,1-hexafluoropropane sulfonate.

* * * * *